(12) United States Patent
Van Es et al.

(10) Patent No.: US 10,947,325 B2
(45) Date of Patent: Mar. 16, 2021

(54) REGULATORS FOR CONTROLLING LINEAR AND PSEUDO-RING EXPANSION POLYMERIZATION OF VINYL MONOMERS

(71) Applicant: DISPOLTEC B.V., Geleen (NL)

(72) Inventors: J. J. G Steven Van Es, Geleen (NL); J. M. Asua, Donostia-san Sebastián (ES); J. R. Leiza, Hernani (ES)

(73) Assignee: DISPOLTEC B.V., Geleen (NL)

( * ) Notice: Subject to any disclaimer, the term of this patent is extended or adjusted under 35 U.S.C. 154(b) by 175 days.

(21) Appl. No.: 15/773,039

(22) PCT Filed: Nov. 3, 2016

(86) PCT No.: PCT/EP2016/076596
§ 371 (c)(1),
(2) Date: May 2, 2018

(87) PCT Pub. No.: WO2017/076992
PCT Pub. Date: May 11, 2017

(65) Prior Publication Data
US 2018/0334516 A1     Nov. 22, 2018

Related U.S. Application Data

(63) Continuation-in-part of application No. PCT/EP2015/075750, filed on Nov. 4, 2015.

(51) Int. Cl.
C08F 2/38     (2006.01)
C07C 239/16     (2006.01)
(Continued)

(52) U.S. Cl.
CPC .............. C08F 2/38 (2013.01); C07C 207/04 (2013.01); C07C 239/14 (2013.01);
(Continued)

(58) Field of Classification Search
None
See application file for complete search history.

(56) References Cited

U.S. PATENT DOCUMENTS

6,342,647 B1     1/2002    Roof et al.

FOREIGN PATENT DOCUMENTS

WO     9813392 A1     4/1998
WO     9903894 A1     1/1999

OTHER PUBLICATIONS

Andrew F. Voter et al., Synthesis of Macrocyclic Polymers Formed via Intramolecular Radical Trap-Assisted Atom Transfer Radical Coupling, ACS Macro Letters, Aug. 3, 2012, pp. 1066-1070, American Chemical Society.

(Continued)

Primary Examiner — Richard A Huhn
(74) Attorney, Agent, or Firm — Hudak, Shunk & Farine Co. LPA

(57) ABSTRACT

New regulator compounds for a novel polymerization process for vinyl monomers, which yields polymers with improved control over composition and nearly full to full conservation of architectural integrity up to high conversion. The regulator compounds are defined by according to anyone of the Formulas 1A, 1B, 1C, 1D, 1E, 1F, 1G, 1H and 1I:

(1A)

(Continued)

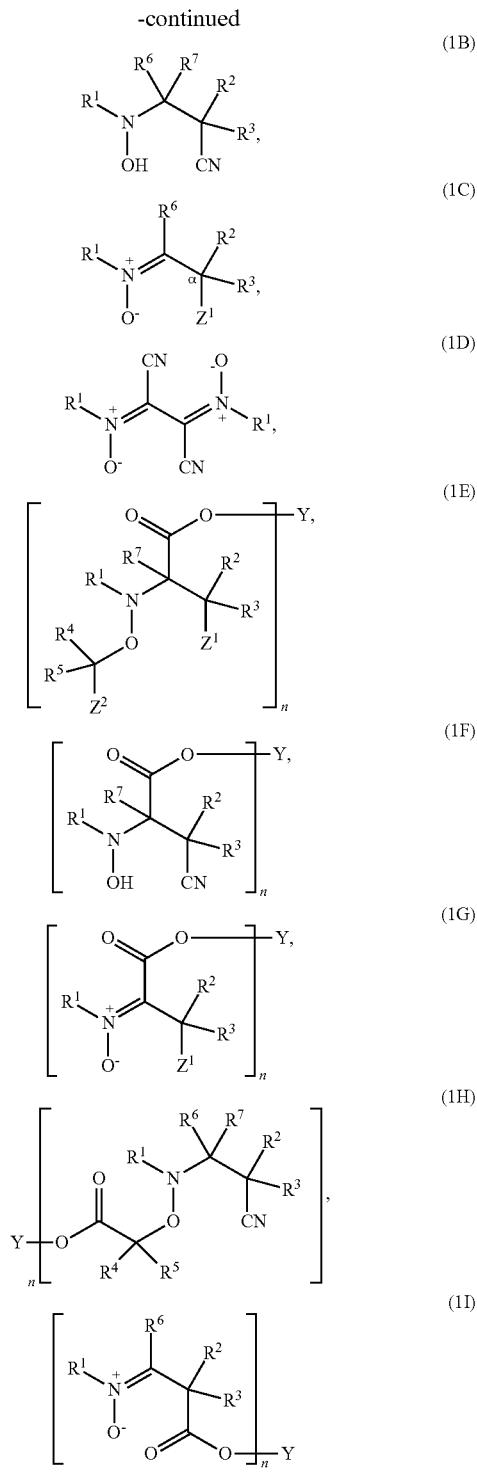

wherein $R^1$ stands for an optionally substituted secondary or tertiary alkyl or secondary or tertiary aralkyl; $Z^1$ stands for —CN or a carboxylic acid ester of formula $C(O)OR^{21}$; $Z^2$ may be chosen from the group of —CN, carboxylic acid, salts of carboxylic acids, carboxylic acid ester, carboxylic acid amides, (hetero)aryl, alkenyl and halogen; $R^2$, $R^3$, $R^4$ and $R^5$ are each independently chosen from the group of H, alkyl, aralkyl, (hetero)aryl, —CN and carboxylic acid ester of formula $C(O)OR^{22}$; $R^7$ stands for a primary alkyl or primary aralkyl, —CN or hydrogen; Y stands for a bridging group and n is 2, 3, 4, 5 or 6; in case $R^1$ stands for tertiary alkyl or tertiary aralkyl, $R^6$ stands for a primary alkyl or primary aralkyl, —CN or a carboxylic acid ester of formula $C(O)OR^{26}$; in case $R^1$ stands for a secondary alkyl or secondary aralkyl, $R^6$ stands for a primary or secondary alkyl or primary or secondary aralkyl, —CN, a carboxylic acid ester of formula $C(O)OR^{26}$ or a phosphonic acid ester of formula $P(O)(OR^{27})_2$, a (hetero)aryl or an alkenyl; $R^{21}$, $R^{22}$, $R^{26}$ and $R^{27}$ each independently stand for alkyl or aralkyl having from 1-30 carbon atoms, optionally containing heteroatoms.

31 Claims, 2 Drawing Sheets

(51) Int. Cl.

| | | |
|---|---|---|
| *C07C 255/03* | (2006.01) | |
| *C08F 2/02* | (2006.01) | |
| *C07C 291/04* | (2006.01) | |
| *C07F 9/40* | (2006.01) | |
| *C07C 255/64* | (2006.01) | |
| *C08F 120/18* | (2006.01) | |
| *C08F 112/08* | (2006.01) | |
| *C08F 120/14* | (2006.01) | |
| *C07C 207/04* | (2006.01) | |
| *C07C 239/18* | (2006.01) | |
| *C07C 239/14* | (2006.01) | |

(52) U.S. Cl.
CPC .......... *C07C 239/16* (2013.01); *C07C 239/18* (2013.01); *C07C 255/03* (2013.01); *C07C 255/64* (2013.01); *C07C 291/04* (2013.01); *C07F 9/4006* (2013.01); *C07F 9/4015* (2013.01); *C08F 2/02* (2013.01); *C08F 112/08* (2013.01); *C08F 120/14* (2013.01); *C08F 120/18* (2013.01); *C07C 2601/14* (2017.05)

(56) References Cited

OTHER PUBLICATIONS

Hans Gunter Aurich, Nitroxides as Reaction Intermediates, Canadian Journal of Chemistry, Jun. 15, 1982, pp. 1414-1420, National Research Council of Canada, Canada.
Didier Benoit et al., Development of a Universal Alkoxyamine for "Living" Free Radical Polymerizations, Journal American Chemical Society, Apr. 28, 1999, pp. 3904-3920, vol. 121, American Chemical Society.
Thanh Binh Nguyen et al., N-Benzyl Aspartate Nitrones: Unprecendented Single-Step Synthesis and [3+2] Cycloaddition Reactions with Alkenes, Organic Letters, Sep. 12, 2008, pp. 4493-4496, vol. 10, No. 20, American Chemical Society.
Khalid B. Selim et al., Organocatalytic enantio- and diastereoselective 1,3-dipolar cycloaddition between alanine-derived ketonitrones and E-crotonaldehyde: efficiency and full stereochemical studies, Tetrahedron: Asymmetry, Nov. 15, 2012, pp. 1670-1677, Elsevier Ltd.
Xiaofei Zhang et al., Asymmetric Synthesis of a, a-Disubstituted Amino Acids by Cycloaddition of (E)-Ketonitrones with Vinyl Ethers, Organic Letters, Mar. 21, 2014, pp. 1936-1939, American Chemical Society.
Mathias Destarac, Controlled Radical Polymerization: Industrial Stakes, Obstacles and Achievements, Macromolecular Reaction Engineering, 2010, pp. 165-179, vol. 4, Wiley InterScience.

(56) References Cited

OTHER PUBLICATIONS

Julien Nicolas et al., Nitroxide-mediated polymerization, Progress in Polymer Science, Jun. 28, 2012, pp. 63-235, Elsevier Ltd.
Paul Knochel et al., Organozinc Reagents, A Practical Approach, Jun. 1998, Appendix A1, Oxford University Press.
Krzysztof Matyjaszewski et al., Simple and Efficient Synthesis of Various Alkoxyamines for Stable Free Radical Polymerization, Macromolecules, Aug. 5, 1998, pp. 5955-5957, vol. 31, American Chemical Society.
Valerie Sciannamea et al., In-Situ Nitroxide-Mediated Radical Polymerization (NMP) Processes: Their Understanding and Optimization, Chem. Rev., Feb. 7, 2008, pp. 1104-1126, vol. 108, American Chemical Society.
Marie-Odile Zink et al., New Alkoxyamines from the Addition of Free Radicals to Nitrones or Nitroso Compounds as Initiators for Living Free Radical Polymerization, Macromolecules, Sep. 19, 2000, pp. 8106-8108, vol. 33, American Chemical Society.
Michiko Iwamura et al., Reactions of Nitrones with Free Radicals. I. Radical 1,3-Addition to Nitrones, Bulletin of the Chemical Society of Japan, Aug. 16, 1969, pp. 856-860, vol. 43.
Anna C. Greene et al., Synthesis and Evaluation of N-Phenylalkoxyamines for Nitroxide-Mediated Polymerization, Macromolecules, Jun. 5, 2009, pp. 4388-4390, vol. 42, American Chemical Society.
Michiko Iwamura et al., Reactions of Nitrones with Free Radicals. II. Formation of Nitroxides, Bulletin of the Chemical Society of Japan, 1970, pp. 860-863, vol. 43.
Ian Patel et al., An Improved Process for the Synthesis and Isolation of (S)-N-(1-Phenylethyl)hydroxylamine, Organic Process Research & Development, Dec. 3, 2008, pp. 49-53, vol. 13, No. 1, American Chemical Society.
Shun-Ichi Murahashi et al., Tungsten-Catalyzed Oxidation of Secondary Amines to Nitrones. a-Substitution of Secondary Amines via Nitrones, Journal Organic Chemistry, 1990, pp. 1736-1744, vol. 55, American Chemical Society.
Robert W. Murray et al., A Facile One-Step Synthesis of C-Arylnitrones Using Dimethyldioxirane, Journal Organic Chemistry, 1990, pp. 2954-2957, vol. 55, American Chemical Society.
Steven W. Baldwin et al., Preparation and Evaluation of a Cyclic Acyl Nitrone as a Synthon for Stereospecific a-Amino Acid Synthesis, Tehrahedron Letters, Jul. 7, 1998, pp. 6819-6822, Elsevier Science Ltd.
Carolina Gella et al., A Metal-Free General Procedure for Oxidation of Secondary Amines to Nitrones, J. Org. Chemistry, Jul. 16, 2009, pp. 6365-6367, vol. 74, American Chemical Society.
D Subhas Bose et al., A Facile Hydration of Nitriles by Dimethyldioxirane, Synthetic Communications, 1997, pp. 3119-3123, vol. 27(18), Marcel Dekker, Inc.
Krzysztof Bujnowski et al., o-Aminomethylderivatives of phenols. Part 3. Mechanistic investigation of a Mannich reaction of phenols with N-methyleneallcylamines, General Papers, 2008, pp. 106-114, ARKAT USA, Inc.
Arthur W. Dox, Tetra-Alkyl-Succinimides and Their Pharmacological Action, Journal American Chemical Society, May 5, 1925, pp. 1471-1477, Journal American Chemical Society.

Lawrence J. Exner et al., a-(N-Alkylamino)-nitriles, Journal American Chemical Society, May 7, 1953, pp. 4841-4842, Journal American Chemical Society.
Terence S. Wilkinson et al., Synthesis and Characterization of a Novel Addition-Fragmentation Reactive Surfactant (TRANSURF) for Use in Free-Radical Emulsion Polymerizations, Journal of Colloid and Interface Science, Jan. 22, 2001, pp. 21-27, Academic Press.
Sadao Mori et al., Size Exclusion Chromatography, Mar. 1999, Springer-Verlag Berlin Heidelberg 1999, Springer.
R.A. Hutchinson et al., Determination of Free-Radical Propagation Rate Coefficients for Alkyl Methacrylates by Pulsed-Laser Polymerization, Macromolecules, Apr. 15, 1997, pp. 3490-3493, vol. 30, American Chemical Society.
Julien Nicolas et al., Novel SG1-Based Water-Soluble Alkoxyamine for Nitroxide-Mediated Controlled Free-Radical Polymerization of Styrene and n-Butyl Acrylate in Miniemulsion, Macromolecules, Apr. 20, 2004, pp. 4453-4463, vol. 37, American Chemical Society.
P. G. Santangelo et al., Dynamics near the Glass Temperature of Low Molecular Weight Cyclic Polystyrene, Macromolecules, Nov. 22, 2001, pp. 9002-9005, vol. 34, American Chemical Society.
J. Anthony Semlyen, Cyclic Polymers, 2000, pp. 347-384, Kluwer Academic Publishers, Dordrecht/Boston/London.
Jean Ruehl et al., Cyclic Alkoxyamines for Nitroxide-Mediated Radical Polymerization, Journal of Polymer Science, Sep. 26, 2008, pp. 8049-8069, vol. 46, Wiley Periodicals, Inc.
Atsushi Narumi et al., Cyclic Alkoxyamine-Initiator Tethered by Azide/Alkyne-"Click"-Chemistry Enabling Ring-Expansion Vinyl Polymerization Providing Macrocyclic Polymers, Journal of Polymer Science, May 10, 2010, pp. 3402-3416, vol. 48, Wiley Periodicals, Inc.
Renaud Nicolay et al., Synthesis of Cyclic (Co)polymers by Atom Transfer Radical Cross-Coupling and Ring Expansion by Nitroxide-Mediated Polymerization, Macromolecules, Dec. 23, 2010, pp. 240-247, vol. 44, American Chemical Society.
Zhongfan Jia et al., Cyclic Polymers: Methods and Strategies, Journal of Polymer Science, Feb. 28, 2012, pp. 2085-2097, vol. 50, Wiley Periodicals, Inc.
Yohann Guillaneuf et al., First Effective Nitroxide-Medicated Polymerization of Methyl Methacrylate, Macromolecules, Apr. 11, 2007, pp. 3108-3114, vol. 40, American Chemical Society.
Anna C. Greene et al., Nitroxide-Mediated Polymerization of Methyl Methacrylate and Styrene with New Alkoxyamines from 4-Nitrophenyl 2-Methylpropionat-2-yl Radicals, Macromolecules, Nov. 19, 2010, pp. 10320-10325, vol. 43, American Chemical Society.
Christophe Detrembleur et al., Nitroxide Mediated Polymerization of Methacrylates at Moderate Temperature, Polymer Chemistry, Sep. 17, 2013, pp. 335-340, vol. 5, The Royal Society of Chemistry.
Bernadette Charleux et al., Theoretical Expression of the Average Activation-Deactivation Equilibrium Constant in Controlled/Living Free-Radical Copolymerization Operating via Reversible Termination. Application to a Strongly Improved Control in Nitroxide-Mediated Polymerization of Methyl Methacrylate, Macromolecules, Jun. 1, 2005, pp. 5485-5492, vol. 38, American Chemical Society.
Graeme Moad et al., The Chemistry of Radical Polymerization, Second Edition, 2006, pp. 321-322, Elsevier.

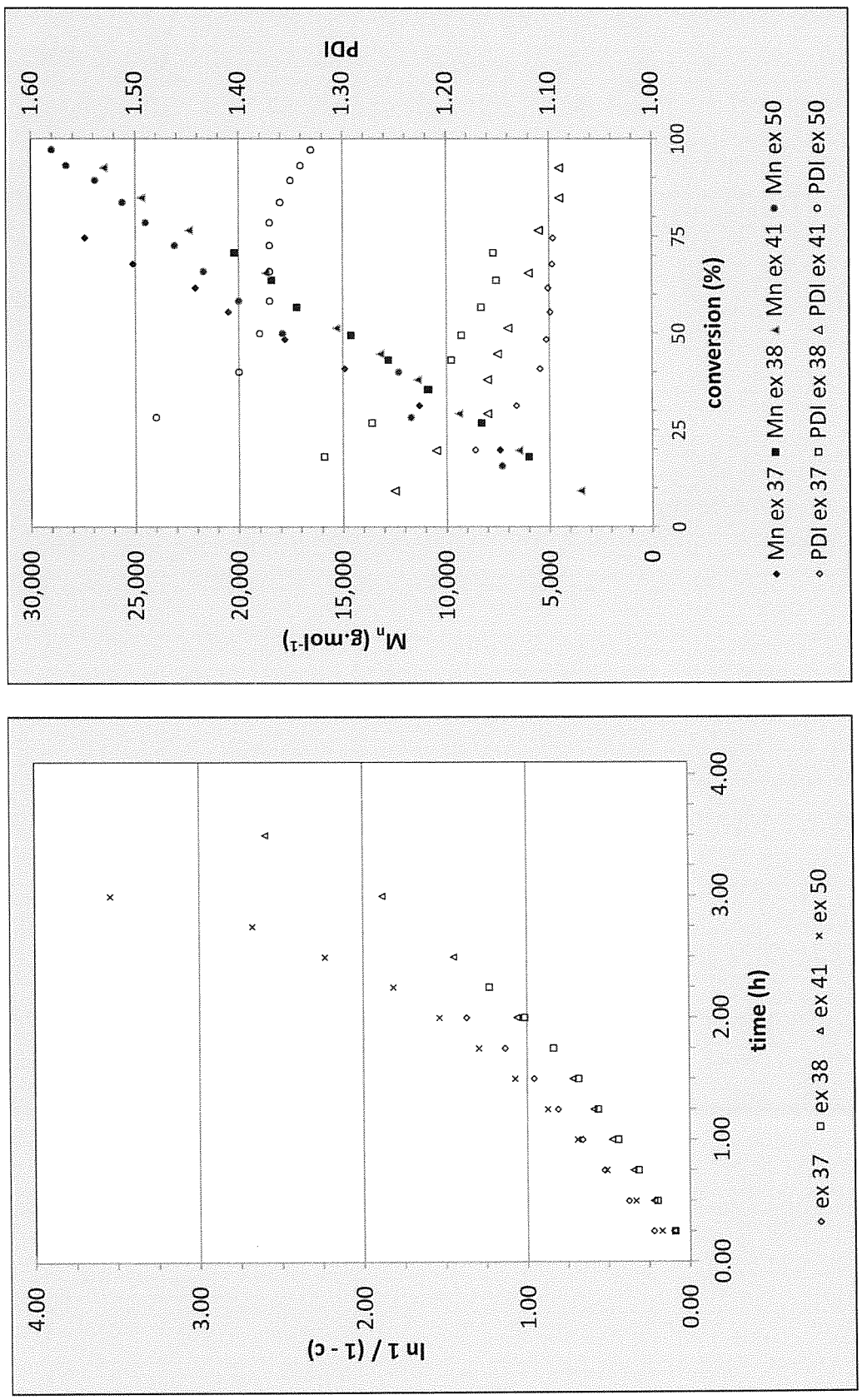
Fig. 1 Controlled Ring Expansion Polymerization of Styrene

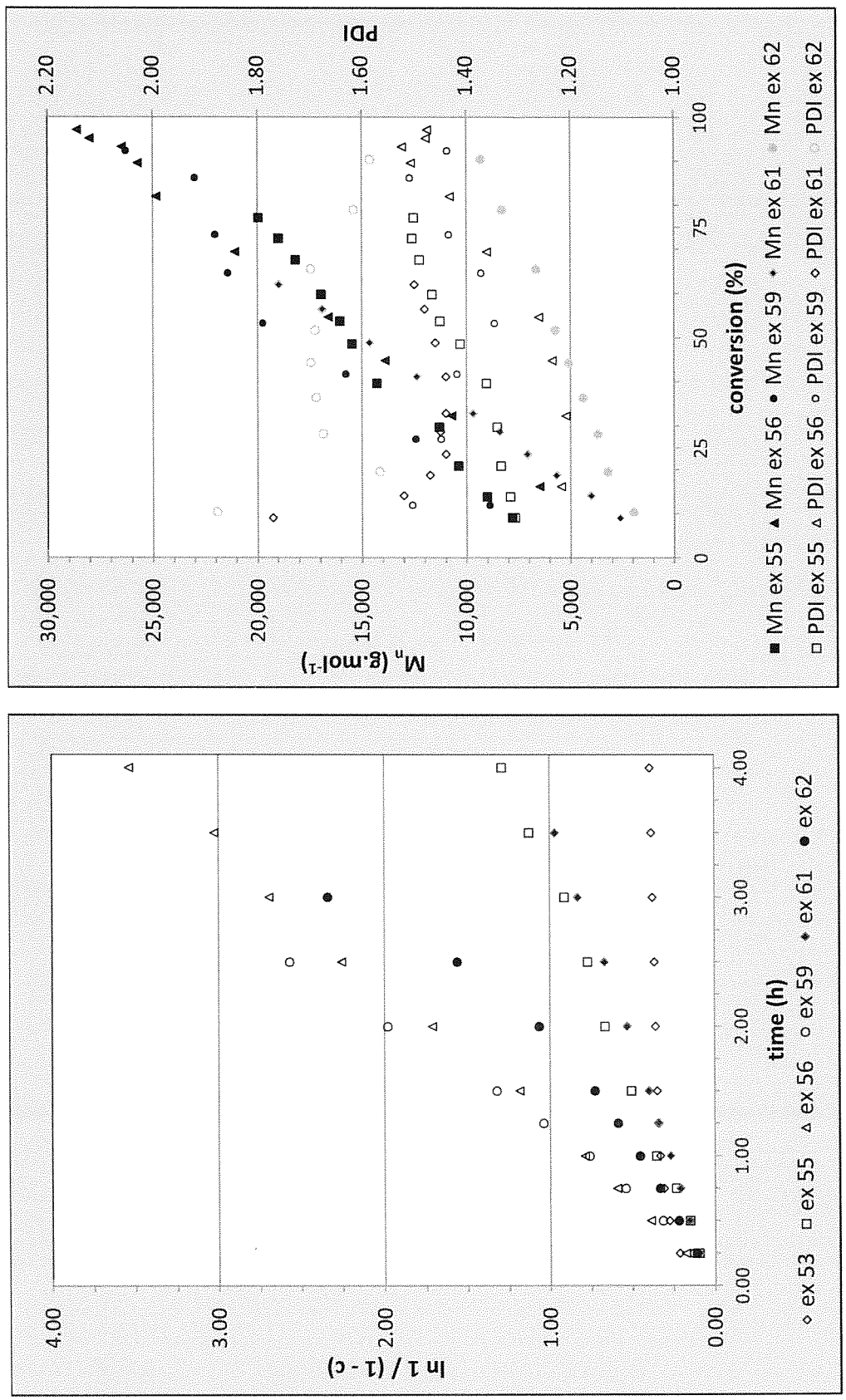
Fig. 2 Linear Nitroxide-Mediated Polymerization and Controlled Ring Expansion Polymerization of Methacrylics

REGULATORS FOR CONTROLLING LINEAR AND PSEUDO-RING EXPANSION POLYMERIZATION OF VINYL MONOMERS

FIELD OF THE INVENTION

The invention relates to a process for the polymerization of vinyl monomers using regulator compounds, to linear and cyclic polymers obtainable by said process, to a process for the preparation of the regulator compounds, to novel regulator compounds, to the preparation of the regulator compounds and to the use of the regulator compounds in the polymerization of vinyl monomers.

BACKGROUND OF THE INVENTION

Free radical polymerization is by far the most important technology for polymerization of vinyl monomers, as it combines a broad scope, for example, in the choice of monomer, including functional ones, tolerance to water and protic solvent, etc., with relative ease of industrialization. Obtaining vinyl polymers with control over polymer architecture (block, star, hyper-branched, etc.) has not been feasible in classical free radical polymerization.

Until the Mid-90s architectural control in vinyl polymers could only be achieved by living ionic polymerization technologies. While such polymers showed great promise in terms of superior performance in various end-use applications, limitations in the choice of monomer and higher cost as a result of stringent process conditions needed for their production have restricted their scope of industrialization.

Since the Mid-90s Controlled Radical Polymerization (CRP) has emerged as the promising alternative, as CRP can overcome some of the limitations of living ionic polymerization: stringent process conditions are no longer required and versatility in terms of monomer type is greatly expanded. Polymer architecture can now be engineered on a macromolecular level by controlled free radical polymerization.

Several processes are available for effecting CRP. From the perspective of industrial implementation the three most prominent technologies are:

Nitroxide-Mediated Polymerization (NMP), wherein nitroxides reversibly deactivate polymer radicals by forming alkoxyamines;

Atom Transfer Radical Polymerization (ATRP), wherein metal salt complexes reversibly deactivate polymer radicals by (halogen) atom transfer; and Reversible Addition-Fragmentation chain Transfer (RAFT), wherein dithiocarbonyl- and related compounds reversibly deactivate polymer radicals by degenerative transfer.

Tremendous progress has been made in developing the scope of CRP in view of its potential for producing medium-to-high-end specialty polymer, but the current scale of industrialization is far from what has been predicted. The key issue is how to produce polymer with control over architecture under realistic process conditions from a technical-economic perspective (Destarac, M. *Macromol. React. Eng.* 2010, 4, 165-179).

Manufacturers typically produce specialty vinyl polymer in a multi-purpose batch plant. Most often, industrial batch radical polymerization is operated "semi-continuously", i.e., continuously feeding the major part or most of the monomers during a first stage (amongst others, to control exothermicity of the process) and then allowing most free monomer still left to react in the second stage. When vinyl polymer with control over architecture is to be produced industrially by a CRP process, it is thus in direct competition for occupancy with a range of other specialty vinyl polymer already supplied by a manufacturer, but then produced by classical radical polymerization.

While increases in cost of raw material and/or transformation may be economically justifiable by a higher sales price, the production of vinyl polymer with control over architecture needs to conform technically to the plant's practice. High conversion in CRP needs to be attained in acceptable batch times, i.e., in practice not that different from other products produced. Once polymerization is finished, polymer must be ready-to-use or ready-to-formulate: extensive cleaning operations are prohibitive. Batch-to-batch consistency and reproducibility need to be excellent.

Also, regulators for controlling the polymerization process must be available at an affordable price from multiple sources (no single supplier issues). While regulators have been developed to achieve high conversion in acceptable batch times, at present their cost and availability are still issues for all CRP technologies.

The need for post-polymerization modification to remove labile end groups (for ATRP and RAFT) and to introduce acid groups (specifically for ATRP), as well as washing and cleaning operations (to remove metal salt catalyst complex and fragments formed during end group transformation) make ATRP and RAFT less attractive. As NMP does not require these additional process steps, it is in this respect better suited to be adapted to the existing practice of a multi-purpose batch plant operated in industrial radical polymerization.

In the CRP processes known to date, some termination cannot be avoided especially at high conversion, which is therefore achieved at a variable loss in end group fidelity and architectural integrity: how tolerant end-use performance is to these intrinsic variations in batch-to-batch consistency and reproducibility is a key issue. This is aggravated as in industry CRP is to be run semi-continuously at higher instantaneous conversions. Improving conservation of end group fidelity and architectural integrity by working in monomer-flooded conditions and halting polymerization at a lower final conversion with subsequent monomer removal and recycling is no option in a multi-purpose batch plant setting.

In this respect, living ionic polymerization does have a clear advantage over CRP, as precise control allows for architectural integrity to be conserved up to high conversion. Thus, it would be desirable to design a next generation regulator compound, preferably of the alkoxyamine type, by which architectural integrity can equally well be conserved up to high conversion as in a living ionic polymerization, while at the same time overcoming the latter's limitations.

SUMMARY OF THE INVENTION

The objective of the present invention is to provide regulator compounds for a novel polymerization process for vinyl monomers, which yields polymers with nearly full to full conservation of architectural integrity up to high conversion and improved control over composition.

In order to unequivocally display the novelty of the invention the ability to control architecture and composition of the polymer so produced will be demonstrated in two ways: conservation of architectural integrity during polymerization to yield well-defined cyclic polymer, a combination of process and architecture, which no CRP or living ionic vinyl polymerization technology has yet been able to master (or is ever likely to be able to); and, with regards to composition, controlling homopolymerization of methacrylic monomer, a type of composition that has eluded most alkoxyamines of prior art.

The process for producing said polymers preferably is fully compatible with industrial practice and polymers so produced preferably are ready-to-use or ready-to-formulate. The alkoxyamine regulator to be employed herein is either to be added as such or, else, to be quantitatively generated in situ from a suitable precursor at the start of the process. Preferably, the regulator (precursor) is made efficiently from readily available and cheap raw materials. Easy production from affordable chemicals supports the production of vinyl polymer with controlled architecture and composition and facilitates the exploitation of the full potential of these novel polymers in end-use applications.

The objective is achieved by regulator compounds suitable for the polymerization of vinyl monomers wherein the regulator compounds are according to anyone of the Formulas 1A, 1B, 1C, 1D, 1E, 1F, 1G, 1H and 1I:

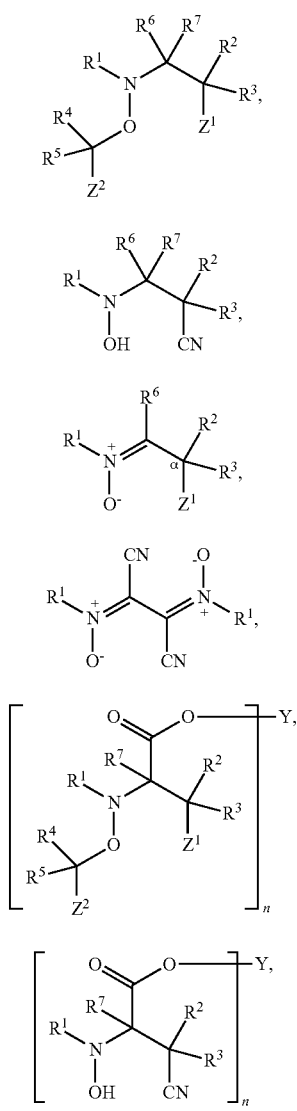

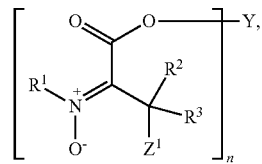

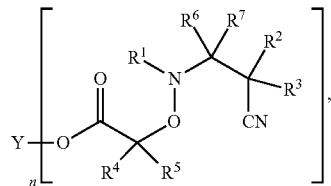

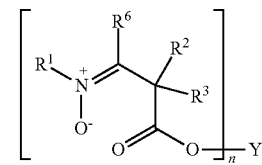

wherein
$R^1$ stands for an optionally substituted secondary or tertiary alkyl or secondary or tertiary aralkyl;
$Z^1$ stands for —CN or a carboxylic acid ester of formula $C(O)OR^{21}$;
$Z^2$ may be chosen from the group of —CN, carboxylic acid, salts of carboxylic acid, carboxylic acid ester, carboxylic acid amide, (hetero)aryl, alkenyl and halogen;
$R^2$, $R^3$, $R^4$ and $R^5$ are each independently chosen from the group of H, alkyl, aralkyl, (hetero)aryl, —CN and carboxylic acid ester of formula $C(O)OR^{22}$;
$R^7$ stands for a primary alkyl or primary aralkyl, —CN or hydrogen;
Y stands for a bridging group and n is 2, 3, 4, 5 or 6;
in case $R^1$ stands for tertiary alkyl or tertiary aralkyl, $R^6$ stands for a primary alkyl or primary aralkyl, —CN or a carboxylic acid ester of formula $C(O)OR^{26}$;
in case $R^1$ stands for a secondary alkyl or secondary aralkyl, $R^6$ stands for a primary or secondary alkyl or primary or secondary aralkyl, —CN, a carboxylic acid ester of formula $C(O)OR^{26}$ or a phosphonic acid ester of formula $P(O)(OR^{27})_2$, a (hetero)aryl or an alkenyl;
$R^{21}$, $R^{22}$, $R^{26}$ and $R^{27}$ each independently stand for alkyl or aralkyl having from 1-30 carbon atoms, optionally containing heteroatoms.

An alkyl group can have a linear, branched or cyclic structure.

An aralkyl group is a univalent radical derived from an alkyl radical by replacing one or more hydrogen atoms by aryl groups.

A (hetero)aryl group is an aryl having an aromatic ring structure, which can contain one or more heteroatoms (O, S, N). Examples of (hetero)aryl groups are phenyl, 1-naphthyl and 2-naphthyl, 2-furyl, 1-imidazolyl, 2-indolyl, 2-pyridyl, 1-pyrrolyl, and 3-thienyl.

All major present limitations in industrializing the production of vinyl polymer with control over architecture and composition are solved by applying compounds of Formulas (1A) to (1I) (hereinafter together defined as compounds of Formula (1)) as regulators:

regulators of Formula (1) are able to control vinyl polymerization up to high conversion in commercially acceptable batch times;

as evidenced by the first successful preparations of well-defined cyclic vinyl polymer, high conversion is achieved with full conservation of architectural integrity: batch-to-batch consistency and reproducibility are thus excellent;

regulators of Formula (1) are able to control the homopolymerization of methacrylic monomer, which until now has only been achieved by using alkoxyamines of prohibitive cost in a process that yields colored polymer product;

polymer so obtained is ready-to-use or ready-to-formulate;

regulators of Formula (1) are accessible from cheap and readily available raw materials.

Additional Advantages

Successful preparation of cyclic vinyl polymer clearly distinguishes the mechanism of the process, by which regulator compounds of Formula (1) control polymerization, from that of NMP and other CRP technologies known to date. Without being bound by any theory, for the purpose of the patent the process will be named Pseudo-Ring Expansion Polymerization (P-REP), where it concerns preparation of cyclic vinyl polymer.

Compared to previous CRP, operational freedom in executing a vinyl polymerization for producing polymer with controlled composition and architecture is greatly expanded by using the regulators of Formula (1). E.g., in order to minimize batch time running a vinyl polymerization semi-continuously at high instantaneous conversion is now feasible by proper choice of reaction temperature, because end group fidelity and architectural integrity are secure.

Also, in preparing block copolymer introduction of second-stage monomer need only start when first-stage monomer is nearly completely consumed, maximizing homogeneity of the constituent blocks. By contrast, for CRP in order to conserve end group fidelity introduction of second-stage monomer is in practice commenced at a lower final conversion of first-stage monomer, resulting in significant tapering, i.e., a zone of mixed composition that can act as a compatibilizer and adversely affect performance in end-use application.

Production of vinyl polymer with control over architecture using regulator compounds of Formula (1) shares these advantages with living ionic polymerization, while at the same time it overcomes the latter's limitations. Extensive purification of monomer and solvent, rigorous exclusion of water and other protic sources, low reaction temperatures, etc., customary for ionic polymerization, are not needed, while a wider variety of monomers, including functional ones, and solvents, including protic solvents and water, can now be used as well.

As propagation occurs by a mechanism distinct from that of conventional- and previous controlled free radical polymerization, the stereochemistry of a polymer so produced will differ. Thus, use of regulators of Formula (1) for controlling vinyl polymerization offers the added opportunity to capitalize on advantageous material properties resulting from differences in polymer microstructure, such as, e.g., changes in selectivity when polymerizing 1,3-dienes (e.g., butadiene, isoprene, etc.) and tacticity enrichment, as exemplified herein.

Until now, cyclic vinyl polymer has not been commercially exploited because of a prohibitive cost of production. A cost-effective preparation is now available: use of cyclic alkoxyamine regulators of Formula (1A) (generated in situ from other regulators of Formula (1) described herein) yields well-defined cyclic vinyl polymer directly in a controlled Pseudo-Ring Expansion Polymerization (P-REP) process. Selected regulator compounds of Formula (1) can now be used to implement cyclic vinyl polymer industrially and capitalize on advantageous properties of this class of polymer in end-use applications.

Regulator Compounds of Formula (1).

The regulator compounds have a core structure represented by general Formula (1J):

(1J)

which can contain different substituents on the main chain.

The regulator compounds are defined according to anyone of the Formulas 1A, 1B, 1C, 1D, 1E, 1F, 1G, 1H and 1I:

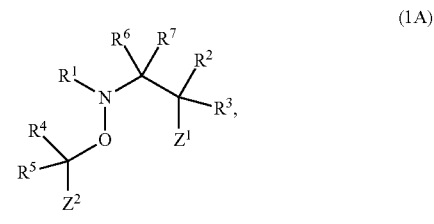

(1A)

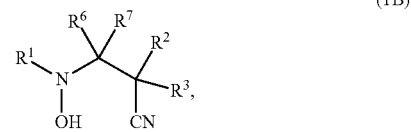

(1B)

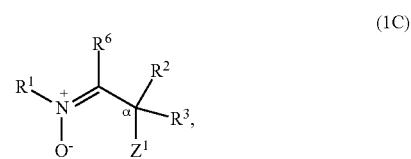

(1C)

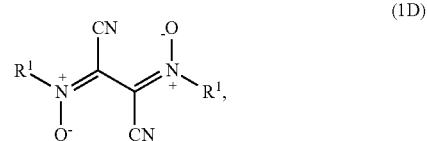

(1D)

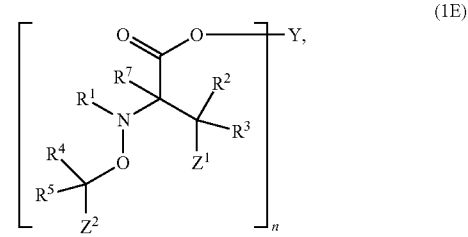

(1E)

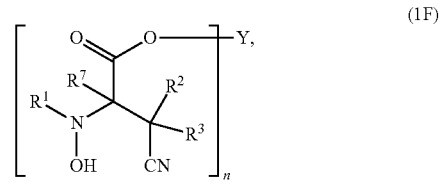

(1F)

-continued

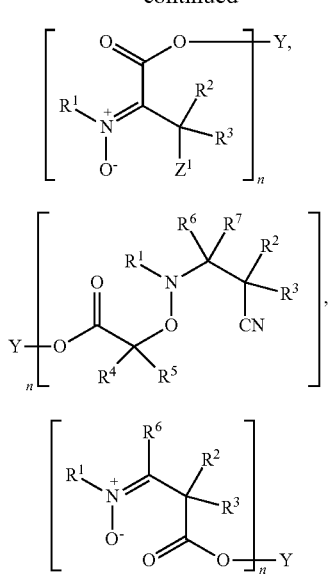

wherein
$R^1$ stands for an optionally substituted secondary or tertiary alkyl or secondary or tertiary aralkyl;
$Z^1$ stands for —CN or a carboxylic acid ester of formula $C(O)OR^{21}$;
$Z^2$ may be chosen from the group of —CN, carboxylic acid, salts of carboxylic acid, carboxylic acid ester, carboxylic acid amide, (hetero)aryl, alkenyl and halogen;
$R^2$, $R^3$, $R^4$ and $R^5$ are each independently chosen from the group of H, alkyl, aralkyl, (hetero)aryl, —CN and carboxylic acid ester of formula $C(O)OR^{22}$;
$R^7$ stands for a primary alkyl or primary aralkyl, —CN or hydrogen;
Y stands for a bridging group and n is 2, 3, 4, 5 or 6;
in case $R^1$ stands for tertiary alkyl or tertiary aralkyl, $R^6$ stands for a primary alkyl or primary aralkyl, —CN or a carboxylic acid ester of formula $C(O)OR^{26}$;
in case $R^1$ stands for a secondary alkyl or secondary aralkyl, $R^6$ stands for a primary or secondary alkyl or primary or secondary aralkyl, —CN, a carboxylic acid ester of formula $C(O)OR^{26}$ or a phosphonic acid ester of formula $P(O)(OR^{27})_2$, a (hetero)aryl or an alkenyl;
$R^{21}$, $R^{22}$, $R^{26}$ and $R^{27}$ each independently stand for alkyl or aralkyl having from 1-30 carbon atoms, optionally containing heteroatoms.

Examples of $R^1$ include secondary and tertiary alkyl and secondary or tertiary aralkyl groups typically comprising from 3 to 100 C-atoms, such as, e.g., isopropyl, sec-butyl, tert-butyl, 3-pentyl, tert-amyl, cyclohexyl, 2,4-dimethyl-3-pentyl, 2,2,4-trimethyl-3-pentyl and 1-adamantyl; 1-phenylethyl, 2-methyl-1-phenyl-1-propyl and diphenylmethyl. The alkyl and aralkyl groups can contain polar substituents, like —CN, carboxylic acid ester, phosphonate ester and hydroxy. Examples of such groups are 1-cyanocyclohexyl, 1-(methoxycarbonyl)-2-methyl-1-propyl, 1-(diethoxyphosphoryl)-2,2-dimethylpropyl, 1-hydroxy-2-methyl-2-propyl and 1,3-dihydroxy-2-(hydroxymethyl)-2-propyl.

In a preferred embodiment $R^1$ is chosen from the group consisting of tert-butyl, cyclohexyl, 2-methyl-1-phenyl-1-propyl, more preferably from the group consisting of tert-butyl and cyclohexyl.

Examples of $Z^1$ include —CN and a carboxylic acid ester of formula $C(O)OR^{21}$.
Preferably $Z^1$ stands for —CN or $C(O)OMe$, more preferably $Z^1$ stands for —CN.
Preferably, $R^2$, $R^4$ and $R^5$ are each independently chosen from the group of H, alkyl having from 1-30 C-atoms, and (hetero)aryl having from 4-30 C-atoms.
In a preferred embodiment $R^2$, $R^4$ and $R^5$ are each independently chosen from H, methyl and ethyl.
$R^3$ can be H, alkyl having from 1-30 C-atoms, (hetero)aryl having from 4-30 C-atoms, —CN or a carboxylic acid ester of formula $C(O)OR^{23}$.
$R^3$ is preferably H, methyl, ethyl, —CN, $C(O)OMe$ or $C(O)OEt$.
In case $R^1$ stands for a tertiary alkyl or tertiary aralkyl (preferably tert-butyl), $R^6$ stands for a primary alkyl having from 1-18 C-atoms, a primary aralkyl having from 7-18 C-atoms, —CN or a carboxylic acid ester of formula $C(O)OR^{26}$.
Examples of $R^6$ as a primary alkyl or primary aralkyl include methyl, ethyl, 1-propyl, isobutyl, 2-ethylbutyl, 2-ethylhexyl, benzyl and 2-phenylethyl.
Preferably $R^6$ is —CN, $C(O)OMe$, $C(O)OEt$ or methyl.
In case $R^1$ stands for a secondary alkyl or secondary aralkyl (preferably cyclohexyl), $R^6$ stands for a primary or secondary alkyl having from 1-30 C-atoms, a primary or secondary aralkyl having from 7-18 C-atoms, —CN, a carboxylic acid ester of formula $C(O)OR^{26}$ or a phosphonic acid ester of formula $P(O)(OR^{27})_2$, a (hetero)-aryl or an alkenyl.
Examples of $R^6$ as primary alkyl or primary aralkyl include methyl, ethyl, 1-propyl, isobutyl, 2-ethylbutyl, 2-ethylhexyl, benzyl and 2-phenylethyl.
Examples of $R^6$ as secondary alkyl or secondary aralkyl include isopropyl, cyclohexyl and 1-phenylethyl.
Examples of $R^6$ as (hetero)aryl include phenyl, 2-furyl and 2-pyridyl.
Examples of $R^6$ as alkenyl include ethenyl (vinyl), 1-methylethenyl (isopropenyl), 2-phenylethen-1-yl, 1-propen-1-yl and 2-methyl-1-propen-1-yl.
Preferably $R^6$ is —CN, phenyl, $C(O)OMe$, $C(O)OEt$, $P(O)(OEt)_2$ or an isopropyl group.
In the compounds mentioned herein, $R^7$ stands for a primary alkyl or primary aralkyl, —CN or hydrogen.
Examples of $R^7$ as primary alkyl or primary aralkyl include methyl, ethyl, 1-propyl, isobutyl, 2-ethylbutyl, 2-ethylhexyl, benzyl and 2-phenylethyl.
Preferably, $R^7$ is hydrogen or methyl.
$Z^2$ may stand for —CN, a carboxylic acid ester of formula $C(O)OR^{22}$, a carboxylic acid or its salt, a carboxylic acid amide, a (hetero)aryl, an alkenyl or a halogen.
Examples of a (hetero)aryl include phenyl, 2-furyl and 2-pyridyl.
Examples of an alkenyl include ethenyl (vinyl), 1-methylethenyl (isopropenyl), 2-phenylethen-1-yl, 1-propen-1-yl, and 2-methyl-1-propen-1-yl.
Preferably, $Z^2$ is selected from the group of —CN, Ph, $C(O)OMe$, $C(O)OEt$ or $C(O)OH$, more preferably $Z^2$ is —CN.
Examples of $R^{21}$, $R^{22}$, $R^{23}$, $R^{26}$ and $R^{27}$ include methyl, ethyl, n-butyl, tert-butyl, benzyl, cyclohexyl, 2-hydroxyethyl, 2-methoxyethyl, 2-acetoacetoxyethyl and 2,3-epoxypropyl.
In a preferred embodiment $R^{21}$ is methyl.
In a preferred embodiment $R^{22}$ is chosen from methyl, ethyl and cyclohexyl.

In a preferred embodiment $R^{23}$ is chosen from methyl and ethyl.

In a preferred embodiment $R^{26}$ is chosen from methyl, benzyl and tert-butyl.

In a preferred embodiment $R^{27}$ is chosen from ethyl and n-butyl.

One or more rings may be present in the regulator compound between $R^1$ and $R^4$ or $R^5$, and/or between $R^2$ and $R^3$, and/or between $R^4$ and $R^5$, and/or between $R^7$ and $R^4$ or $R^5$, and/or between R' and $R^6$ or $R^7$ (in the latter case with a minimum ring size of 6). Such a ring may be present in the regulator compound itself, e.g., when $R^2$-$R^3$ and/or $R^4$-$R^5$ equals $(CH_2)_5$, in which case the ring remains unaltered. Alternatively, a ring may be generated in situ at the onset of the polymerization between $R^1$ and $R^4$ or $R^5$ or, alternatively, between $R^7$ and $R^4$ or $R^5$, in which case the ring enlarges by monomer insertion, such as is the case for a cyclic mono-alkoxyamine oligomer of Formula (1A) formed in situ at the start of pseudo-ring expansion polymerization, wherein in the case of styrene polymerization $R^7$ and $R^4$ are each a (primary) $CH_2$ linked into a ring by a $CHPh(CH_2CHPh)_m$ chain (wherein m can be between 1 and 100.000).

A number of n independent units of general Formula (1J) may be linked into one molecule by a bridging substituent Y as in the multifunctional compounds of Formulas (1E), (1F), (1G), (1H) and (1I), wherein $R^1$, $R^2$, $R^3$, $R^4$, $R^5$, $R^6$, $R^7$, $Z^1$ and $Z^2$ are as defined above.

Examples of Y include, but are not limited to: 1,2-ethanediyl, 2,2-dimethyl-1,3-propanediyl, 1,4-butanediyl and 1,6-hexanediyl (n=2), as well as pentaerythrityl (n up to 4) and dipentaerythrityl (n up to 6).

A special case incorporating 2 overlapping units of general Formula (1J) is represented by difunctional compounds of Formula (1D), wherein $R^1$ is as defined above.

Preferred compounds of Formula (1A) include:

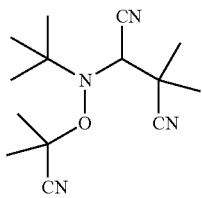
(1A-1)

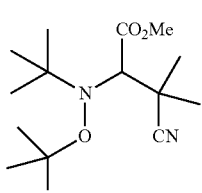
(1A-2)

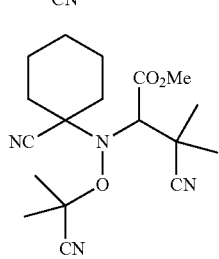
(1A-3)

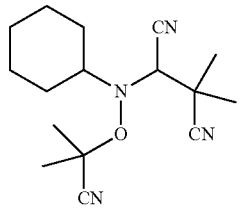
(1A-4)

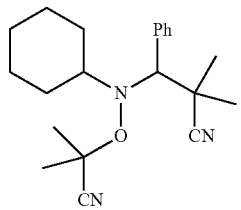
(1A-5)

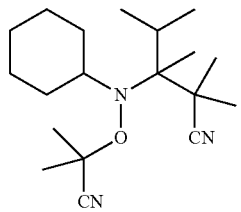
(1A-6)

Preferred compounds of Formula (1B) include:

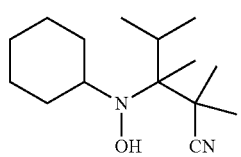
(1B-1)

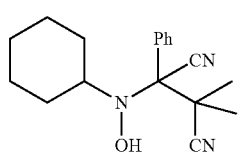
(1B-2)

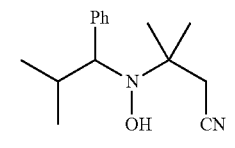
(1B-3)

Preferred compounds of Formula (1C) include:

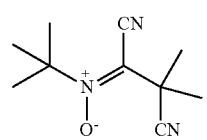
(1C-1)

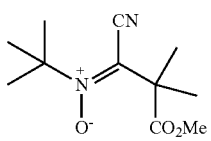
(1C-2)

(1C-3)

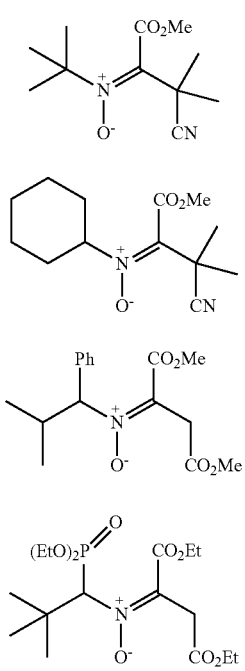

(1C-4)

(1C-5)

(1C-6)

Preferred compounds of Formula (1D) include:

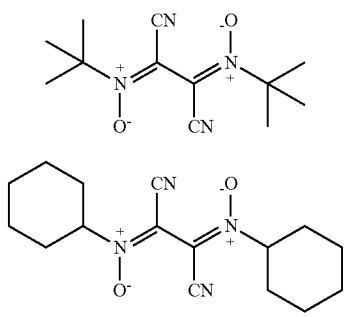

(1D-1)

(1D-2)

Preferred compounds of Formulas (1E), (1F), (1G), (1H) and (1I) include:

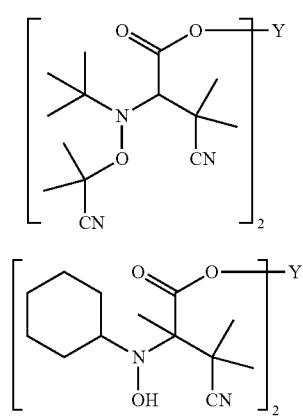

(1E-1)

(1F-1)

(1G-1)

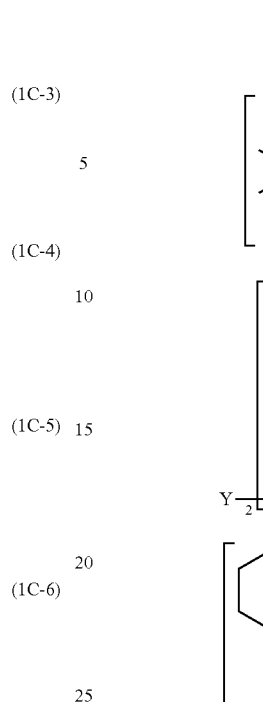

(1H-1)

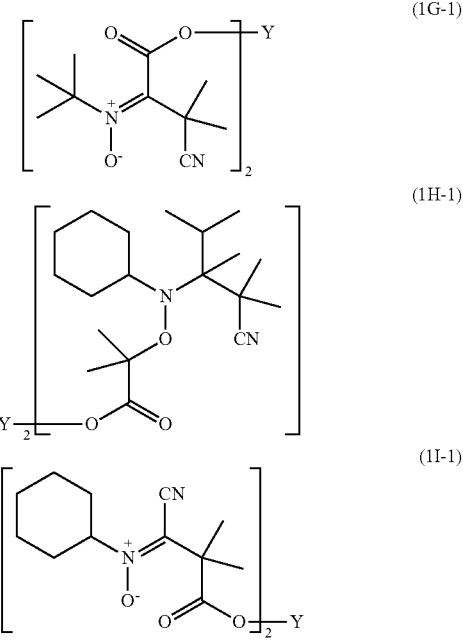

(1I-1)

wherein Y equals 1,2-ethanediyl.

The invention also relates to a method of polymerization of vinyl monomers with anyone of the regulators as defined above to arrive at novel polymers.

Vinyl Monomers

Vinyl monomers used in the preparation of polymer according to the invention are preferably selected from the group of 1-substituted vinyl monomer represented by Formula (2):

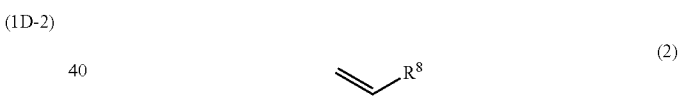

(2)

wherein $R^8$ stands for an optionally substituted (hetero)aryl or alkenyl, halogen, —CN, carboxylic acid, a salt of carboxylic acid, carboxylic acid ester or carboxylic acid amide, or from the group of 1,1-disubstituted vinyl monomer represented by Formula (3):

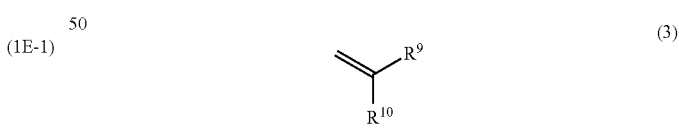

(3)

wherein in case $R^9$ stands for an optionally substituted (hetero)aryl or alkenyl, —CN, carboxylic acid, a salt of carboxylic acid, carboxylic acid ester or carboxylic acid amide, $R^{10}$ stands for an alkyl, most preferably a methyl, or wherein in case $R^9$ stands for halogen, $R^{10}$ also stands for halogen or for an optionally substituted alkenyl.

The vinyl monomers can be mixtures selected from the group of 1-substituted vinyl monomer of Formula (2) and/or from the group of 1,1-disubstituted vinyl monomer of Formula (3), optionally in combination with vinyl comonomer selected from the group of 1,2-disubstituted vinyl monomer represented by Formula (4):

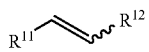
(4)

wherein in case $R^{12}$ stands for an optionally substituted (hetero)aryl, —CN or carboxylic acid, including its salts, esters and amides, $R^{11}$ stands for an optionally substituted (hetero)aryl, —CN, carboxylic acid, including its salts, esters and amides, or alkyl, and wherein $R^{11}$ and $R^{12}$ may optionally form a ring.

Examples of 1-substituted vinyl monomers of Formula (2) include but are not limited to: styrene (S), butadiene, isoprene, acrylonitrile, acrylic acid and acrylic acid esters, such as butyl acrylate and 2-ethylhexyl acrylate as preferred monomers.

Examples of 1,1-disubstituted vinyl monomers of Formula (3) include but are not limited to: methacrylic acid and methacrylic acid esters, more preferably methacrylic acid, methyl methacrylate (MMA), ethyl methacrylate (EMA) and butyl methacrylate (BMA), and others such as methacrylonitrile and α-methylstyrene.

Examples of halogenated 1,1-disubstituted vinyl monomer of Formula (3) include but are not limited to: vinylidene fluoride, vinylidene chloride and chloroprene.

Examples of 1-substituted vinyl monomers of Formula (2) and 1,1-disubstituted vinyl monomers of Formula (3) that contain a reactive group include but are not limited to: 2-hydroxyethyl acrylate, 2-hydroxyethyl methacrylate, glycidyl methacrylate and acetoacetoxyethyl methacrylate.

Examples of 1,2-disubstituted vinyl monomer of Formula (4) include but are not limited to: maleic- and fumaric acid including their (hemi)esters and -amides, such as dimethyl maleate and dimethyl fumarate, maleonitrile and fumaronitrile, crotonic- and cinnamic acid including their esters and amides, crotononitrile, cinnamonitrile, and stilbene.

Examples of 1,2-disubstituted vinyl monomer of Formula (4), wherein $R^{11}$ and $R^{12}$ form a ring, include but are not limited to: maleic anhydride and maleimide, including its N-substituted derivates such as, e.g., N-methylmaleimide.

Preferred monomers include styrene (S), isoprene (I), butadiene (B), acrylic acid (AA), butyl acrylate (BA), 2-ethyhexyl acrylate (EHA), methacrylic acid (MAA), methyl methacrylate (MMA) and maleic anhydride (MA).

Polymerization Using Regulators of Formula (1)

Regulator compounds of Formula (1) are particularly suited for controlling polymerization of 1-substituted vinyl monomers of Formula (2) and 1,1-disubstituted vinyl monomers of Formula (3), optionally in combination with 1,2-disubstituted vinyl comonomers of Formula (4). The new polymerization process of the invention is distinctly different from that of NMP and other CRP technologies of prior art: as is demonstrated herein by the first successful preparation of cyclic vinyl polymer in a pseudo-ring expansion polymerization (P-REP) process, termination must be effectively suppressed.

Suppression of termination is particularly advantageous to the skilled person, as it will allow him to design conditions, such that the process for production of specialty vinyl polymer with control over architecture is now easily implemented in existing industrial radical polymerization equipment. It will allow him to conduct the process with the highest efficiency, i.e. by feeding all (or most of the) monomer at such rate that high instantaneous conversions are achieved in the shortest batch time feasible, whilst maintaining full control over architecture and composition throughout the process.

In this respect, the lower temperature limit for running the polymerization process is then principally governed by the substituent pattern in the regulator compound of Formula (1). In principle, the choice of temperature does not present a limitation as to the choice of monomer, except where the ceiling temperature of the polymer produced may become a concern. In practice, the polymerization temperature need not exceed a preferred range of 130 to 160° C. in order to achieve high instantaneous conversion in the shortest batch time for the less active regulators of Formula (1), whereas for the more active regulators this range is between 80-140° C. Pressure may have to be applied, when reaction temperature exceeds that of the boiling point of the monomer and/or of the medium used (solvent or continuous phase in a dispersion process).

The polymerization processes may be performed in a solvent or without a solvent (in which case vinyl monomer functions essentially as the solvent). Examples of solvents include aromatic solvents, such as, e.g., toluene and xylene, or esters, such as, e.g., butyl acetate, or ethers, such as, e.g., dioxane. Alternatively, the polymerization may be conducted as a dispersion (emulsion, miniemulsion, microemulsion, suspension), most notably in water, as a more environmentally benign process (than solution polymerization). For (highly) water-soluble monomer the process can be conducted directly in water as solvent or as an inverse emulsion-, -miniemulsion-, -microemulsion- or -suspension-polymerization.

By contacting the regulators of Formulas (1A) and (1B), wherein $R^7$ is a primary alkyl or —CN (in the latter case with a tertiary alkyl as $R^1$), with 1-substituted vinyl monomers of Formula (2) and/or 1,1-disubstituted vinyl monomers of Formula (3), optionally in combination with 1,2-disubstituted vinyl comonomers of Formula (4), a linear polymer will be obtained. By using similarly substituted multi-functional regulators of Formulas (1E), (1F) and (1H) (instead of (1A) and (1B)) multiple linear polymer segments will be linked to give 2-arm linear (for n=2), 3-arm star (n=3), 4-arm star (n=4), etc. polymer architectures.

When $R^7$ stands for hydrogen or —CN (in the latter case with a secondary alkyl as $R^1$), contacting regulators of Formulas (1A) and (1B) with 1,1-disubstituted vinyl monomers of Formula (3), will yield linear polymer. By using similarly substituted multi-functional regulators of Formulas (1E), (1F) and (1H) (instead of (1A) and (1B)) multiple linear polymer segments will be linked to give 2-arm linear (for n=2), 3-arm star (n=3), 4-arm star (n=4), etc. polymer architectures.

By contrast, when $R^7$ stands for hydrogen or —CN (in the latter case with a secondary alkyl as $R^1$), contacting regulators of Formulas (1A) and (1B) with 1-substituted vinyl monomers of Formula (2), optionally in combination with 1,2-disubstituted vinyl comonomers of Formula (4), will yield cyclic polymers, as is the case when using mixtures of 1-substituted vinyl monomers of Formula (2) and 1,1-disubstituted vinyl monomers of Formula (3), optionally in combination with 1,2-disubstituted vinyl comonomers of Formula (4).

A cyclic polymer structure is obtained, as the regulators of Formulas (1A) and (1B) are transformed in situ to the corresponding regulator compound of Formula (10) (when $R^7$=H) or its regioisomer in the case of, e.g., (1B-2) as in:

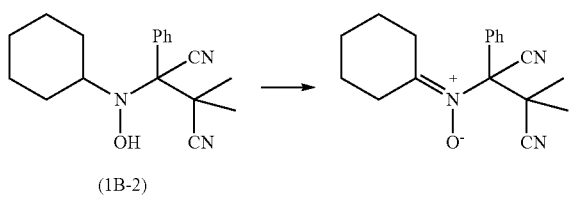

(1B-2)

This in situ transformation is best achieved by using 1-substituted vinyl monomers of Formula (2), carrying a conjugating group as $R^8$, such as Ph (i.e., styrene) or alkenyl (as in dienes, such as butadiene and isoprene), either as such (as exemplified herein for styrene P-REP) or by including a small fraction of preferably styrene comonomer in the recipe: preferably, styrene then amounts to at least ca. 5% of the monomer composition, when polymerizing highly reactive 1-substituted vinyl monomers of Formula (2), such as acrylic acid and its esters, but it may be as low as ca. 1% with the less reactive 1,1-disubstituted vinyl monomers of Formula (3), such as, e.g., methyl methacrylate (as demonstrated herein).

Cyclic vinyl polymer will also be obtained directly, i.e., by contacting the nitrone regulators of Formula (1C) with 1-substituted vinyl monomers of Formula (2) and/or with 1,1-disubstituted vinyl monomers of Formula (3), optionally in combination with 1,2-disubstituted vinyl comonomers of Formula (4).

By using similarly substituted multi-functional regulators of Formulas (1E) and (1F) (instead of (1A) and (1B)), and, more preferably, by using the multi-functional nitrone regulators of Formulas (1D), (1G) and (1I) multiple cyclic polymer rings will be linked into one polymer architecture.

Until now, potential advantages of cyclic vinyl polymer over its linear counterpart in end-use applications have not been exploited, because of a prohibitive cost of production. The process disclosed herein overcomes these present limitations and cyclic vinyl polymer can now be made in a manner fully compatible with industrial practice.

Polymers Obtainable by Polymerization Using Regulators of Formula (1)

The invention also relates to linear polymers according to Formulas (10) and cyclic polymers according to Formulas (11), which can be prepared in the process according to the present invention. The polymers can be homopolymers or copolymers of two or more vinyl monomers. Copolymers can have a random, gradient and/or (multi-)block structure, depending on the way that monomers are fed into the polymerization reactor.

The invention relates to linear polymers according to Formulas (10):

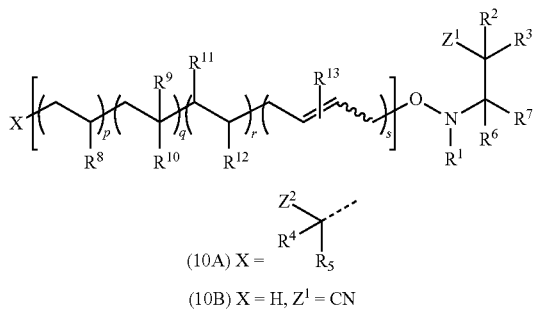

(10A) X =

(10B) X = H, $Z^1$ = CN where linear polymers according to Formula (10A) are obtained when using regulator compounds of Formula (1A) and those according to Formula (10B) when using (1B), in each case provided that either $R^7$ is a primary alkyl or —CN (in the latter case with a tert-alkyl as $R^1$), with all other substituents as defined above. wherein p represents the average number of one or more types of vinyl monomer units of Formula (2) incorporated in the polymer chain, and p ranges between 0 and 100.000;

wherein q represents the average number of one or more types of vinyl monomer units of Formula (3) incorporated in the polymer chain, and q ranges between 0 and 100.000;

wherein r represents the average number of one or more types of vinyl comonomer units of Formula (4) incorporated in the polymer chain, and r ranges between 0 and 100.000;

wherein s represents the average number of one or more types of diene monomer units incorporated in the polymer chain by cis- and/or trans-1,4- and/or 4,1-addition, $R^{13}$ stands for hydrogen, methyl and/or halogen, and s ranges between 0 and 100.000;

wherein p+q+r+s is at least 10;

The different monomer units can be present in the polymer chain in any order.

In a specific case, the invention also relates to linear polymers of Formulas (10A) and (10B), which are obtained when using the regulator compounds of Formulas (1A) and (1B), respectively, wherein $R^7$ does represent hydrogen or —CN (in the latter case with a secondary alkyl as $R^1$), when solely polymerizing the 1,1-disubstituted monomer(s) of Formula (3) (i.e. p=r=s=0).

The invention also relates to monocyclic polymers according to Formula (11C):

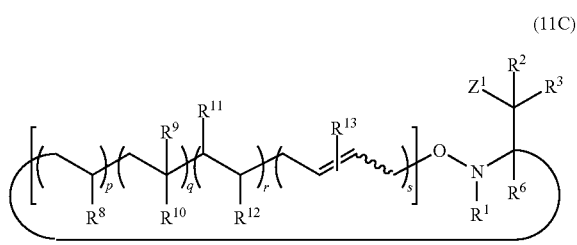

(11C)

where the monocyclic polymers according to Formula (11C) are obtained when using the regulator compounds of Formula (10) with all substituents and subscripts as defined above. Alternatively, when using the regulator compounds of Formulas (1A) and (1B), the same monocyclic polymers according to Formula (11C) are obtained, provided that $R^7$ is hydrogen.

By using the multi-functional regulators of Formulas (1E), (1F) and (1H) multiple linear polymer segments will be linked to give 2-arm linear (for n=2), 3-arm star (n=3), 4-arm star (n=4), etc. polymer architectures of Formulas (10E), (10F) and (10H), respectively:

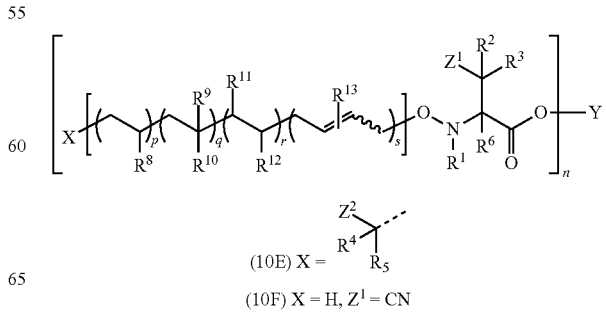

(10E) X =

(10F) X = H, $Z^1$ = CN

-continued

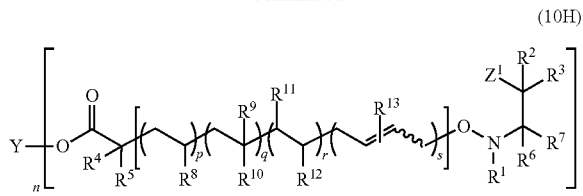
(10H)

in each case provided that either $R^7$ is a primary alkyl or —CN (in the latter case with a tertiary alkyl as $R^1$), wherein Y and n, as well as all further substituents and subscripts are as defined above.

By the same token, when using the multi-functional regulators of Formulas (1D), (1G) and (1I), multiple cyclic polymers will be linked into one polymer architecture, as is represented by Formulas (11D), (11G) and (11I), respectively:

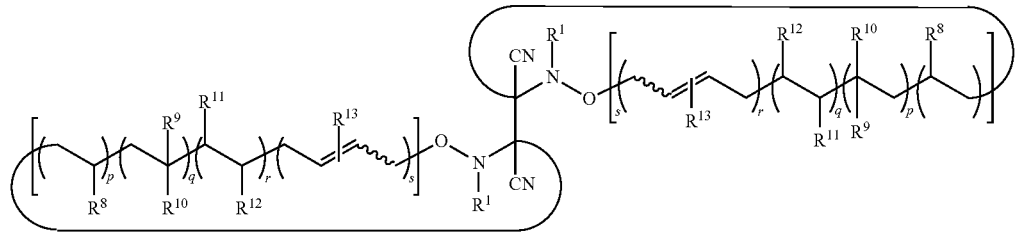
(11D)

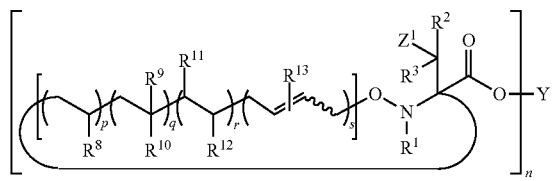
(11G)

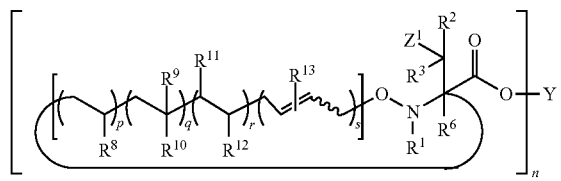
(11I)

wherein all substituents, as well as Y and all subscripts are as defined above.

As for the in situ transformation of the mono-functional regulators of Formulas (1A) and (1B) into (1C), followed by polymerization to give monocyclic polymers of Formula (11C), so will the multi-functional regulator compounds of Formulas (1E) and (1F), via in situ transformation into (1G) followed by polymerization, yield polymers of Formula (11G), in each case provided that $R^7$ is hydrogen and p≠0 in all cyclic block segments polymerized first.

The linear and cyclic polymers so obtained are thus novel polymers. Therefore, in another aspect the invention also relates to linear and cyclic polymers obtainable by the process of invention and to linear and cyclic polymers prepared from vinyl monomers selected from the group of 1-substituted vinyl monomers of Formula (2), 1,1-disubstituted vinyl monomers of Formula (3), 1,2-disubstituted vinyl comonomers of Formula (4), and mixtures thereof.

Preparation of Regulator Compounds of Formula (1)

Regulator compounds of Formula (1) can in principle be prepared by adaptation and integration of methodology known to a person skilled in the art. The issue is whether overall pricing of regulator compounds so prepared is economically justified for the intended uses. There still remains a need for a more cost-effective access from readily available and cheap raw materials.

Preparation of Alkoxyamine Regulators of Formula (1A) Via Hydroxy Compounds of Formula (1B)

Alkoxyamine regulators for Nitroxide-Mediated Polymerization (NMP) can be made in many ways (for a review on NMP including synthetic aspects of alkoxyamine regulators: Nicholas, J. et al. *Progr. Polym. Sc.* 2013, 38, 63-235). Two of the more general and preferred methods are radical trapping by nitroxide and 1,3-diradical trapping by nitrone (see next section).

Preparing an alkoxyamine regulator via nitroxide radical trapping requires that nitroxide is prepared first and that is has some persistence. The nitroxide is best prepared by oxidation of the corresponding N-hydroxy compound. The latter is prepared by addition to a nitrone of an organometallic reagent—in most precedents Grignard-type reagents have been used. Alternatively, it can be prepared by oxidation of the corresponding secondary amine or serve as an intermediate in the direct oxidation of amine to the nitroxide compound.

Alkoxyamine of Formula (1A) can be prepared by similar reaction sequences from hydroxy compound of Formula (1B) via nitroxide compound, as shown in Scheme (I):

Scheme (I)

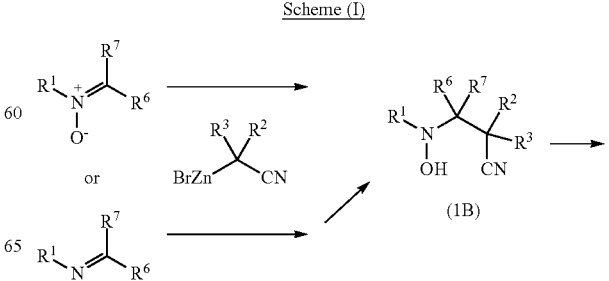
(1B)

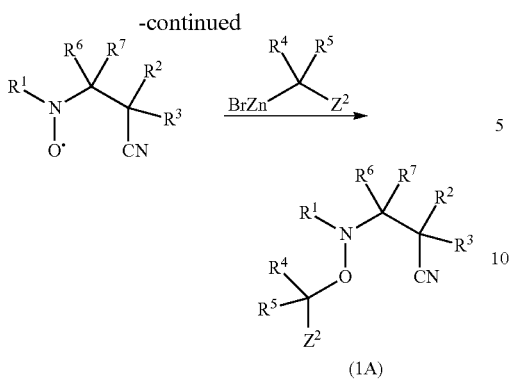

(1A)

The key step is addition of, preferably, an organozinc reagent (for a general review, cf.: Knochel, P.; Jones, P. *Organozinc Reagents: A Practical Approach*, Oxford University Press, 1999) either to the corresponding nitrone to afford the N-hydroxy compound of Formula (1B) directly or, alternatively, to the corresponding imine followed by oxidation. Oxidation of the N-hydroxy compound of Formula (1B) to the nitroxide compound is straightforward, as is coupling of the latter with the corresponding bromo compound to give the alkoxyamine of Formula (1A) by using an Atom Transfer Radical Addition (ATRA) protocol (as first described in Matyjaszewski, K. et al. *Macromolecules* 1998, 31, 5955-7).

Preparing Alkoxyamine Regulators Via 1,3-Diradical Trapping by Nitrone: State-of-Art In principle, preparing the alkoxyamine regulator via 1,3-diradical trapping by nitrone would be more efficient, as alkoxyamine is then prepared directly in one step instead of three. For the most part, this strategy has been investigated within the context of in situ Nitroxide-Mediated Polymerization (in situ NMP, for a review cf.: Sciannamea, V. et al. *Chem. Rev.* 2008, 108, 1104-26, and references cited therein).

In the course of in situ NMP alkoxyamine is first generated from N-tert-alkyl aldonitrone (in most examples PBN has been used) and a radical polymerization initiator (in most cases an azo compound) in the presence of part of the monomer during a pre-reaction period, followed by the addition of the remainder of monomer. Alternatively, monomer is only added to nitrone and azo compound after a pre-reaction period. While an in situ NMP process may yield linear polymer of low PDI, the method has several limitations (Sciannamea, V. et al. *Chem. Rev.* 2008, 108, 1104-26):
 in situ conversion of (expensive) nitrone is inefficient and needs excessive initiator;
 molecular weights are (significantly) higher than theoretical values;
 each combination of nitrone, initiator and monomer needs extensive optimization;
 pre-reaction at lower temperature is necessary in order to obtain polymer of low PDI, which is time consuming and would thus result in unacceptable batch times.

No process based on in situ NMP appears to have been implanted industrially.

A better approach is then to prepare pure alkoxyamine regulator from an N-tert-alkyl nitrone and an azo compound via 1,3-diradical trapping first, prior to using the pure alkoxyamine so obtained for controlling a vinyl polymerization. Remarkably, it appears that this strategy has been pursued only once, albeit with limited success (cf. Zink, M.-O. et al. *Macromolecules* 2000, 33, 8106-8). Thus, good methodology to effect this transformation and exploit alkoxyamines so prepared is still needed.

In view of these and other reported difficulties when using azo compounds as radical source at more elevated temperatures, an Atom Transfer Radical Addition protocol (ATRA, as first described in Matyjaszewski, K. et al. *Macromolecules* 1998, 31, 5955-7), but using a nitrone instead of nitroxide as substrate and performing the reaction at ambient temperature, was explored first, cf. Scheme (II):

Scheme (II)

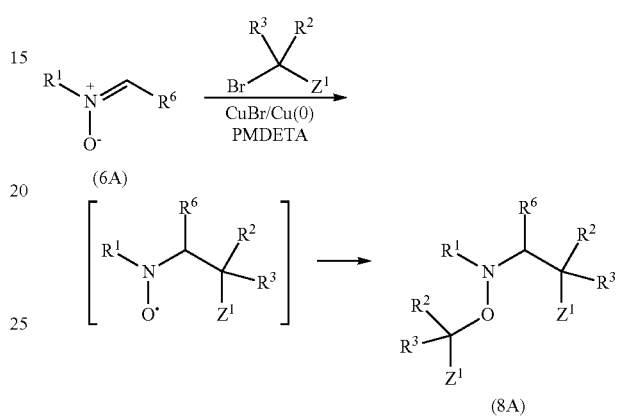

With methyl α-bromoisobutyrate ($R^2$=$R^3$=Me, $Z^1$=$CO_2$Me) the protocol works well with the N-tert-alkyl ($R^1$=t-Bu) aldonitrones of Formula (6A), carrying —CN (Example 13) or an ester group (Example 15) as $R^6$, although in the latter case the alkoxyamine product of Formula (8A) is sensitive to the base employed. By contrast, with phenyl as $R^6$ hardly any conversion of nitrone is observed, even when replacing tert-butyl as $R^1$ by a sterically less demanding cyclohexyl (Example 22). With α-bromoisobutyronitrile ($R^2$=$R^3$=Me, $Z^1$=—CN), conversion of the nitrone is low even when using the N-tert-alkyl ($R^1$=t-Bu) aldonitrone of Formula (6A) carrying —CN as $R^6$ (Example 11). Thus, 1,3-di-tert-radical addition to nitrone by an ATRA protocol is of limited scope.

The protocol is more suited for a 1,3-di-sec-radical addition reaction: e.g., all N-tert-alkyl ($R^1$=t-Bu) aldonitrones of Formula (6A) react with methyl 2-bromopropionate ($R^2$=Me, $R^3$=H, $Z^1$=$CO_2$Me), irrespective of the nature of $R^6$ (—CN, carboxylic acid ester, phosphonic acid esters, Ph), and alkoxyamines of Formula (8A) are so obtainable in high yields. By contrast, the use of (1-bromoethyl)benzene, while successful for —CN as $R^6$, fails for Ph. A major drawback of alkoxyamines so prepared is that they are slow to dissociate and initiate radical polymerization, because of the presence of a secondary alkyl at oxygen. Also, inclusion of some free nitroxide in a polymerization recipe is then needed in order to substantially improve control—or to achieve it at all (Nicholas, J. et al. *Progr. Polym. Sc.* 2013, 38, 63-235).

The major disadvantage of this ATRA protocol for producing alkoxyamine regulators directly from nitrones via 1,3-diradical trapping is the need for stoichiometric amounts of copper (salts) and ligand (PMDETA) to be used, which significantly raises the cost of raw materials, hinders an effective isolation of the desired alkoxyamines and generates large waste streams. Thus, there still remains a need for a better method to access alkoxyamine regulators directly from nitrones via 1,3-di-tert-radical trapping.

Preparation of Alkoxyamine Regulators of Formulas (8) Via 1,3-Di-Tert-Radical Trapping Regulator compounds of Formulas (1A) and (1E) have been prepared, wherein $R^5$ is identical to $R^2$, $R^4$ is identical to $R^3$, $Z^2$ is identical to $Z^1$ and $R^7$=H, which can be represented by the alkoxyamines of Formulas (8A) and (8E):

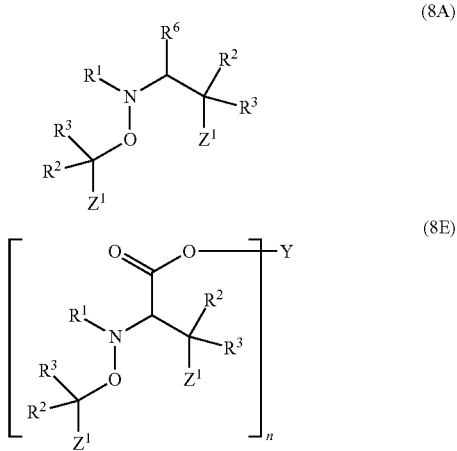

wherein $Z^1$ stands for —CN or a carboxylic acid ester of formula $C(O)OR^{21}$, wherein in case $R^2$ stands for Me or Et, $R^3$ stands for a primary alkyl (e.g., Me, Et, i-Bu) or wherein $R^2$ and $R^3$ may be joined in a ring (e.g., —$(CH_2)_5$—), wherein in case $R^1$ stands for a tertiary alkyl or tertiary aralkyl (e.g., t-Bu), $R^6$ stands for —CN or a carboxylic acid ester of formula $C(O)OR^{26}$, or wherein in case $R^1$ stands for a secondary alkyl or secondary aralkyl (e.g., c-Hex), $R^6$ stands for —CN, a carboxylic acid ester of formula $C(O)OR^{26}$ or a phosphonic acid ester of formula $P(O)(OR^{27})_2$, a (hetero)aryl (e.g., Ph) or an alkenyl, with $R^{21}$, $R^{26}$, $R^{27}$, Y and n as defined above, the compounds mentioned herein can be suitably prepared in a direct and cost-effective process from readily available starting materials. Therefore, another aspect of the invention relates to a process for the preparation of the alkoxyamines of Formulas (8), by reaction of the corresponding aldonitrones of Formulas (6):

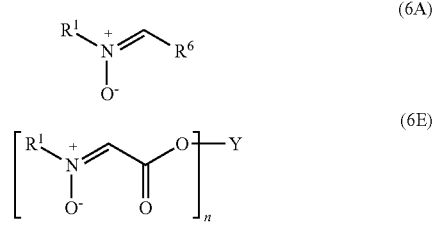

wherein $R^1$, $R^6$, Y and n are as defined above, and the corresponding azo-compound of Formula (7):

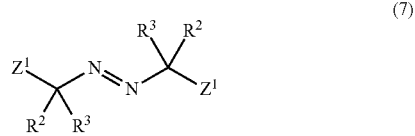

wherein $R^2$, $R^3$ and $Z^1$ are as defined above, in a 1,3-di-tert-radical addition reaction.

From earlier work (Iwamura, M. et al. *Bull. Chem. Soc. Jpn.* 1970, 43, 856-60) it is known that azo-compounds of Formula (7) azobisisobutyronitrile ($R^2$=$R^3$=Me, $Z^1$=—CN) (AIBN) and azobis(methyl isobutyrate) ($R^2$=$R^3$=Me, $Z^1$=$CO_2Me$) (AIBMe) show such 1,3-di-tert-radical addition to C-phenyl aldonitrones, carrying a (primary) N-benzyl or an N-phenyl substituent $R^1$, to give alkoxyamines in reasonable isolated yields (cf. also Examples 23 and 24).

However, these alkoxyamines fail to produce well-defined polymer, when used as a regulator in styrene polymerization (cf. Comparative Examples 51 and 52). This is to be expected, as alkoxyamines hitherto successful in styrene NMP have two tert-alkyl N-substituents or one tert-alkyl and one sec-alkyl N-substituent each as part of their structure (Nicholas, J. et al. *Progr. Polym. Sc.* 2013, 38, 63-235, and references cited therein). Those with two sec-alkyl N-substituents (cf., e.g., Benoit, D. et al. *J. Am. Chem. Soc.* 1999, 121, 3904-20) consistently fail to control styrene polymerization, as do those with N-phenyl (cf., e.g., Greene, A. C. et al. *Macromolecules* 2009, 42, 4388-90).

Prospect NMP regulators can then only be prepared by the 1,3-di-tert-radical addition reaction of N-tert-alkyl aldonitrones with an azo-compound of Formula (7), whereby alkoxyamines with one tert-alkyl and one sec-alkyl N-substituent each are obtained. By using N-sec-alkyl aldonitrones, alkoxyamines of Formula (8) with two secondary N-substituents are nonetheless to be made, which according to current state-of-art thinking should fail as regulator and were thus expected not to be suited: their role was then to serve for comparison only. (Note: attempts to prepare isomeric alkoxyamines with one sec-alkyl and one tert-alkyl N-substituent each, i.e. by reaction of N-sec-alkyl ketonitrones with an azo-compound, show limited conversion and thus fail).

Unfortunately, when 1,3-di-tert-radical additions to C-phenyl aldonitrone with tert-butyl as the N-substituent were attempted in the past, these failed to produce the desired alkoxyamines: with AIBN only nitroxide was isolated in very low yield (Iwamura, M. et al. *Bull. Chem. Soc. Jpn.* 1970, 43, 860-3; cf. Example 17). No example of 1,3-di-tert-radical addition to C-phenyl aldonitrone, carrying an N-secondary substituent, appears to have been reported.

Worse results are obtained when replacing phenyl by an aliphatic C-substituent in the aldonitrone: 1,3-di-tert-radical additions to known C-isopropyl aldonitrones show hardly any conversion and, thus, fail to produce alkoxyamine irrespective of the nature of the N-substituent, be that tertiary (t-Bu), secondary (c-Hex) or even primary (i-Bu). Further to that, even N-tert-butyl aldonitrone with a primary C-substituent (i-Bu) and the one with no C-substituent (i.e., 2-methyl-N-methylenepropan-2-amine oxide) fail to produce alkoxyamines in this manner.

The only hope then left is for introduction of an activating group in the nitrone. However, there has been no report on a 1,3-di-tert-radical addition to aldonitrones of Formula (6) that carry an activating group as $R^6$ (i.e., —CN, ester, phosphonate), irrespective of the nature of the N-substituent $R^1$. Further to that, the known synthesis methods for such aldonitrones would render the overall cost of prospect regulators of Formula (8) so produced untenable for most intended uses.

Although on the basis of all prior art prospects are bleak, such a preparation of the alkoxyamines of Formula (8) is highly attractive, as they can then be made efficiently from readily available and cheap raw materials, provided that the requisite aldonitrones of Formula (6) can be made in a cost-effective manner as well. Having secured access to the requisite aldonitrones of Formulas (6) in a technically viable and commercially attractive way (see below), in a special aspect therefore, the invention also provides for a process for the preparation of the alkoxyamines of Formulas (8):

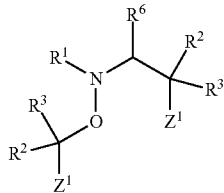
(8A)

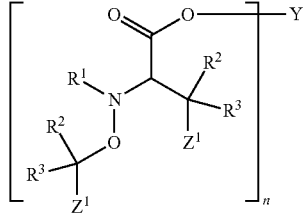
(8E)

wherein $R^1$, $R^2$, $R^3$, $R^6$, $Z^1$, Y and n are as defined above, by heating the aldonitrones of Formulas (6):

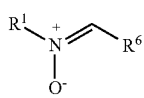
(6A)

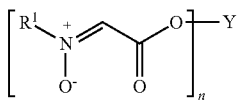
(6E)

wherein $R^1$, $R^6$, Y and n are as defined above, and the azo-compound of Formula (7):

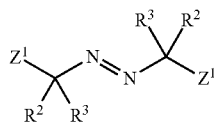
(7)

wherein $R^2$, $R^3$ and $Z^1$ are as defined above, in a solvent to form the alkoxyamines of Formulas (8).

In the process for the preparation of alkoxyamines of Formulas (8), wherein $R^1$ stands for tert-alkyl (e.g., t-Bu), $R^6$ preferably stands for —CN, since high conversions and good yields of alkoxyamines of Formulas (8) are then obtained in the reaction of nitrones of Formulas (6) with various azo-compounds of Formula (7). Good results are obtained as well with a carboxylic acid ester as $R^6$, as is demonstrated herein.

By contrast, when an amide or a carboxylic acid salt is used as $R^6$ in the nitrone of Formula (6A), hardly any reaction occurs. This supports the notion that aldonitrones of Formulas (6) must have a strong activating group as $R^6$ in order for 1,3-di-tert-radical addition to be successful, when R' stands for a tert-alkyl (e.g., t-Bu). That alkoxyamine is not isolated in the case of the nitrone of Formula (6A) with phosphonate as a strong activating group $R^6$ is not due to a lack in reactivity, but in product stability under the synthesis conditions.

When $R^1$ stands for a sec-alkyl (e.g., c-Hex), the 1,3-di-tert-radical addition process of the invention is successful for aldonitrones of Formulas (6) that carry any type of activating group (cyano, ester, phosphonate) and now also for those with a conjugating group (e.g., phenyl) as $R^6$, as is disclosed herein. The addition is tolerant to a wide variety of substituents in the conjugating group, with one notable exception, i.e., those in a position capable of H-bonding to the nitrone oxygen: no 1,3-di-tert-radical addition is observed with 2-hydroxy- or 2-carboxyphenyl as $R^6$, while complete conversion is found with a 4-hydroxyphenyl as $R^6$ in the nitrone of Formula (6A).

A side reaction that may occur to some extent during preparation is disproportionation of the alkoxyamines of Formulas (8). E.g., for the alkoxyamine of Formula (8A), this may lead to an NOH compound, which, when $Z^1$ stands for —CN, is stable and which is represented by Formula (8B), but when $Z^1$ stands for a carboxylic acid ester group, it further reacts by condensation to form the isoxazolidinone compound of Formula (9):

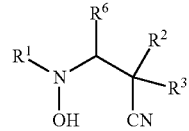
(8B)

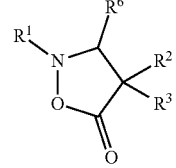
(9)

This side reaction is most prominent with AIBMe as the azo-compound of Formula (7): the presence of isoxazolidinone compound of Formula (9) can impede facile isolation of alkoxyamines of Formula (8). By contrast, hardly any disproportionation occurs when the azo-compound of Formula (7) is AIBN.

Reaction conditions such as temperature, stoichiometry and type of solvent for the preparation of the alkoxyamines of Formulas (8) are easily determined by a person skilled in the art. Thus, choice of temperature is primarily governed by the stability of the alkoxyamine under the reaction conditions. E.g., most alkoxyamines of Formulas (8) derived from AIBN are thermally stable, hence temperature is not a critical factor. By contrast, those derived from AIBMe are best prepared at a temperature of 92° C. or below in order to minimize disproportionation and contamination with isoxazolidinone compound of Formula (9).

Regarding stoichiometry, upon dissociation of, e.g., AIBN the two radicals formed can either combine in cage to give tetramethylsuccinonitrile (TMSN) or they can escape from the cage and then be trapped by nitrones of Formulas (6) to yield alkoxyamines of Formulas (8). The extent, to which TMSN is formed, is temperature dependent and needs to be accounted for in the stoichiometry. Thus, e.g., 1.6-1.7 equiv of AIBN per nitrone function is preferred at temperatures in the range of 85-92° C., while 1.1-1.3 equiv per nitrone function will suffice at 105° C. or above, to effect complete conversion of the nitrones of Formulas (6).

There are in principle no limitations regarding the nature of the solvent used, except that the nitrones of Formulas (6) are preferably completely dissolved at the reaction temperature. When solubility is too low, reaction may be incomplete, if solubilization occurs too slowly. Therefore, ester-, ether-, alcohol- and aromatic-type of solvent is generally preferred, while hydrocarbon is less suited. Alcohols may even be further preferred in specific cases, when they facilitate direct isolation of pure alkoxyamines (see below). The actual choice of solvent is best determined in function of the reaction temperature, so that a gentle reflux can be maintained throughout. For reaction temperatures in the range of 85-92° C. ethyl acetate and, optionally, isopropanol (where it facilitates direct isolation—see below) are most preferred, while at 105° C. toluene is most preferred.

When reaction is complete, the main contaminant is the in-cage combination product derived from the azo-compound, e.g., TMSN in the case of AIBN. Frequently, isolation can be easily accomplished by recrystallization, preferably from alcohol solvents, in case that the alkoxyamine of Formula (8A) is a single isomer (i.e., $R^2=R^3$). In special cases (cf. Example 18) the pure alkoxyamine is directly isolated in high yield, when the 1,3-di-tert-radical addition reaction is run in an alcohol solvent, preferably isopropanol. When crystallization fails and, in particular, when the alkoxyamines of Formulas (8) are mixtures of diastereomers (as is the case when $R^2 \ne R^3$ and for all 8E), steam stripping, an established procedure for removing TMSN and other in-cage combination products, is preferred.

The requisite aldonitrones of Formulas (6):

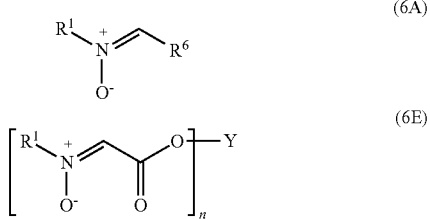

used in the process for the preparation of the alkoxyamines of Formulas (8A) and (8E), wherein $R^1$, $R^6$, Y and n are as defined above, are best prepared by oxidation of the corresponding amines of Formulas (5):

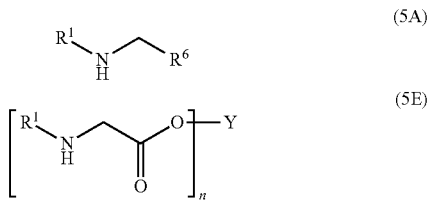

wherein $R^1$, $R^6$, Y and n are as defined above, in a water-acetone mixture containing the amine of Formula (5) and sodium- or potassium bicarbonate with potassium peroxymonosulfate as active ingredient in the formula $(KHSO_5)_2 \cdot KHSO_4 \cdot K_2SO_4$.

Known oxidation reactions to convert a secondary amine into an aldonitrone are not advantageous, in particular when attempting to prepare aldonitrones of Formulas (6) carrying an activating group as $R^6$ (—CN, ester, phosphonate).

Most examples to prepare aldonitrones of Formula (6A) with an activating group as $R^6$ involve C-cyano-aldonitrones and use m-chloroperoxybenzoic acid (mCPBA) as the oxidizing agent (cf. Patel, I. et al. *Org. Process Res. Dev.* 2009, 13, 49-53, and ref. cited therein). Although mCPBA can be used to prepare C-cyano-N-tert-butylnitrone (Example 1), its use renders the overall cost for regulator compounds prepared thereof prohibitive for most intended end-uses. Furthermore, when preparing a corresponding ester-substituted aldonitrone, starting material is only partly converted (Example 2), whereas for a corresponding phosphonate-substituted aldonitrone no product is formed (Example 3).

While oxidation by hydrogen peroxide and a sodium tungstate catalyst in methanol (cf. Murahashi, S. et al. *J. Org. Chem.* 1990, 55, 1736-44) is effective for aliphatic, as well as benzylic amines and has been used for the oxidation of cyclic (proline) α-aminoacid esters, its use in the synthesis of C-cyano-N-tert-butylnitrone produced a 1:1 mixture of nitrone and primary amide (Example 1), while for non-cyclic ester-substituted amine the yield is low (Example 2).

Dimethyldioxirane has been used in the synthesis of C-arylnitrones (Murray, R. W. et al. Ibid. 1990, 55, 2954-7), but their investigation showed that the use of amines lacking benzylic hydrogen showed side reactions and lower yields. In view of the necessity to distill and use this reagent as a highly dilute solution in acetone, this method is also impractical, if it were to be applied for making nitrones at industrial scale.

Oxidation with dimethyldioxirane generated in situ from acetone and Oxone under biphasic conditions using a Phase Transfer Catalyst (PTC), has been described for one cyclic ester (Baldwin, S. W. et al. *Tetrahedron Lett.* 1998, 39, 6819-22), but no report is known for non-cyclic aldonitrones C-substituted with an activating group. More recently, trifluoromethylketones have been used under PTC conditions for generating dioxiranes in situ for the oxidation of a cyclic (proline) ester (Gella, C. et al. *J. Org. Chem.* 2009, 74, 6365-7), but pricing of the reagents employed does not render this a commercially viable option.

Furthermore, these and other known procedures for the in situ generation of dioxiranes all proceed under dilute conditions (amine concentration 0.2 M or less in the organic phase) and in the presence of toxic solvents and PTC: large quantities of solvents used and large waste streams generated are undesirable from both cost- and environmental perspectives. Also, PTC can contaminate, or prevent easy isolation of, the aldonitrone targets. Further to that, such a procedure would not be suited for C-cyano aldonitrones, because cyano groups have been converted to primary amides under comparable reaction conditions (cf. Bose, D. S. et al. *Syn. Commun.* 1997, 27, 3119-23).

In a special aspect therefore, the invention also provides for an improved process for the preparation of the aldonitrones of Formulas (6):

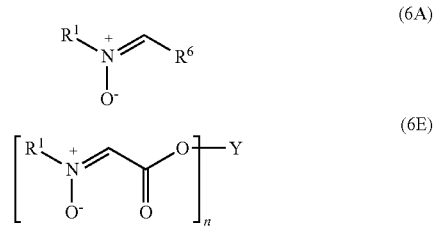

from the corresponding amines of Formulas (5):

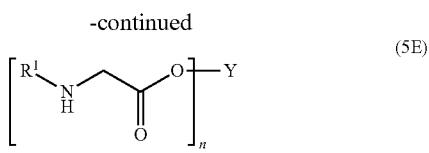

by oxidation of the corresponding amines of Formula (5) with solid Oxone being added to an acetone-water mixture containing amine of Formulas (5) and sodium- or potassium or sodium bicarbonate. Oxone is a tradename for $(KHSO_5)_2 \cdot KHSO_4 \cdot K_2SO_4$, which contains potassium peroxymonosulfate as the active ingredient (commercially available from Dupont; alternatively, the same formula is available from Evonik under the trade name Caroat).

Compared to prior art, neither phase transfer catalyst nor further organic solvent is needed, while oxidation according to the invention may be accomplished at a 10-fold (or higher) concentration of amine compound (typically 1.5 M up to 2 M), thus reducing the need for large quantities of solvents and making this process environmentally more benign. When replacing acetone by butanone incomplete conversion is found under otherwise identical conditions, indicating that the use of acetone is critical. The nature of base used is not critical: e.g., both sodium bicarbonate and potassium bicarbonate can equally well be used.

For conversion of N-tert-alkyl amines carrying an activating group as $R^6$ (—CN, ester, phosphonate) in Formulas (5) a reaction temperature below ca. 40° C. is preferred. For conversion of corresponding N-sec-alkyl amines a reaction temperature around 25° C. or below is preferred. Aldonitrones of Formulas (6) are easily isolated using extraction and crystallization procedures known per se and are obtained in sufficiently pure form to be used in subsequent reactions (such as Reaction II below).

Preparation of Nitrone Regulators of Formula (1C)

Nitrones of Formula (1C) can be prepared using methods known in the art. To this end, the most general method is by condensation reaction from a hydroxylamine compound and a carbonyl compound (illustrated in Examples 35 and 36). In a specific case they can be made from hydroxylamine compound and alkyne by an addition-tautomerization reaction (Nguyen, T. B. et al. Org. Lett. 2008, 10, 4493-6; employed in Example 34).

These methods are less preferred from an industrial perspective, as pricing of the hydroxylamine compounds (when commercially available) is prohibitive for all intended end-uses. Further to that, within the context of the present invention only nitrones of Formula (1C), carrying a carboxylic ester group as $R^6$, are accessible in this manner.

Preparing Specific Nitrone Regulators of Formulas (10) and (1G) from Alkoxyamine Regulators of Formulas (8A) and (8E)

Specific nitrone regulators of Formulas (1C) and (1G):

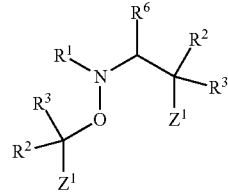

(1C)

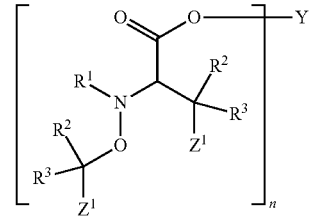

(1G)

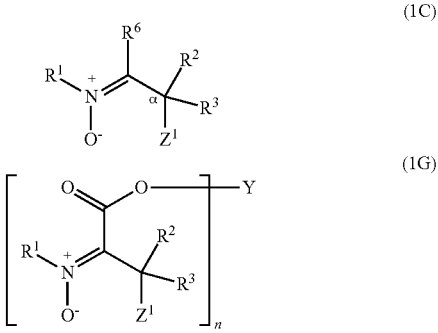

wherein $Z^1$ stands for —CN or a carboxylic acid ester of formula $C(O)OR^{21}$, wherein in case $R^2$ stands for Me or Et, $R^3$ stands for a primary alkyl (e.g., Me, Et, i-Bu) or wherein $R^2$ and $R^3$ may be joined in a ring (e.g., —$(CH_2)_5$—), wherein in case $R^1$ stands for a tertiary alkyl or tertiary aralkyl (e.g., t-Bu), $R^6$ stands for —CN or a carboxylic acid ester of formula $C(O)OR^{26}$, or wherein in case $R^1$ stands for a secondary alkyl or secondary aralkyl (e.g., c-Hex), $R^6$ stands for —CN, a carboxylic acid ester of formula $C(O)OR^{26}$ or a phosphonic acid ester of formula $P(O)(OR^{27})_2$, a (hetero)aryl (e.g., Ph) or an alkenyl, with $R^{21}$, $R^{26}$, $R^{27}$, Y and n as defined above, can be suitably prepared in a direct and cost-effective process from readily available starting materials. Therefore, another aspect of the invention relates to a process for the preparation of specific nitrone regulators of Formulas (1C) and (1G) from the corresponding alkoxyamines of Formulas (8A) and (8E), respectively:

(8A)

(8E)

wherein $R^1$, $R^2$, $R^3$, $R^6$, $Z^1$, Y and n are as defined above, by their treatment with a metal alkoxide or amine base.

To effect this transformation, for which there is no prior art, there is no need to use a strong base (such as a metal hydride, e.g., sodium hydride, or a metal amide, e.g., lithium diisopropylamide) under rigorous exclusion of air and water: a metal alkoxide base (e.g., potassium tert-butoxide or sodium methoxide) in a polar aprotic solvent, e.g., N,N-dimethylformamide (DMF) suffices. Whereas with —CN as $R^6$ a catalytic amount of the base suffices, use of an ester or phosphonate as $R^6$ requires stoichio-metric amounts of metal alkoxide base, while for phenyl as $R^6$ at least 2 equiv. of the base are needed. Remarkably, in general for —CN as $R^6$ even a sub-stoichiometric amount of a weaker organic amine base, such as, e.g., 1,8-Diazabicyclo[5.4.0]undec-7-ene (DBU) in an organic solvent, is able to effect this transformation, as is sometimes observed when using a carboxylic acid ester as $R^6$.

The reaction temperature does not appear to be critical, nor is there any need to rigorously exclude water or oxygen. This process for transforming alkoxyamines of Formulas (8A) and (8E) into the corresponding nitrones of Formulas (1C) and (1G) can be performed with a high yield and efficiency, thus providing access to nitrones of Formulas (1C) and (1G) from commercially attractive and readily available starting materials.

BRIEF DESCRIPTION OF THE DRAWINGS

FIG. 1 discloses the development of the monomer conversion as a function of time and the development of the number average molecular weight as a function of the conversion for styrene polymerization.

FIG. 2 discloses the development of the monomer conversion as a function of time and the development of the number average molecular weight as a function of the conversion for methacrylics polymerization.

DETAILED DESCRIPTION OF THE INVENTION

The invention is now elucidated by way of the following examples, without however being limited thereto:

EXAMPLES

Synthesis General

Commercial grade reagents, solvents, initiators and monomers were purchased from Aldrich, Wako and TCI, and unless specified used as received. 1,3,5-Tricyclohexylhexahydro-1,3,5-s-triazine was prepared in 85% yield after recrystallization according to Bujnowski, K. et al. *ARKIVOC* 2008, 106-14. Azo-initiator azobis(α-ethylbutyronitrile) (AEBN) was prepared according to Dox, A. W. *J. Am. Chem. Soc.* 1925, 47, 1471-7. N-(2-Methyl-1-phenylpropyl)hydroxylamine was prepared from isobutyrophenone by sodium cyanoborohydride reduction of its oxime and isolated as the p-toluenesulfonic acid salt.

Synthesis of Aldonitrones of Formula (6A) Using Oxone Oxidation

Examples 1 through 10 disclose the preparation of representative aldonitrone compounds, in particular those carrying cyano-, ester- and phosphonate-type of activating groups, from secondary amines, employing Oxone as the oxidizing agent. This is schematically illustrated by Reaction (I):

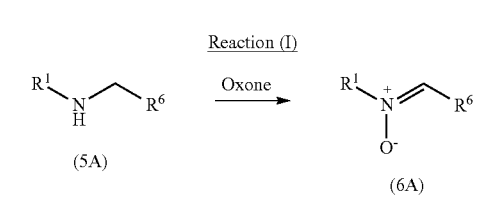

Example 1: (Z)—N-(cyanomethylene)-2-methylpropan-2-amine oxide

Step 1: Into a 500-mL Erlenmeyer flask with stirrer bar were charged 252 mL (3 equiv) of tert-butylamine and 150 mL of ethyl acetate and the flask was cooled in a water bath. To this was added drop wise 60.4 g (50.6 mL, 0.8 mol) of chloroacetonitrile in 30 min and the resulting mixture was

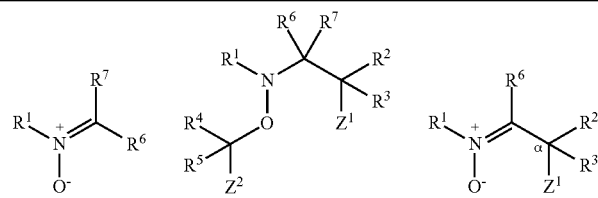

Synthesis Overview:

| Examples | | | R$^1$ | R$^2$ | R$^3$ | R$^4$ | R$^5$ | R$^6$ | R$^7$ | Z$^1$ | Z$^2$ |
|---|---|---|---|---|---|---|---|---|---|---|---|
| 1 | 11 | 26 | t-Bu | Me | Me | Me | Me | CN | H | CN | CN |
| 1 | 12 | — | t-Bu | Et | Et | Et | Et | CN | H | CN | CN |
| 1 | 13 | 27 | t-Bu | Me | Me | Me | Me | CN | H | C(O)OMe | C(O)OMe |
| 2 | 14 | 28 | t-Bu | Me | Me | Me | Me | C(O)OMe | H | CN | CN |
| 2 | 15 | — | t-Bu | Me | Me | Me | Me | C(O)OMe | H | C(O)OMe | C(O)OMe |
| 3 | 16 | — | t-Bu | Me | Me | Me | Me | P(O)(OEt)$_2$ | H | CN | CN |
| 4 | 17 | — | t-Bu | Me | Me | Me | Me | Ph | H | CN | CN |
| 5 | 18 | 25 | c-Hex | Me | Me | Me | Me | CN | H | CN | CN |
| 6 | 19 | 29 | c-Hex | Me | Me | Me | Me | C(O)OEt | H | CN | CN |
| 7 | 20 | 30 | c-Hex | Me | Me | Me | Me | P(O)(OEt)$_2$ | H | CN | CN |
| 8 | 21 | 31 | c-Hex | Me | Me | Me | Me | Ph | H | CN | CN |
| 8 | 22 | — | c-Hex | Me | Me | Me | Me | Ph | H | C(O)OMe | C(O)OMe |
| 9 | 23 | 32 | Bn | Me | Me | Me | Me | Ph | H | CN | CN |
| 10 | 24 | 33 | Ph | Me | Me | Me | Me | Ph | H | CN | CN |
| — | — | 34 | Ph(i-Pr)CH | H | H | — | — | C(O)OMe | — | C(O)OMe | — |
| — | — | 35 | Ph(i-Pr)CH | H | H | — | — | C(O)OMe | — | H | — |
| — | — | 36 | Ph(i-Pr)CH | H | H | — | — | C(O)OMe | — | CH$_2$C(O)OMe | — |

2-((tert-Butyl(1-(diethoxyphosphoryl)-2,2-dimethylpropyl)amino)-oxy)-2-methylpropanoic acid, commercialized by Arkema under the trade name Bloc Builder® MA regulator, was prepared according to literature procedures. NMR spectra were recorded on a Bruker Avance DPX 300 spectrometer in CDCl$_3$ as solvent at 298 K or, for fully characterizing the alkoxyamines of Examples 18-24, in toluene-d8 at 368 K (because of strong broadening when recorded at ambient temperature). Examples 9-23-32 (and 51) with R$^1$ is benzyl (Bn), and 10-24-33 (and 52) with R$^1$ is phenyl (Ph) are comparative, since a primary aralkyl and an aryl are applied, respectively.

left to stir for 3 d at room temperature. The reaction mixture was filtered with the aid of 250 mL of ethyl acetate. The filtrate was washed with water, brine, dried over sodium sulfate and after filtration volatiles were evaporated to yield 73.6 g (82%) of a colorless liquid of greater than 98% purity ($^1$H NMR) and suited as such for further use. $^1$H NMR δ 1.11 (s, 9H, t-Bu), 1.17 (br, 1H, N—H), 3.53 (s, 2H, CH$_2$); $^{13}$C NMR δ 28.91 (t-Bu), 31.17 (CH$_2$), 51.51 (C—N), 119.90 (C≡N).

Note: alternatively, material of similar quality was prepared in 86% yield according to Exner, L. J. et al. *J. Am. Chem. Soc.* 1953, 75, 4841-2, and used successfully in the oxidation step.

Step 2: Product of Step 1 dissolved in 450 mL of acetone was added to a 2-L beaker containing a mechanically stirred solution/suspension of 250 g of sodium bicarbonate in 450 mL of water. 460 g of Oxone (1.13 mole equiv) was added in small portions of ca. 10 g in the course of 1 h; small portions of crushed ice were occasionally added to maintain the temperature below ca. 40° C. After Oxone addition was complete, stirring was continued for 1 h. Next, 400 mL of ethyl acetate was added and after stirring for 5 min the reaction mixture was allowed to phase separate, where after the top layer was decanted; this was repeated 3 times with 200-mL portions of ethyl acetate. Next, the combined organic phases were washed twice with brine, dried over sodium sulfate, and after filtration solvents were removed by evaporation to leave a reddish liquid that may crystallize on standing. Yield 70.6 g (85% or 70% over 2 steps). The product obtained is sufficiently pure for further use. $^1$H NMR δ 1.54 (s, 9H, t-Bu), 6.85 (s, 1H, HC=N); $^{13}$C NMR δ 28.16 (t-Bu), 74.78 (C—N), 103.88 (C=N), 112.98 (C≡N).

Note: until now, m-chloroperoxybenzoic acid (mCPBA) has been used for the oxidation of cyanomethylamines (Patel, I. et al. *Org. Process Res. Dev.* 2009, 13, 49-53 and references cited therein): although this nitrone could be prepared by mCPBA oxidation, the pricing of mCPBA makes this process commercially less attractive. When applied to N-cyanomethylamines, oxidation by hydrogen peroxide and a sodium tungstate catalyst in methanol (as first described by Murahashi, S. et al. *J. Org. Chem.* 1990, 55, 1736-44) produced 1:1 mixtures of the desired nitrone and the corresponding primary amide and, hence, an unacceptably low yield.

Example 2: (Z)—N-(2-methoxy-2-oxoethylidene)-2-methylpropan-2-amine oxide

Step 1: Into a 1-L Erlenmeyer flask with stirrer bar were charged 300 mL (ca. 4 equiv) of tert-butylamine and 550 mL of tert-butyl methyl ether, and the solution was cooled in an ice bath. To the stirred solution was added drop wise 110.1 g (68.2 mL; 0.72 mol) of methyl bromoacetate in ca. 90 min and the resulting mixture was then stirred at room temperature overnight. The reaction mixture was filtered with the aid of 275 mL of tert-butyl methyl ether and volatiles were removed by evaporation to yield 96.2 g (92%) of a slightly colored liquid of greater than 99% purity ($^1$H NMR) and suited as such for further use. $^1$H NMR δ 1.08 (s, 9H, t-Bu), 1.50 (br, 1H, N—H), 3.38 (s, 2H, CH$_2$), 3.70 (s, 3H, OMe); $^{13}$C NMR δ 28.96 (t-Bu), 44.99 (CH$_2$), 50.45 (C—N), 52.06 (OMe), 173.68 (C=O).

Step 2: According to the general recipe described in Example 1 using crude product of Step 1 and 250 g of sodium bicarbonate in 450 mL each of acetone and water, then adding portion wise 460 g of Oxone gave after work up the crude nitrone as a slightly yellow liquid in 74.0 g (73%) yield. $^1$H NMR δ 1.50 (s, 9H, t-Bu), 3.76 (s, 3H, OMe), 7.25 (s, 1H, HC=N); $^{13}$C NMR δ 28.26 (t-Bu), 51.93 (OMe), 74.89 (C—N), 121.16 (C=N), 161.46 (C=O).

Note: starting from the appropriate bromoacetate ester, this 2-step procedure could equally well be used for the preparation of, a.o., ethyl (94% and 82%), benzyl (99% and 88%) and tert-butyl (93% in Step 1 and 88% in Step 2, respectively) ester-substituted N-tert-butyl aldonitrones. For the methyl ester an oxidation by hydrogen peroxide and a sodium tungstate catalyst in methanol (cf. Murahashi, S. et al. *J. Org. Chem.* 1990, 55, 1736-44), provided nitrone in ca. 10% isolated yield, which is far below that obtained by the process of the invention. For the ethyl ester the use of m-chloroperoxybenzoic acid (mCPBA) in a recipe that was successful for the oxidation of cyanomethylamines (cf. Patel, I. et al. *Org. Process Res. Dev.* 2009, 13, 49-53 and references therein), gave only partial conversion of this amine and yields of the nitrone isolated after column chromatography were below 40%.

Example 3: Z—N-((diethoxyphosphoryl)methylene)-2-methylpropan-2-amine oxide

Step 1: Into a 1-L round-bottom flask were charged 110.5 g (0.80 mol) of diethyl phosphite, 400 mL of toluene, 110 mL (1.3 equiv) of tert-butylamine, 1.6 g (1 mol %) of p-toluenesulfonic acid hydrate and 24 g of paraformaldehyde. The flask was equipped with a Dean-Stark trap and reflux condenser with calcium chloride tube, and the contents were stirred and heated at reflux for ca. 1.5 h under a nitrogen atmosphere. After cooling to ca. 70° C. 10 g of sodium bicarbonate was added, and the reaction mixture was then refluxed for another 0.5 h. After cooling to room temperature the reaction was filtered and solvent and other volatiles were then evaporated. The product so obtained contained ca. 30% of diethyl hydroxymethylphosphonate. Acidification, followed by washing and neutralization removed most of this component and gave the amine in 107.4 g (60%) yield. $^1$H NMR δ 1.04 (s, 9H, t-Bu), 1.28 (t, 6H, OEt), 1.5-2.5 (br, 1H, N—H), 2.86 (d, 2H, $^2J_{HP}$=15, CH$_2$P), 4.10 (m, 4H, OEt); $^{13}$C NMR δ 16.42 (d, $^3J_{CP}$=6, OEt), 28.26 (t-Bu), 38.49 (d, $^1J_{CP}$=151, CH$_2$P), 51.04 (d, $^3J_{CP}$=15, C—N), 62.20 (d, $^2J_{CP}$=6, OEt); $^{31}$P NMR δ28.57.

Step 2: According to the general recipe disclosed in Example 1 using the crude product of Step 1 and 170 g of sodium bicarbonate in 350 mL each of acetone and water, then adding portion wise 330 g of Oxone gave after work up in 91% yield the nitrone as a nearly colorless liquid. $^1$H NMR δ 1.33 (t, 6H, OEt), 1.51 (s, 9H, t-Bu), 4.25 (qui, 4H, OEt), 6.94 (d, 1H, $^2J_{HP}$=26, HC=N); $^{13}$C NMR δ 16.37 (d, $^3J_{CP}$=6, OEt), 28.19 (t-Bu), 63.21 (d, $^2J_{CP}$=6, OEt), 73.34 (d, $^3J_{CP}$=8, C—N), 121.31 (d, $^1J_{CP}$=211, C=N); $^{31}$P NMR δ 8.64.

Note: use of m-chloroperoxybenzoic acid (mCPBA) that was successful for oxidizing cyanomethylamines (cf. Patel, I. et al. *Org. Process Res. Dev.* 2009, 13, 49-53 and references cited therein), completely converted amine starting material, but gave none of the desired nitrone.

Example 4: (Z)—N-benzylidene-2-methylpropan-2-amine oxide (PBN)

Step 1: As in Example 2, using 136.8 g (95.2 mL, 0.8 mol) of benzyl bromide, gave after work-up 128.0 g (98%) of a colorless liquid that is sufficiently pure for the next step: it contains less than 2% of bis-alkylation product (δ 3.66). $^1$H NMR δ 1.14 (s, 9H, t-Bu), 1.0-1.4 (br, 1H, N—H), 3.69 (s, 2H, CH$_2$), 7.20-7.45 (m, 5H, Ph); $^{13}$C NMR δ 29.16 (t-Bu), 47.27 (CH$_2$), 50.64 (C—N), 126.68, 128.30 and 128.36 (each C—H, Ph), 141.52 (q-C, Ph).

Step 2: According to the general recipe disclosed in Example 1, using crude product of Step 1 and 300 g of sodium bicarbonate in 500 mL each of acetone and water, then adding portion wise 530 g of Oxone, gave after work up 119.1 g (90%) of crude nitrone. Recrystallization from n-heptane-ethyl acetate (7:1 v/v) gave a first crop of pure PBN. Evaporation of the filtrate followed by recrystallization gave a second crop. Total yield of PBN: 102.1 g (72% over 2 steps). $^1$H NMR δ 1.61 (s, 9H, t-Bu), 7.40 (m, 3H, Ph), 7.53 (s, 1H, HC=N), 8.28 (m, 2H, Ph); $^{13}$C NMR δ 28.48 (t-Bu), 70.93 (C—N), 128.53, 128.88 and 130.17 (each C—H, Ph), 129.84 (C=N), 131.22 (q-C, Ph).

Example 5:
(Z)—N-(cyanomethylene)cyclohexanamine oxide

Step 1 (i.e. a minor adaptation of the work published as Exner, L. J. et al. *J. Am. Chem. Soc.* 1953, 75, 4841-2): To a solution of 125.3 g (0.66 mol) of sodium metabisulfite in 200 mL of water was added 97.4 g of >37.0% formaline (≥1.2 mol) (exothermic), and the solution was heated for 45 min at 70° C. After cooling to 60° C., 126.0 g (1.27 mol) of cyclohexylamine was rapidly added and stirring was continued for 0.5 h at that temperature. After cooling to room temperature, a solution of 62.5 g (1.275 mol) of sodium cyanide in 250 mL of water was added drop wise in 1 h, and stirring was continued for 4 h. Water and toluene (500 mL each) were added and the layers were separated. The aqueous layer was extracted once more with 250 mL of toluene. The combined organic layers were washed with water and with brine, dried over sodium sulfate, and after filtration the solvents were evaporated to give 155.9 (94%) of the product as a colorless liquid that is sufficiently pure for the next step. It contains less than 2% of bis-alkylation product (δ 3.67): $^1$H NMR δ 0.99-1.34 (m, 6H) and 1.54-1.85 (m, 5H) (c-Hex and N—H), 2.64 (tt, 1H, CHN), 3.58 (s, 2H, CH$_2$N); $^{13}$C NMR δ 24.59, 26.05, 32.77 and 34.49 (c-Hex), 55.32 (CH$_2$N), 118.30 (C≡N).

Step 2: According to the general recipe disclosed in Example 1 (with a slightly higher excess of reagents) using the crude product of Step 1 and 470 g of potassium bicarbonate in 600 mL each of acetone and water, then adding portion wise 830 g of Oxone in 2 h. Recrystallization from cyclohexane-ethyl acetate (3:1 v/v) gave a first crop of nitrone. Evaporating the filtrate followed by recrystallization gave a second crop. Total yield: 126.2 g (75%) of nitrone as a single isomer. $^1$H NMR δ 1.13-1.36 (m, 3H) and 1.60-2.04 (m, 7H) (c-Hex), 3.92 (tt, 1H, HC—N), 6.79 (s, 1H, HC=N); $^{13}$C NMR δ 24.71, 24.75 and 31.25 (c-Hex), 76.53 (HC—N), 105.26 (HC=N), 112.66 (C≡N).

Note: when acetone was replaced by methyl ethyl ketone under standard operating conditions, up to 30% of hydroxylamine intermediate was present after work up. Thus, the use of an acetone-water mixture for the oxidation using Oxone is preferred.

Example 6: (Z)—N-(2-ethoxy-2-oxoethylidene)cyclohexanamine oxide

Step 1: Into a 1-L Erlenmeyer flask with stirrer bar were charged 365 mL (4 equiv) of cyclohexylamine and 500 mL of toluene and the solution was cooled in an ice bath. To the stirred solution was added drop wise in ca. 2 h 133.6 g (88.7 mL; 0.8 mol) of ethyl bromoacetate and the resulting mixture was stirred overnight at room temperature. The reaction mixture was filtered with the aid of 250 mL of toluene and volatiles were then evaporated. Residual cyclohexylamine was removed by co-evaporation with toluene. This gave 139.3 g (95%) of product as a colorless liquid that was sufficiently pure for the next step. It contained less than 0.5% of bis-alkylation product (δ 3.48). $^1$H NMR =□0.90-1.2 (m, 6H) and 1.50-1.80 (m, 5H) (c-Hex and N—H), 1.19 (t, 2H, OEt), 2.32 (tt, 1H, CHN), 3.34 (s, 2H, CH$_2$N), 4.10 (q, 2H, OEt); $^{13}$C NMR δ□14.26 (OEt), 24.89, 26.10, 33.36 and 48.34 (c-Hex), 56.47 (CH$_2$N), 60.71 (OEt), 172.89 (C=O).

Step 2: According to the general recipe disclosed in Example 1 using crude product of Step 1 and 320 g of sodium bicarbonate in 500 mL of acetone and 1000 mL of water, then adding at ambient temperature portion wise 600 g of Oxone in 2.5 h. After work up crude nitrone was recrystallized from n-heptane-ethyl acetate (7:1 v/v) to give 83.2 g (52% over 2 steps) of (Z) product, containing 5% of (E) isomer ($^1$H NMR δ□5.50 (CH—N) and 7.08 (HC=N)). $^1$H NMR (Z) δ 1.24 (t, 3H, OEt), 1.10-1.39 (m, 3H), 1.62 (m, 1H) and 1.75-2.00 (m, 6H) (c-Hex), 3.78 (tt, 1H, HC—N), 4.19 (q, 2H, OEt), 7.11 (s, 1H, HC=N); $^{13}$C NMR δ 14.28 (OEt), 24.89, 24.89 and 31.21 (c-Hex), 60.86 (OEt), 78.13 (HC—N), 123.53 (HC=N), 160.41 (C=O).

Note: starting from the appropriate bromoacetate ester, this 2-step procedure could equally well be used for the preparation of, a.o., methyl (48%), benzyl (50%) and tert-butyl (54% over 2 steps) C-ester N-cyclohexyl aldonitrones.

Example 7: (Z)—N-((diethoxyphosphoryl)methylene)cyclohexanamine oxide

Step 1: 95.0 g (0.285 mol) of recrystallized 1,3,5-tricyclohexylhexahydro-1,3,5-s-triazine and 130.0 g (0.94 mol; 3.3 equiv) of diethyl phosphite were refluxed in 100 mL of cyclohexane overnight. The solvent was evaporated to give crude amine sufficiently pure for use in the next step. $^1$H NMR δ 0.90-1.30 (m, 6H) and 1.43-1.78 (m, 5H) (c-Hex and N—H), 1.24 (t, 6H, OEt), 2.36 (tt, 1H, HC—N), 2.90 (d, 2H, $^2J_{HP}$=12, CH$_2$P), 4.05 (m, 4H, OEt); $^{13}$C NMR δ 16.55 (d, $^3J_{CP}$=6, OEt), 24.87, 26.15 and 33.09 (c-Hex), 42.43 (d, $^1J_{CP}$=153, CH$_2$P), 57.79 (d, $^3J_{CP}$=15, HC—N), 62.10 (d, $^2J_{CP}$=7, OEt); $^{31}$P NMR δ 28.20.

Step 2: According to the general recipe disclosed in Example 1 using the crude product of Step 1 and 350 g of sodium bicarbonate in 500 mL each of acetone and water, then adding portion wise at ambient temperature 630 g of Oxone in 2 h, gave crude nitrone as a 95:5 mixture of (Z) and (E) isomers, containing 5% of an unidentified product ($^{31}$P NMR δ 28.92). Recrystallization from n-heptane-ethyl acetate (8:1 v/v) gave a first crop of nitrone. Evaporation of the filtrate followed by recrystallization gave a second crop. Total yield: 160.8 g (72% over 2 steps) of (Z)-nitrone as waxy crystals, containing 1% of (E)-isomer ($^1$H NMR δ 6.80 (d); $^{31}$P NMR δ 6.97). $^1$H NMR (Z) δ 1.05-1.35 (m, 3H), 1.57-1.86 (m, 5H) and 1.95-2.05 (m, 2H) (c-Hex), 1.27 (t, 6H, OEt), 3.76 (m, 1H, HC—N), 4.18 (m, 4H, OEt), 6.78 (d, 1H, $^2J_{HP}$=15, HC=N); $^{13}$C NMR δ 16.50 (d, $^3J_{CP}$=6, OEt), 24.91, 25.00 and 31.55 (c-Hex), 63.30 (d, $^2J_{CP}$=6, OEt), 77.00 (d, $^3J_{CP}$=8, HC—N), 123.32 (d, $^1J_{CP}$=209, HC=N); $^{31}$P NMR δ 7.70.

Example 8: (Z)—N-benzylidenecyclohexanamine oxide

Step 1: Into a 1-L Erlenmeyer flask with stirrer bar were charged 360 mL (ca. 3.5 equiv) of cyclohexylamine and 500 mL of ethyl acetate and the solution was cooled in an ice bath. To the stirred solution was added drop wise in ca. 2.0 h 153.9 g (107.0 mL; 0.9 mol) of benzyl bromide and the resulting mixture was stirred at ambient temperature overnight. The reaction mixture was filtered with the aid of 500 mL of toluene. The filtrate was washed with water and brine, dried over sodium sulfate, and after filtration volatiles were evaporated. Residual cyclohexylamine was removed by co-evaporation with toluene. This gave 186.6 g (98%) of product as a colorless liquid sufficiently pure for the next step. It contained less than 2% of bis-alkylation product (δ

3.60). $^1$H NMR δ 1.01-1.32 (m, 6H) and 1.53-1.93 (m, 5H) (c-Hex and N—H), 2.46 (tt, 1H, HC—N), 3.78 (s, 2H, CH$_2$Ph), 7.20-7.55 (m, 5H, Ph); $^{13}$C NMR δ 25.19, 26.40 and 33.77 (c-Hex), 51.25 (HC—N), 56.36 (CH$_2$Ph), 126.96, 128.23 and 128.52 (C—H, Ph), 141.23 (q-C, Ph).

Step 2: According to the general recipe disclosed in Example 1 using the crude product of Step 1 and 410 g of potassium bicarbonate in 500 mL of acetone and 1000 mL of water, then adding portion wise at ambient temperature 700 g of Oxone in 2.5 h (500 mL of ethyl acetate used in the first extraction now added at 60% completion of Oxone addition to counteract foaming due to precipitation of the nitrone formed), gave crude product, which was recrystallized from n-heptane-ethyl acetate (7:1 v/v). Yield: 110.3 g (60%) of nitrone as a single isomer. $^1$H NMR δ 1.11-1.39 (m, 3H), 1.60 (m, 1H) and 1.83-2.12 (m, 6H) (c-Hex), 3.79 (tt, 1H, HC—N), 7.28-7.38 (m, 3H, Ph), 7.38 (s, 1H, HC=N), 8.21 (m, 2H, Ph); $^{13}$C NMR δ 25.12, 25.12 and 31.22 (c-Hex), 75.69 (HC—N), 128.48, 128.59 and 130.06 (C—H, Ph), 130.95 (q-C, Ph), 132.19 (C=N).

Example 9 (Comparative):
(Z)—N-benzylidene-1-phenylmethanamine oxide

According to the general recipe disclosed in Example 1 using 101 g (0.51 mol) of dibenzylamine, 225 g of sodium bicarbonate in 400 mL each of acetone and water, then adding at ambient temperature portion wise 375 g of Oxone gave after work up crude nitrone in nearly quantitative yield. Recrystallization from n-heptane-ethyl acetate (1:1 v/v) gave a first crop of pure product. Evaporation of the filtrate followed by recrystallization gave a second crop. Combined yield: 99.8 g (92%). $^1$H NMR δ 5.02 (s, 2H, CH$_2$), 7.30-7.50 (m, 9H), 8.19 (m, 2H); $^{13}$C NMR δ 71.35 (CH$_2$N), 128.54, 128.69, 129.04, 129.04, 129.28 and 130.50 (each C—H, Ph), 130.58 and 133.43 (each q-C, Ph), 134.28 (HC=N).

Example 10 (Comparative):
(Z)—N-benzylideneaniline oxide

According to the general recipe disclosed in Example 1 from 122.8 g (0.67 mol) of N-phenylbenzylamine, 280 g of sodium bicarbonate in 450 mL each of acetone and water, then adding portion wise 480 g of Oxone (250 mL of ethyl acetate being added at 75% completion of the Oxone addition to counteract foaming due to precipitation of nitrone formed), gave after work up and crystallization from ethanol 44.8 g (34%) of a dark green nitrone. $^1$H NMR δ 7.38-7.48 (m, 6H), 7.72-7.77 (m, 2H) and 8.35-8.42 (m, 2H) (Ph), 7.90 (s, 1H, HC=N); $^{13}$C NMR δ 121.90, 128.79, 129.18, 129.30, 130.06 and 131.06 (each C—H, Ph), 130.86 and 149.26 (each q-C, Ph), 134.68 (HC=N).

Discussion of the Results of Examples 1-10

Surprisingly, it was found that aldonitrones C-substituted with a strong activating group, such as —CN, a carboxylic acid ester or a phosphonate ester, are easily and efficiently prepared at molar scale in good to excellent yields by oxidation using an acetone-water mixture containing only amine starting material and sodium- or potassium bicarbonate and feeding solid Oxone to the reaction. This procedure obviates the use of a phase transfer catalyst. Also, further organic solvents (less desirable from an environmental point of view) are not needed. The reaction can be carried out at significantly higher concentrations of the starting amine (typically 1.5 M up to 2 M), i.e. up to a tenfold or more of those hitherto reported. Products can be easily isolated by extraction and are sufficiently pure, so that they may be used directly without further purification.

In this way, C-cyano-substituted aldonitrones (Examples 1 and 5), C-ester-substituted aldonitrones (Examples 2 and 6), as well as C-phosphonate-substituted aldonitrones (Examples 3 and 7) are now accessible from their corresponding secondary amines in a more robust, scalable and economically viable oxidation method than known so far. Regarding C-cyano aldonitrones, it is surprising that the procedure does not lead to any primary amide nitrone co-product being formed, as could have been expected from literature (cf. Bose, D. S. et al. Syn. Commun. 1997, 27, 3119-23). Regarding C-ester- and C-phosphonate-substituted aldonitrones, their access via direct oxidation of the corresponding secondary amines is unprecedented and unexpected in view of the difficulties encountered with known oxidation methods, as described above.

In addition, the procedure works for C-phenyl aldonitrones, carrying a tertiary (Example 4), a secondary (Example 8) or a primary (Comparative Example 9) N-substituent, and also with an N-phenyl substituent (Comparative Example 10), thereby making this a versatile method for the preparation of a wide variety of aldonitrones.

Synthesis of Alkoxyamine Regulators of Formula (8A) by 1,3-di-tert-Radical Addition Examples 11-14 and 19-21 disclose from nitrones so obtained the direct preparation of representative alkoxyamines by 1,3-addition of 2 tertiary radicals, the latter preferably generated by thermal decomposition of azo-compounds according to the present invention. This is schematically illustrated by Reaction (II):

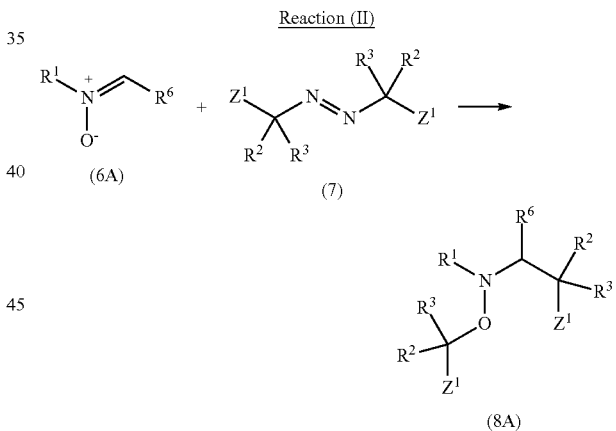

Comparative Examples 13, 15-17 and 22 list unsuccessful 1,3-di-tert-radical additions according to Reaction (II), because of limited conversion (Examples 16 and 17) and/or because of complete (Example 15A) or partial instability (Examples 13A, 16, 17 and 22A) of the targeted alkoxyamines under the reaction conditions. Comparative Examples 23 and 24 show preparation of known alkoxyamine compounds (Iwamura, M. et al. Bull. Chem. Soc. Jpn. 1970, 43, 856-60).

In detailing the invention for alkoxyamine synthesis, a choice was made for such azo-initiators that in the 1,3-di-tert-radical addition no further asymmetrical center in the alkoxyamine is created other than at the nitrone carbon. This is in no way meant to express a limitation in choice for other azo-initiator compounds: it merely serves to facilitate the demonstration of results. Thus, in the examples disclosed herein, use is made of following three azo-initiators of Formula (7): azobis(isobutyronitrile) (AIBN: $Z_1$=—CN, $R_2$=$R_3$=Me), azobis(α-ethylbutyronitrile) (AEBN: $Z_1$=—CN, $R_2$=$R_3$=Et), and azobis(methyl isobutyrate) (AIBMe: $Z_1$=$CO_2$Me, $R_2$=$R_3$=Me).

Example 11: 3-(tert-butyl(2-cyanopropan-2-yloxy)amino)-2,2-dimethylsuccinonitrile 18.92 g (0.15 mol) of nitrone prepared according to Example 1 and 40.64 g (1.65 equiv) of AIBN in 250 mL of toluene were stirred at 92° C. (bath temp) for 6 h. By evaporation of solvent, then recrystallization from isopropanol and cooling in a refrigerator, ca. 80% of alkoxyamine was recovered, contaminated by 10-20% of tetramethylsuccinonitrile (TMSN). When this material was dissolved in hot isopropanol and the solution slowly cooled to room temperature, pure alkoxyamine was obtained after filtration. Yield: 26.0 g (66%). $^1$H NMR δ 1.26 (s, 9H, t-Bu), 1.50, 1.61, 1.82 and 1.82 (each s, 3H, Me), 3.77 (s, 1H, HC—N); $^{13}$C NMR δ 24.51, 26.13, 28.18 and 28.18 (each Me), 26.61 (t-Bu), 36.25 ($\underline{C}$Me$_2$), 61.98 (HC—N), 63.08 (C—N), 76.58 (C—O), 113.46, 121.09 and 122.12 (each C≡N).

Note: steam stripping—an established practice in industry to remove TMSN—prior to a single crystallization from isopropanol could also be used to obtain pure alkoxyamine. The reaction could equally well be executed in toluene at reflux by feeding 1.3 equiv of AIBN in small portions. In Atom Transfer Radical Addition (ATRA) (procedure similar to Example 13B, now employing α-bromoisobutyronitrile) only 14% of the starting nitrone of Example 1 was converted to the alkoxyamine of Example 11, while the remainder of α-bromoisobutyronitrile was converted to TMSN.

Example 12: 3-(tert-butyl(3-cyanopentan-3-yloxy)amino)-2,2-diethylsuccinonitrile 5.68 g (45 mmol) of nitrone prepared according to Example 1 and 15.86 g (1.6 equiv) of AEBN in 75 mL of toluene were stirred at 86° C. (bath temp) overnight. $^1$H NMR indicated that conversion was ca. 90%. Evaporation of solvent, then recrystallization from isopropanol and cooling in a freezer, gave after filtration 5.40 g (38%) of the alkoxyamine as needles. $^1$H NMR δ 1.06, 1.11, 1.13 and 1.18 (each t, 3H, C$\underline{H_3}$CH$_2$), 1.28 (s, 9H, t-Bu), 1.55 (m, 1H), 1.86-2.15 (m, 5H) and 2.18-2.34 (m, 2H)(CH$_3$C$\underline{H_2}$), 4.04 (s, 1H, HC—N); $^{13}$C NMR δ 7.92, 8.28, 8.93 and 9.13 (each CH$_3$$\underline{C}$H$_2$), 25.28, 28.24, 29.32 and 30.64 (each CH$_3$$\underline{C}$H$_2$), 26.98 (t-Bu), 45.38 ($\underline{C}$Et$_2$), 58.70 (HC—N), 63.88 (C—N), 84.50 (C—O), 113.96, 119.45 and 120.64 (each C≡N).

Note: In one experiment 1.6 equiv of AEBN was added as a solid in small portions at 105° C. (bath temp) during 0.5 h, and heating was continued for 16 h: conversion was 90% to give a 1:1 mixture of alkoxyamine and NOH compound. 2-Ethylbut-2-enenitrile co-formed in the disproportionation, was observed as well (2 isomers δ 6.18 and 6.36 (each br q, CH=)).

Example 13: methyl 3-(tert-butyl(1-methoxy-2-methyl-1-oxopropan-2-yloxy)amino)-3-cyano-2,2-dimethylpropanoate Procedure A: 5.68 g (45 mmol) of the nitrone prepared according to Example 1 and 12.95 g (1.25 equiv) of dimethyl 2,2'-azobis(isobutyrate) (AIBMe) in 75 mL of toluene were stirred at 92° C. (bath temp) for 6 h. $^1$H NMR indicated 92% final conversion, 75% being the desired alkoxyamine and 17% consisting of a 1:1 mixture of 2-(tert-butyl)-4,4-dimethyl-5-oxoisoxazolidine-3-carbonitrile (δ 4.06 (s, 1H, H-3)), formed by the disproportionation of the alkoxyamine to NOH compound followed by cyclization, and methyl 2-(tert-butyl)-3-cyano-5-methylisoxazolidine-5-carboxylate 2.48, 3.20 and 3.96 (each dd, 1H, H-3 and H-4)), formed by dipolar cycloaddition of the starting nitrone to methyl methacrylate formed in the disproportionation. Isolation of the pure alkoxyamine by selective crystallization was not feasible.

Procedure B, using Atom Transfer Radical Addition (ATRA): To 7.57 g (60 mmol) of the nitrone prepared according to Example 1 and 30.2 g (2.9 equiv) of PMDETA (pentamethyldiethylenetriamine) in 100 mL of nitrogen-flushed methanol was added a mixture of 16.25 g of copper (I) bromide and 2.70 g of copper powder (2.6 equiv of copper). To the stirred solution was added at room temperature in 0.5 h a solution of 27.15 g (2.5 equiv) of methyl α-bromoisobutyrate in 20 mL of nitrogen-flushed methanol and the reaction was stirred overnight, when starting nitrone had been completely converted. The reaction was poured into 250 mL of 50%-saturated aqueous ammonium chloride and 250 mL of dichloromethane was added. After separation the water was extracted twice with 125-mL portions of dichloromethane. The combined organic fractions were washed twice with 50%-saturated aqueous ammonium chloride, once with brine, dried over sodium sulfate, and after filtration the solvents were removed in vacuum. The product was purified by flash column chromatography, followed by recrystallization from isopropanol to give a first crop of pure alkoxyamine. Evaporation of filtrate and again recrystallization from isopropanol gave a second crop. Combined yield: 12.62 g (64%) of white crystals. $^1$H NMR δ 1.11 (s, 9H, t-Bu), 1.28 (s, 6H), 1.46 (s, 3H) and 1.49 (s, 3H) (each Me), 3.66 and 3.68 (each s, 3H, OMe), 4.28 (s, 1H, HC—N); $^{13}$C NMR δ 21.77, 23.88, 24.28 and 24.45 (each Me), 26.46 (t-Bu), 46.61 ($\underline{C}$Me$_2$), 51.77 and 52.12 (each OMe), 61.29 (HC—N), 62.82 (C—N), 78.68 (C—O), 115.80 (C≡N), 174.57 and 175.19 (each C=O).

Example 14: methyl 2-(tert-butyl(2-cyanopropan-2-yloxy)amino)-3-cyano-3-methylbutanoate 23.88 g (0.15 mol) of the nitrone prepared according to Example 2 and 40.64 g (1.65 equiv) of AIBN in 250 mL of toluene were stirred at 92° C. (bath temp) for 6 h. $^1$H NMR indicated complete conversion of starting nitrone to a 96:4 mixture of alkoxyamine and a single cycloadduct (identified by comparison to an authentic sample: cf. Note below). Evaporation of the solvent, then recrystallization from isopropanol and cooling in a refrigerator gave ca. 80% of the alkoxyamine, contaminated by 20-30% of TMSN. Pure alkoxyamine was obtained by 2 to 3 further recrystallizations from isopropanol as white crystals in 25.80 g (58%). $^1$H NMR δ 1.26 (s, 9H, t-Bu), 1.35, 1.48, 1.71 and 1.82 (each s, 3H, Me), 3.55 (s, 1H, HC—N), 3.75 (s, 3H, OMe); $^{13}$C NMR δ 25.68, 26.22, 26.45 and 28.42 (each Me), 27.66 (t-Bu), 34.33 ($\underline{C}$Me$_2$), 51.61 (OMe), 62.92 (C—N), 71.33 (HC—N), 77.09 (C—O), 121.35 and 124.59 (each C≡N), 166.77 (C=O).

Note: at 105° C. the ratio of alkoxyamine to cycloadduct was 92:8, while 4% of the NOH disproportionation product was now observed: δ 5.67 (br, NOH) and 3.52 (HC—N). Heating starting nitrone with 2 equiv of methacrylonitrile at 90° C. in toluene for 6 h gave full conversion with concomitant formation of 2 diastereoisomeric cycloadducts in a ratio of 95:5. Major: $^1$H NMR δ 1.14 (s, 9H, t-Bu), 1.69 (s, 3H, Me), 2.65, 2.90 and 4.09 (each dd, 1H, H-3 and H-4), 3.74 (s, 3H, OMe).

Example 15: dimethyl 3-(tert-butyl((1-methoxy-2-methyl-1-oxopropan-2-yl)oxy)amino)-2,2-dimethyl-succinate Procedure A: 7.16 g (45 mmol) of nitrone prepared according to Example 2 and 12.95 g (1.25 equiv) of AIBMe in 75 mL of toluene were stirred at 92° C. (bath temp) for 6 h. $^1$H NMR analysis indicated that all nitrone had been converted, but that none of the desired alkoxyamine (δ 4.26 (HC—N)—see below) was present. The main component accounting for 80% of converted nitrone was methyl 2-(tert-butyl)-4,4-dimethyl-5-oxoisoxazolidine-3-carboxylate (δ 1.12 (s, 9H, t-Bu), 1.24 and 1.34 (each s, 3H, Me), 3.75 (s, 3H, OMe), and 3.85 (s, 1H, H-3)).

In part, this component was formed by disproportionation of alkoxyamine to NOH, followed by cyclization. MMA co-formed in the disproportionation, had consumed 20% of nitrone by 1,3-dipolar cycloaddition to give 2 isomeric (ratio 9:1) dimethyl 2-(tert-butyl)-5-methylisoxazolidine-3,5-dicarboxylates (major δ 1.06 (s, 9H, t-Bu), 1.53 (s, 3H, 5-Me), 2.39 and 2.96 (each dd, 1H, H-4), 3.71 and 3.71 (each s, 3H, OMe), H-3 obscured). MMA had also inserted into alkoxyamine C—O bonds, but new alkoxyamines so formed likewise underwent disproportionation to afford the same cyclization product (accounting for 30% of its formation) and the known (cf. Wilkinson, T. S. et al. *J. Coll. Interfac. Sci.* 2001, 237, 21-7) MMA unsaturated dimer dimethyl 2,2-dimethyl-4-methylenepentanedioate (δ 1.13 (s, 6H, Me$_2$), 2.58 (d, 2H, CH$_2$), 3.61 and 3.70 (each s, 3H, OMe), 5.49 (br s) and 6.18 (d) (=CH$_2$)) and presumably unsaturated MMA trimer (δ 2.51 (m, CH$_2$), 5.46 (br s) and 6.16 (d) (=CH$_2$)), with the ratio of dimer to trimer being ca. 7:1. Isolation was not attempted.

Procedure B, Using Atom Transfer Radical Addition (ATRA):

To 9.55 g (60 mmol) of the nitrone prepared according to Example 2 and 30.2 g (2.9 equiv) of PMDETA (pentamethyldiethylenetriamine in 100 mL of nitrogen-flushed methanol was added a mixture of 16.25 g copper(I) bromide and 2.70 g of copper powder (2.6 equiv of copper). To the stirred solution was added at room temperature in 0.5 h a solution of 27.15 g (2.5 equiv) of methyl α-bromoisobutyrate in 20 mL of nitrogen-flushed methanol and the reaction was stirred overnight, when starting nitrone had been completely converted. The reaction was poured into 250 mL of 50%-saturated aqueous ammonium chloride and 250 mL of dichloromethane was added. After separation the water was extracted twice with 125-mL portions of dichloromethane. The combined organic fractions were washed twice with 50%-saturated aqueous ammonium chloride, once with brine, dried over sodium sulfate, and after filtration solvents were removed in vacuum. $^1$H NMR analysis indicated that beside dimethyl 2,2,3,3-tetramethylsuccinate (δ 1.20, 3.60), the desired alkoxyamine was the main component (δ 1.14 (s, 9H, t-Bu), 1.20, 1.31, 1.47 and 1.51 (each s, 3H, Me), 3.62, 3.62 and 3.65 (each s, 3H, OMe), 4.26 (s, 1H, CH—N)). However, ca. 30% of the alkoxyamine initially formed, had been converted into dimethyl 2-(tert-butyl(hydroxy)amino)-2-methoxy-3,3-dimethylsuccinate: δ 1.14 (s, 9H, t-Bu), 1.42 and 1.45 (each s, 3H, Me), 3.42, 3.66 and 3.71 (each s, 3H, OMe), 4.9 (br, 1H, OH). The targeted alkoxyamine could not be isolated in a pure state.

Note: the byproduct dimethyl 2-(tert-butyl(hydroxy)amino)-2-methoxy-3,3-dimethylsuccinate is the net outcome of a base-induced transformation of an alkoxyamine of Formula (8) into a nitrone of Formula (1B) (as disclosed below), followed by methanol addition to the nitrone.

Example 16: diethyl (1-(tert-butyl((2-cyanopropan-2-yl)oxy)amino)-2-cyano-2-methylpropyl)phosphonate 10.67 g (45 mmol) of nitrone prepared according to Example 3 and 11.82 g (1.6 equiv) of AIBN in 75 mL of toluene were stirred at 92° C. (bath temp) for 6 h. $^{31}$P NMR analysis indicated that conversion was ca. 60% at most: while the alkoxyamine (δ 20.68) was formed, its presence in the reaction mixture accounted for less than 50% of converted starting nitrone, the major components having shifts reminiscent of phosphite- or phosphate-type products. Higher AIBN loadings and/or higher temperatures were not beneficial: while conversion of starting nitrone was increased, the relative proportion of what was presumably the targeted alkoxyamine product decreased even further.

Example 17: 3-(tert-butyl((2-cyanopropan-2-yl)oxy)amino)-2,2-dimethyl-3-phenylpropanenitrile 7.98 g (45 mmol) of nitrone prepared according to Example 4 and 11.86 g (1.6 equiv) of AIBN in 75 mL of toluene were stirred at 92° C. (bath temp) for 6 h. $^1$H NMR analysis of the reaction mixture indicated that conversion was only 24% at best and targeted alkoxyamine (δ 3.72) was present in only 7%. Beside a small amount of an unidentified component (δ 4.09 2%), the main product (present in 15%) was presumably the NOH compound 3-(tert-butyl(hydroxy)amino)-2,2-dimethyl-3-phenylpropanenitrile (δ 0.96 (t-Bu), 3.62 (CH—N), 4.73 (OH)), formed upon disproportionation of the alkoxyamine. Methacrylonitrile co-formed in the disproportionation, had preferentially inserted into the alkoxyamine C—O bond (rather than having reacted with the nitrone in a 1,3-dipolar cycloaddition), but new alkoxyamines so formed underwent disproportionation completely: 2,2-dimethyl-4-methylenepentanedinitrile (δ 5.99 and 6.15 (=CH$_2$)) co-formed in their disproportionation, was present in 3%. Isolation was not attempted.

Example 18: 3-(((2-cyanopropan-2-yl)oxy)(cyclohexyl)amino)-2,2-dimethylsuccinonitrile 45.66 g (0.3 mol) of nitrone prepared according to Example 5 and 81.3 g (1.65 equiv) of AIBN in 500 mL of isopropanol were stirred for 6 h at 92° C. (oil bath temperature). Heating and stirring were switched off, and the mixture was allowed to slowly cool to room temperature. The crystals were collected by filtration, washed with isopropanol and air dried. Yield: 76.15 g (88%) of pure alkoxyamine as white crystals. $^1$H NMR δ 0.85-1.75 (m, 9H) and 2.45 (m, 1H) (c-Hex), 1.19, 1.20, 1.28 and 1.38 (each s, 3H, Me), 3.36 (br tt, 1H, HC—N, c-Hex), 3.54 (br s, 1H, HC—N); $^{13}$C NMR δ 24.92, 25.85, 26.03, 26.03, 26.30, 26.45, 27.08, 27.58 and 32.87 (c-Hex and 4 Me), 36.25 (CMe$_2$), 63.07 and 65.77 (each CH—N), 73.60 (C—O), 114.86, 121.55 and 121.68 (each C≡N).

Note: The reaction could equally well be executed with similar yields, but more rapidly and consuming less azo-initiator, by feeding solid AIBN (1.3 equiv) in small portions to a refluxing solution of nitrone in: 1) toluene at 105° C. prior to evaporation and a single crystallization from isopropanol; or in 2) 1-butanol at 115° C., followed by slowly cooling to room temperature and collecting the crystals of pure alkoxyamine directly.

Example 19: ethyl 3-cyano-2-(((2-cyanopropan-2-yl)oxy)(cyclohexyl)amino)-3-methylbutanoate 29.9 g (0.15 mol) of nitrone prepared according to Example 6 and 40.6 g (1.65 equiv) of AIBN in 250 mL of toluene were stirred for 6 h at 92° C. (oil bath temperature). Up to 90% of the TMSN in the crude reaction mixture could be removed by steam stripping, but the alkoxyamine though crystalline could not be obtained free from TMSN by crystallization. $^1$H NMR δ 1.00-1.14 (m, 1H), 1.25-1.60 (m, 5H), 1.67-1.76 (m, 2H) and 1.86-1.96 (m, 2H) (c-Hex), 1.08 (br t, 3H, OEt), 1.20, 1.34, 1.43 and 1.46 (each s, 3H, 4 Me), 3.63 and 3.67 (each br, 1H, HC—N), 3.97-4.05 (m, 2H, OEt); $^{13}$C NMR δ 14.14 (OEt), 25.72, 26.39, 26.49, 26.58, 26.75, 27.10, 29.59 and 33.40 (br) (c-Hex and 4 Me), 34.49 (CMe$_2$), 61.10 (OEt), 64.15 (br) and 73.60 (each HC—N), 73.48 (C—O), 121.91 and 123.09 (each C≡N), 168.56 (C=O).

Example 20: diethyl (2-cyano-1-(((2-cyanopropan-2-yl)oxy)(cyclohexyl)amino)-2-methylpropyl)phosphonate 39.5 g (0.15 mol) of nitrone prepared according to Example 7 and 41.85 g (1.7 equiv) of AIBN in 250 mL of toluene were stirred for 6 h at 92° C. (oil bath temperature). Up to 90% of TMSN present in the crude reaction mixture could be removed by steam stripping, but pure alkoxyamine could not be obtained, as the product resisted all attempts at crystallization.

Example 21: 3-(((2-cyanopropan-2-yl)oxy)(cyclohexyl)amino)-2,2-dimethyl-3-phenylpropanenitrile 24.39 g (0.12 mol) of nitrone prepared according to Example 8 and 32.51 g (1.65 equiv) of AIBN in 250 mL of toluene were stirred at 92° C. (bath temp) for 6 h. Evaporation of solvent, re-dissolving the product in hot isopropanol and slowly cooling to room temperature afforded a first crop. Evaporation of filtrate and recrystallization from methanol afforded a second. Total yield: 29.44 g (72%) of crystalline alkoxyamine. $^1$H NMR δ 0.74-1.75 (m, 10H, c-Hex), 0.91, 1.38, 1.49 and 1.57 (each s, 3H, Me), 3.54 (tt, 1H, HC—N), 3.5-4.2 (br, 1H, HCPh), 7.03-7.14 (m, 3H) and 7.55-7.65 (m, 2H) (Ph); $^{13}$C NMR δ 26.39, 26.47, 26.71, 26.81, 27.26, 27.39, 28.32 (br), 29.31 and 34.03 (br) (c-Hex and 4 Me), 35.53 (CMe$_2$), 63.69 (C—H, c-Hex), 72.37 (C—O), 72.25 (br, CHPh), 122.47 and 124.84 (each C≡N), 128.40, 128.54 and 131.13 (each C—H, Ph), 136.97 (br q-C, Ph).

Note: in some cases collected product still contained trace amounts of TMSN: these were effectively removed by a final crystallization from isopropanol. The reaction could equally well be executed in toluene at reflux by feeding 1.3 equiv of AIBN in small portions. Alternatively, steam stripping—an established industrial practice to remove TMSN—followed by a single recrystallization from isopropanol could be used for obtaining pure alkoxyamine.

Example 22: methyl 3-(cyclohexyl((1-methoxy-2-methyl-1-oxopropan-2-yl)oxy)amino)-2,2-dimethyl-3-phenylpropanoate Procedure A: 9.15 g (45 mmol) of nitrone prepared according to Example 8 and 16.58 g (1.6 equiv) of AIBMe in 75 mL of toluene were stirred at 92° C. (bath temp) for 6 h. $^1$H NMR analysis indicated that conversion was close to 90% and that the targeted alkoxyamine was the main component. However, 20% of alkoxyamine had undergone disproportionation to NOH followed by cyclization to give 2-cyclohexyl-4,4-dimethyl-3-phenylisoxazolidin-5-one (δ 2.71 (tt, 1H, CH—N), and 4.14 (s, 1H, H-3)). MMA co-formed in the disproportionation, had preferentially inserted into other alkoxyamine C—O bonds (rather than reacting with nitrone in a 1,3-dipolar cycloaddition), but new alkoxyamines so formed underwent disproportionation completely to give the same cyclization product as above (accounting for ca. 40% of its formation) and the known (cf. Wilkinson, T. S. et al. *J. Coll. Interfac. Sci.* 2001, 237, 21-7) MMA unsaturated dimer dimethyl 2,2-dimethyl-4-methyl-enepentanedioate (δ 2.58 (d, 2H, CH$_2$), 5.49 (br s) and 6.18 (d) (=CH$_2$)) and presumably unsaturated MMA trimer (δ 5.46 (br s) and 6.16 (d) (=CH$_2$)). Isolation by fractional crystallization failed.

Procedure B, Using Atom Transfer Radical Addition (ATRA): To 12.20 g (60 mmol) of nitrone prepared according to Example 8 and 30.2 g (2.9 equiv) of PMDETA (pentamethyldiethylenetriamine) in 100 mL of nitrogen-flushed methanol was added a mixture of 16.25 g of copper (I) bromide and 2.70 g of copper powder (2.6 equiv of copper). To the stirred solution was added at room temperature in 0.5 h a solution of 27.15 g (2.5 equiv) of methyl α-bromoisobutyrate in 20 mL of nitrogen-flushed methanol and the reaction was stirred overnight. The reaction was poured into 250 mL of 50%-saturated aqueous ammonium chloride and 250 mL of dichloromethane was then added. After separation the water was extracted twice with 125-mL portions of dichloromethane. The combined organic fractions were washed twice with 50%-saturated aqueous solution of ammonium chloride, once with brine, dried over sodium sulfate, and solvents were removed after filtration removed in vacuum. $^1$H NMR analysis showed that all methyl α-bromoisobutyrate had been converted, but mostly to dimethyl 2,2,3,3-tetramethylsuccinate, while 80% of nitrone had not reacted: only 20% had been converted to the targeted alkoxyamine. Isolation was not attempted

Example 23 (Comparative): 3-(benzyl((2-cyanopropan-2-yl)oxy)amino)-2,2-dimethyl-3-phenylpropanenitrile 9.51 g (45 mmol) of nitrone prepared according to Example 9 and 11.82 g (1.6 equiv) of AIBN in 90 mL of toluene were stirred for 6 h at 92° C. (bath temp). Evaporation of solvent and recrystallization from methanol gave 11.47 g (73%) of alkoxyamine as fine needles. $^1$H NMR δ 0.89, 1.05 (br), 1.21 and 1.63 (each s, 3H, Me), 3.33 and 4.64 (each d, 1H, CH$_2$Ph), 4.00 (br s, 1H, HC—N), 6.79-7.22 (m, 8H) and 7.57 (br d, 2H) (Ph); $^{13}$C NMR δ 25.81, 27.40, 27.52 and 27.96 (each Me), 35.08 (CMe$_2$), 59.98 (CH$_2$—N), 72.49 (C—O), 75.99 (CH—N), 122.36 and 124.92 (each C≡N), 128.00, 128.52, 128.64, 128.86, 130.77 and 131.77 (each C—H, Ph), 134.26 and 137.96 (each q-C, Ph).

Note: This compound (but then reported to be isolated in 46% yield) is known from the work of Iwamura, S. et al. *Bull. Chem. Soc. Jpn.* 1970, 43, 856-60.

Example 24 (Comparative): 3-(((2-cyanopropan-2-yl)oxy)(phenyl)amino)-2,2-dimethyl-3-phenylpropanenitrile 8.88 g (45 mmol) of nitrone prepared according to Example 10 and 11.82 g (1.6 equiv) of AIBN in 90 mL of toluene were stirred for 6 h at 92° C. (bath temp). Evaporating the solvent and recrystallizing twice from methanol gave 10.45 g (70%) of alkoxyamine as yellow-green crystals. $^1$H NMR δ 0.90, 1.17, 1.52 and 1.73 (each s, 3H, Me), 3.46 (br s, 1H, HC—N), 6.78-7.08 (m, 8H) and 7.14-7.19 (m, 2H) (Ph); $^{13}$C NMR δ 26.32, 27.64, 27.91 and 27.91 (each Me), 35.26 (CMe$_2$), 75.35 (C=O), 86.64 (CH—N), 121.39 and 124.36 (each C≡N), 123.99, 126.59, 128.02, 128.59, 128.74 and 131.68 (each C—H, Ph), 133.99 and 151.87 (each q-C, Ph).

Note: This compound (but then reported to be isolated in 63% yield) is known from the work of Iwamura, S. et al. *Bull. Chem. Soc. Jpn.* 1970, 43, 856-60.

Discussion of the Results of Examples 11-24

With C-cyano-N-tert-butylnitrone and 1.65 equiv of AIBN at 92° C. (Example 11), quantitative 1,3-di-tert-radical addition occurs, the alkoxyamine being the only product present (beside TMSN). Even in toluene at reflux, the alkoxyamine is the only product formed: no evidence for disproportionation to give NOH compound is found. Use of AEBN (Example 12) at 86° C. produces targeted alkoxyamine as the main component along with a small amount (4%) of NOH compound, but when performed at 105° C. alkoxyamine and NOH compounds are present in equal amount. In both cases the alkoxyamines are easily obtained pure by fractional crystallization.

Also for a sterically more congested C-ester-substituted N-tert-butylnitrone with 1.65 equiv of AIBN at 92° C. (Example 14), 1,3-di-tert-radical addition is the dominant pathway, accounting for 96% of nitrone consumed: the remaining 4% present is a single 1,3-dipolar cycloadduct of nitrone to methacrylonitrile. In toluene at 105° C., 4% of the NOH compound is also formed. Again, the alkoxyamine is easily obtained pure by fractional crystallization.

By contrast, reaction of C-phenyl-N-tert-butylnitrone (PBN) with 1.6 equiv of AIBN at 92° C. (Example 17) gives only 25% conversion of starting nitrone, the main product (15%) being the NOH disproportionation compound. When replacing C-phenyl with a sterically less demanding and stronger activating C-phosphonate (Example 16), conversion of starting nitrone is increased, but only to 60%. Furthermore, what is presumed to be the targeted alkoxyamine accounts for less than 50% of converted nitrone and the product does not appear to be stable under the reaction conditions.

Thus, examples on 1,3-di-tert-radical addition of cyano-functional azo-initiators AIBN and AEBN to N-tert-alkyl aldonitrones, C-substituted by an activating or conjugating group, teach that only —CN and ester groups are effective and can produce in good yields alkoxyamine regulator compounds, with no, or hardly any, disproportionation when using AIBN.

Use of AIBN at 92° C. with cyclohexyl as example of an N-secondary substituent, produces targeted alkoxyamine regulator compounds as the sole product not only for nitrones, C-substituted with —CN (Example 18) or an ester group (Example 19), but now also for those with a phosphonate (Example 20) or a phenyl (Example 21). Remarkably, even in toluene at reflux no sign of NOH compound, formed by disproportionation of an initially formed alkoxyamine, can be detected for any of these systems.

The addition of AIBN to C-phenylnitrones, carrying an N-benzyl (Comparative Example 23) or an N-phenyl (Comparative Example 24) substituent, readily occurs in toluene at 92° C. and alkoxyamines are easily obtained pure by crystallization in good yields. Both compounds are known from the work of Iwamura, S. et al. (*Bull. Chem. Soc. Jpn.* 1970, 43, 856-60).

In contrast to the versatility when using AIBN (and other cyano-functional azo-initiators) in preparing alkoxyamines of Formula (8) by 1,3-di-tert-radical addition to nitrones of Formula (6), the use of ester-substituted azo-initiator AIBMe gives mixed results. While C-cyano-N-tert-butyl- (Example 13A) and C-phenyl-N-cyclohexylnitrone (Example 22A) with AIBMe in toluene at 92° C. still give targeted alkoxyamines as the major component, the C-ester-substituted N-tert-butylnitrone, while fully converted, shows none (Example 15A). Instead, 80% of nitrone is found as methyl 2-(tert-butyl)-4,4-dimethyl-5-oxoisoxazolidine-3-carboxylate of Formula (9) (R$^1$=t-Bu, R$^2$=R$^3$=Me, R$^6$=C(O)OMe), formed by disproportionation of an initially formed alkoxyamine to NOH compound (and MMA), followed by cyclization. This side reaction accounts for 17% and 20% of the converted nitrone in Examples 13A and 22A, respectively, and prevents an efficient isolation of the alkoxyamine regulator in these cases.

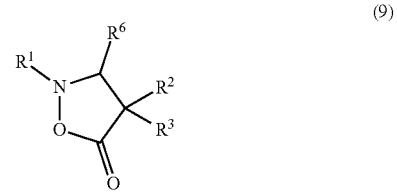

(9)

Therefore, a process for preparing alkoxyamines of Formula (8A) by 1,3-di-tert-radical addition of an ester-functional azo-initiator such as AIBMe to an aldonitrone of Formula (6A) is less preferred.

An alternative process for preparing of these alkoxyamines, i.e. Atom Transfer 1,3-di-tert-Radical Addition (ATRA) at ambient temperature (ca. 25° C.) using methyl α-bromoisobutyrate as radical source, can be envisaged. For the C-cyano-N-tert-butylnitrone the targeted alkoxyamine is obtainable as a pure compound (Example 13). However, while for the C-ester-substituted N-tert-butylnitrone complete conversion is achieved, formation of a side product prevents isolation of the targeted alkoxyamine in a pure state (Example 15B). For the C-phenyl-substituted N-cyclohexylnitrone conversion to alkoxyamine is limited to 20% at best (Example 22B).

Thus, it has thus been demonstrated that the preparation of alkoxyamines may be done by reaction of an aldonitrone of Formula (6A) with an azo-initiator compound of Formula (7) to form the corresponding alkoxyamine of Formula (8A).

Synthesis of Nitrones of Formula (1C)

Examples 25-36 illustrate two methods for preparing the nitrones of Formula (1C).

Examples 25-33 disclose the first method, i.e., the transformation of alkoxyamines of Formula (8A) (disclosed in Examples 11-24) by base treatment to specific nitrones of Formula (1C). The transformation is schematically illustrated by Reaction (III):

Reaction (III)

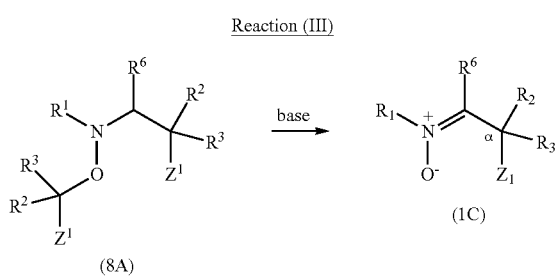

Examples 25-31 were successful, while Comparative Examples 32 and 33 were not.

Less preferred from an industrial perspective is preparation of nitrone (1C) from a hydroxylamine compound by an addition (Example 34) or a condensation (Examples 35 and 36) reaction. This method is of limited value, as pricing of the hydroxylamine compounds (when commercially available) is prohibitive for the intended end-uses. Furthermore, within the context of the present invention, only nitrones of general Formula (1C), carrying a carboxylic ester group as $R^6$, are accessible in this manner.

Nonetheless, the product of Example 34 was specifically included, as it represents a nitrone of general Formula (1C), carrying only an ester substituent as $Z^1$ at the α-carbon in the nitrone ($R^2=R^3=H$). Structurally related nitrones prepared according to the Examples 35 and 36 lack an activating function in the α-position and serve as comparative examples in polymerization experiments.

Example 25: (E)-N-(1,2-dicyano-2-methylpropylidene)cyclohexanamine oxide

To a suspension of 72.1 g (0.25 mol) of the alkoxyamine prepared according to Example 18 in 200 mL of DMF was added, whilst stirring and cooling in a water bath, 0.42 g and after 15 min another 0.42 g (3 mol % of base in total) of solid potassium tert-butoxide. All alkoxyamine rapidly dissolved and a clear yellow solution was formed. After 3 h the reaction was poured into an ice-cold mixture of 250 mL of 50%-saturated aqueous ammonium chloride and 150 mL of tert-butyl methyl ether. The layers were separated and the aqueous layer was extracted twice with 75 mL portions of tert-butyl methyl ether. The collected organic fractions were washed twice with water, once with brine, dried over sodium sulfate, and after filtration solvent was removed under vacuum. The crude product obtained in near quantitative yield as a yellow liquid, contained ca. 5% of an unknown compound tentatively assigned as acetone cyanohydrin ($^1$H NMR δ 1.58 (s); $^{13}$C NMR δ 29.41). Recrystallization from n-pentane gave a first crop of pure product. Evaporation of the filtrate followed by recrystallization gave a second. Total yield: 43.7 g (80%) of light yellow crystals. $^1$H NMR δ 1.20-1.85 (m, 10H, c-Hex), 1.62 (s, 6H, Me$_2$), 3.68 (tt, 1H, HC—N); $^{13}$C NMR δ 23.88, 25.34 and 33.15 (c-Hex), 24.73 (C$\underline{Me}_2$), 40.44 ($\underline{C}Me_2$), 67.39 (CH—N), 108.17 and 120.29 (each C≡N), 140.27 (C=N).

Note: This transformation could equally well be carried out in THF using 10 mol % of DBU (1,8-diazabicyclo[5.4.0]undec-7-ene) as a base catalyst and stirring the reaction overnight. Work up and re-crystallization as before afforded pure product in 78% yield.

Example 26: (E)-N-(1,2-dicyano-2-methylpropylidene)-2-methylpropan-2-amine oxide As in Example 25, using 15.74 g (60 mmol) of the alkoxyamine prepared according to Example 11, gave after work up 10.94 g (94%) of the crude nitrone product as a yellow liquid, containing 6% of an unknown compound tentatively assigned as acetone cyanohydrin ($^1$H NMR δ 1.58 (s); $^{13}$C NMR δ 29.41). Further purification was achieved by recrystallization from n-pentane in the freezer and filtration at low temperature. The nitrone is a yellow liquid at ambient temperature. $^1$H NMR δ 1.39 (s, 9H, t-Bu), 1.60 (s, 6H, CMe$_2$); $^{13}$C NMR δ 24.65 (C$\underline{Me}_2$), 29.13 (t-Bu), 42.42 ($\underline{C}Me_2$), 59.30 (C—N), 109.77 and 120.46 (each C≡N), 137.63 (C=N).

Example 27: (E)-N-(1-cyano-3-methoxy-2,2-dimethyl-3-oxopropylidene)-2-methylpropan-2-amine oxide As in Example 25, using 6.57 g (20 mmol) of the alkoxyamine prepared according to Example 13 and in total 0.225 g (10 mol %) of potassium tert-butoxide in 50 mL of DMF, gave after stirring overnight and work up 4.04 g (89%) of nitrone as a colourless liquid. $^1$H NMR δ 1.35 (s, 9H, t-Bu), 1.41 (s, 6H, CMe$_2$), 3.69 (s, 3H, OMe); $^{13}$C NMR δ 23.04 (C$\underline{Me}_2$), 29.19 (t-Bu), 52.05 ($\underline{C}Me_2$), 52.72 (OMe), 58.26 (C—N), 111.31 (C≡N), 141.11 (C=N), 174.06 (C=O).

Example 28: (E)-N-(3-cyano-1-methoxy-3-methyl-1-oxobutan-2-ylidene)-2-methylpropan-2-amine oxide As in Example 25, using 8.86 g (30 mmol) of the alkoxyamine prepared according to Example 14, but now using a stoichiometric amount of sodium methoxide in 50 mL of DMF and stirring overnight, gave after work up 5.78 g (85%) of nitrone as a slightly yellow liquid. $^1$H NMR δ 1.25 (s, 9H, t-Bu), 1.56 (s, 6H, CMe$_2$), 3.84 (s, 3H, OMe); $^{13}$C NMR δ 25.71 (C$\underline{Me}_2$), 29.61 (t-Bu), 40.26 ($\underline{C}Me_2$), 52.17 (OMe), 57.69 (C—N), 122.45 (C≡N), 137.72 (C=N), 166.38 (C=O).

Example 29: (E)-N-(3-cyano-1-ethoxy-3-methyl-1-oxobutan-2-ylidene)cyclohexanamine oxide As in Example 25, using 17.10 g (net 50 mmol) of the alkoxyamine prepared according to Example 19, but now using a stoichiometric amount of sodium ethoxide in 100 mL of DMF and stirring overnight, gave after work up 11.24 g (82%) nitrone product that contains ca. 5% of TMSN (present in the starting material). This material can be used as such in polymerizations, as TMSN will not interfere. Analytically pure nitrone was obtained after column chromatography as a slightly yellow liquid in 9.90 g (74%). $^1$H NMR δ 1.32 (t, 3H, OEt), 1.54 (s, 6H, CMe$_2$), 1.18-1.26 (m, 3H), 1.38-1.47 (m, 2H), 1.52-1.61 (m, 3H) and 1.68-1.76 (m, 2H) (c-Hex), 3.17 (m, 1H, HC—N), 4.31 (q, 2H, OEt); $^{13}$C NMR δ 14.29 (OEt), 24.05, 25.52 and 33.31 (c-Hex), 25.52 (C$\underline{Me}_2$), 38.78 ($\underline{C}Me_2$), 61.68 (OEt), 63.38 (HC—N), 122.11 (C≡N), 157.95 (C=N), 163.50 (C=O).

Example 30: (E)-N-(2-cyano-1-(diethoxyphosphoryl)-2-methylpropylidene)cyclohexanamine oxide As in Example 25, using 12.20 g (net 30 mmol) of alkoxyamine prepared according to Example 20, but now using a stoichiometric amount of sodium ethoxide in 50 mL of DMF and stirring overnight, gave after work up 8.20 g (80%) of (E) nitrone, containing ca. 12% of (Z) isomer and 5% of TMSN (present in the starting material). This material can be used as such in polymerizations, as TMSN will not interfere. Pure nitrone was obtained after column chromatography as a colourless liquid in 7.00 g (74%) as a 92:8 mixture of (E) and (Z) isomers. Main (E) isomer: $^1$H NMR δ 1.32 (t, 6H, OEt), 1.57 (s, 6H, CMe$_2$), 1.18-1.36 (m, 3H), 1.38-1.47 (m, 2H), 1.52-1.63 (m, 3H) and 1.70-1.78 (m, 2H) (c-Hex), 4.07 (m, 1H, HC—N), 4.31 (m, 4H, OEt); $^{13}$C NMR δ 16.51 (d, $^3J_{CP}$=6, OEt), 23.90, 25.74 and 33.32 (c-Hex), 25.69 (CMe$_2$), 42.00 (d, $^2J_{CP}$=40, CMe$_2$), 62.65 (d, $^2J_{CP}$=6, OEt), 63.09 (d, $^3J_{CP}$=15, HC—N), 123.00 (s, $^3J_{CP}$=0, C≡N), 158.68 (d, $^1J_{CP}$=141, C=N); $^{31}$P NMR δ 1.70; minor (Z) isomer partial data: $^1$H NMR δ 1.49 (s, 6H, CMe$_2$), 4.80 (m, 1H, HC—N); $^{13}$C NMR δ 16.51 (OEt), 23.57 (CMe$_2$), 23.92, 25.66 and 33.2 (c-Hex), 44.40 (s, $^2J_{CP}$=0, CMe$_2$), 62.61 (d, $^2J_{CP}$=6, OEt), 62.92 (d, $^3J_{CP}$=15, HC—N), 121.55 (s, $^3J_{CP}$=0, C≡N), 159.09 (d, $^1J_{CP}$=141, C=N); $^{31}$P NMR δ 0.64.

Example 31: (Z)—N-(2-cyano-2-methyl-1-phenyl-propylidene)cyclohexanamine oxide As in Example 25, using 10.18 g (30 mmol) of alkoxyamine prepared according to Example 21 and 7.40 g (2.2 equiv) of potassium tert-butoxide in 50 mL of DMF and stirring overnight, gave after work up 7.30 g (90%) of crude nitrone as a reddish liquid that crystallized on standing. $^1$H NMR δ 1.00-1.11 (m, 2H), 1.15-1.25 (m, 1H), 1.38-1.55 (m, 5H) and 1.63-1.71 (m, 2H) (c-Hex), 1.51 (s, 6H, CMe$_2$), 2.89 (tt, 1H, HC—N), 7.03-7.07 (m, 2H) and 7.35-7.43 (m, 3H) (Ph); $^{13}$C NMR δ 24.15, 25.73 and 33.54 (c-Hex), 25.89 (CMe$_2$), 41.84 (CMe$_2$), 60.99 (HC—N), 123.64 (C≡N), 127.47, 128.57 and 128.72 (each C—H, Ph), 135.16 (q-C, Ph), 165.56 (C=N).

Example 32 (Comparative): (Z)—N-(2-cyano-2-methyl-1-phenylpropylidene)-1-phenylmethanamine oxide As in Example 25, using 10.42 g (30 mmol) of alkoxyamine prepared according to Example 23 and 7.40 g (2.2 equiv) of potassium tert-butoxide in 50 mL of DMF and stirring overnight, gave after work up 6.85 g (82%) of a reddish liquid. However, the product contained none of the desired nitrone, but was its isomer (Z)—N-benzylidene-2-cyano-2-methyl-1-phenylpropan-1-amine oxide: $^1$H NMR δ 1.37 and 1.42 (each s, 3H, Me), 4.23 (s, 1H, HC—N), 7.26-7.48 (m, 6H), 7.55 (br d, 2H) and 7.87 (m, 2H) (Ph), 8.34 (s, 1H, HC=N); $^{13}$C NMR δ 23.83 and 24.37 (each Me), 34.44 (CMe$_2$), 80.72 (HC—N), 124.02 (C≡N), 128.07, 128.19, 128.55, 128.57, 128.57 and 131.11 (each C—H, Ph), 135.75 and 139.15 (each q-C, Ph), 162.29 (HC=N). Isolation was not attempted.

Example 33 (Comparative): (Z)—N-(2-cyano-2-methyl-1-phenyl-propylidene)aniline oxide As in Example 25, using 10.0 g (30 mmol) of the alkoxyamine prepared according to Example 24 and 7.40 g (2.2 equiv) of potassium tert-butoxide in 50 mL of DMF and stirring overnight. $^1$H NMR analysis indicated that the desired product was formed, but the product had partially hydrolysed to 2,2-dimethyl-3-oxo-3-phenylpropanenitrile and N-phenylhydroxylamine. Also, part of the alkoxyamine had been converted to the NOH compound under the reaction conditions. Isolation was not attempted.

Example 34: (E)-N-(1,4-dimethoxy-1,4-dioxobutan-2-ylidene)-2-methyl-1-phenylpropan-1-amine oxide To a stirred solution of 10.12 g (30 mmol) of N-(2-methyl-1-phenylpropyl)hydroxylamine 4-methylbenzenesulfonate and 2.71 g of sodium acetate in 100 mL of methanol was added drop wise in 1 h at room temperature a solution of 4.26 g (30 mmol) of dimethyl acetylenedicarboxylate in 20 mL of methanol. After stirring for 1 h, the reaction mixture was poured into 250 mL of water and then extracted thrice with 100 mL-portions of dichloromethane. The collected organic fractions were washed with 50%-saturated aqueous bicarbonate and with brine, dried over sodium sulfate, and after filtration the solvents were removed by evaporation. Crude product was dissolved in hot petroleum ether and filtered. After cooling in a refrigerator the product was collected by filtration. Yield: 6.92 g (75%) of off-white crystals. $^1$H NMR δ 0.72 and 1.01 (each d, 3H, Me), 2.74 (m, 1H, CHMe$_2$), 3.61 (s, 3H, OMe), 3.65 (AA', 2H, CH$_2$), 3.82 (s, 3H, OMe), 6.54 (d, 1H, HC—N), 7.26-7.33 (m, 3H) and 7.52-7.58 (m, 2H) (Ph); $^{13}$C NMR δ 19.55 and 19.69 (CHMe$_2$), 31.84 (CHMe$_2$), 35.01 (CH$_2$), 52.18 and 52.91 (each OMe), 80.49 (HC—N), 128.48, 128.81 and 129.19 (each CH, Ph), 135.36 (C=N), 137.17 (q-C, Ph), 162.33 and 168.77 (each C=O).

Example 35 (Comparative): (E)-N-(1-methoxy-1-oxopropan-2-ylidene)-2-methyl-1-phenylpropan-1-amine oxide As in Example 34, but now adding 4.08 g (1.2 equiv) of methyl pyruvate and stirring overnight: after workup and stripping excess methyl pyruvate by co-evaporation with n-heptane the product was obtained in near quantitative yield as a yellow liquid. $^1$H NMR δ 0.71 and 0.95 (each d, 3H, Me), 2.17 (s, 3H, Me), 2.78 (m, 1H, CHMe$_2$), 3.82 (s, 3H, OMe), 6.31 (d, 1H, HC—N), 7.28-7.35 (m, 3H) and 7.56-7.61 (m, 2H) (Ph); $^{13}$C NMR δ 15.63 (MeC=N), 19.42 and 20.00 (CHMe$_2$), 31.53 (CHMe$_2$), 52.66 (OMe), 80.03 (HC—N), 128.42, 128.66 and 129.24 (each CH, Ph), 137.36 (q-C, Ph), 138.22 (C=N), 163.59 (C=O).

Example 36 (Comparative): (E)-N-(1,5-dimethoxy-1,5-dioxopentan-2-ylidene)-2-methyl-1-phenylpropan-1-amine oxide As in Example 34, but now adding 5.40 g (1.03 equiv) of dimethyl 2-oxoglutarate and stirring overnight: only 60% of the starting materials had reacted. Crystallization from n-heptane containing 1 equiv of acetic acid, cooling to room temperature and then in a refrigerator afforded after filtration and air drying 4.82 g (52%) of the desired nitrone. $^1$H NMR δ 0.69 and 0.94 (each d, 3H, Me), 2.52 (t, 2H) and 2.91 (m, 2H)(CH$_2$CH$_2$), 2.74 (m, 1H, CHMe$_2$), 3.56 and 3.82 (each s, 3H, OMe), 6.23 (d, 1H, HC—N), 7.22-7.32 (m, 3H) and 7.52-7.58 (m, 2H) (Ph); $^{13}$C NMR δ 19.44 and 19.80 (CHMe$_2$), 24.93 and 28.65 (each CH$_2$), 31.52 (CHMe$_2$), 51.76 and 52.77 (each OMe), 80.33 (HC—N), 128.44, 128.71 and 129.13 (each CH, Ph), 137.26 (q-C, Ph), 140.18 (C=N), 163.32 and 173.17 (each C=O).

Discussion of the Results of Examples 25-33

Surprisingly, nitrone regulators of Formula (10) with an activating group as $R^6$ are readily prepared from alkoxyamine regulators of Formula (8A) by a 1,3-elimination reaction using a catalytic (—CN as $R^6$) or a stoichiometric (ester or phosphonate as $R^6$) amount of a metal alkoxide base in polar aprotic medium such as DMF (Examples 25-30). Even with a conjugating group (Ph as $R^6$), this conversion can be successfully executed, provided that the N-substituent $R^1$ is a secondary alkyl and at least 2 equiv of metal alkoxide base are used (Example 31). By contrast, with a benzyl (Comparative Example 32) or a phenyl (Comparative Example 33) as the N-substituent $R^1$ this transformation failed.

Thus, it has thus been demonstrated that preparation of specific nitrone regulators of Formula (10) from alkoxyamine regulators of Formula (1A) (wherein $R^7$=H) may be done by treating an alkoxyamine of Formula (8A) with base to form the corresponding nitrone regulator of Formula (10).

Polymerization General

Commercial grade monomers were distilled under reduced pressure and then stored under a nitrogen atmosphere in a refrigerator until use. Solvents used in the solution polymerizations: toluene pa (Tol), anisole 99% (Ani), tert-butylbenzene 99% (tBB) and propyl acetate ≥99.5% (PrAc), were used as received.

Polymerization recipes are collected in Tables 1 and 2. Polymerization regulator R (a compound of Formula (8) or (10)), monomer M (vinyl monomer of Formula (2) and/or Formula (3)) and, optionally, solvent S were weighed into a narrow-mouth bottle containing a stirrer bar, and the flask was sealed with a septum. After the regulator compound had been completely dissolved, a nitrogen inlet needle reaching into the liquid and an outlet needle were attached. The contents were purged with nitrogen for 15 min, whilst stirring.

Polymerizations were carried out in 100-mL (bulk) or 250-mL (solution) three-necked round-bottom flasks, equipped with a stirrer bar, a septum with nitrogen inlet needle, an efficient (jacketed coil) reflux condenser with nitrogen outlet or calcium chloride drying tube, and an internal temperature reading device. Prior to charging a reactor, the flask was lowered into an oil bath pre-heated to the temperature at which to perform the polymerization, and the reactor was flushed with nitrogen for 15 min.

The solution of regulator in monomer (and optionally solvent) was then charged into the preheated flask and the contents were stirred under a slow stream of nitrogen. The temperature was allowed to rise rapidly to the desired internal reaction temperature and maintained there for the duration of the experiment. For methacrylic monomers reaction temperatures reported in Table 2 were those at reflux: the experimental setup apparently caused a small pressure drop in the reactor, which caused these monomers (and optionally solvent) to reflux at a temperature slightly below their reported boiling point at normal pressure.

Conversions (c) were determined gravimetrically by drawing aliquots of ca. 2-3 mL by means of a disposable syringe at regular intervals of 0:15 h after time 0 h, the latter being arbitrarily chosen as the time when the internal temperature of the polymerization mixture was ca. 10 degrees below the intended reaction temperature. In general, monitoring was continued until viscosity build-up in the polymerization mixture prevented representative sampling. All samples were dried until constant weight in a ventilated oven maintained at 60° C.

When polymerization is in control, conversion, expressed as $<\ln 1/(1-c)>$, increases linearly with time and $M_n$, the number average molecular weight, does so with conversion (cf. FIGS. 1 and 2 for pertinent examples). From the linear regime in a plot of $<\ln 1/(1-c)>$ versus time, a first-order rate constant of polymerization, $k_{app}$ ($h^{-1}$), was obtained (cf. Tables 1-2). This constant allows for an immediate assessment of the batch time required to achieve high conversion: i.e., a value for $<\ln 1/(1-c)>$ of 3.0 to 3.5 corresponds to a conversion in excess of 95 to 97%, respectively.

From conversion a theoretical number average molecular weight for linear polymer, $M_{n,calc\ lin}$, was calculated, assuming 100% efficiency of the regulator compound. As will be discussed, for styrene polymerizations and for methacrylics copolymerizations with styrene, a ratio of observed $M_n$ to $M_{n,calc\ lin}$ (significantly) below unity may be construed as evidence for the cyclic nature of polymer produced and thus for the method of its production as a novel process that in this patent is called Pseudo-Ring Expansion Polymerization (P-REP).

By contrast, for a well-controlled Nitroxide-Mediated Polymerization (NMP) process to produce linear polymer, as described in a comparative example below, the ratio of $M_n$ to $M_{n,calc\ lin}$ is (slightly) in excess of unity: initiator efficiency is below 100%, as a small part of regulator compound is consumed at the start of the process to establish the Persistent Radical Effect (PRE)—a low surplus of nitroxide that suppresses termination in favor of propagation.

For polymer characterization by size exclusion chromatography (SEC) samples were prepared by dissolving ca. 2.4 mg of dried polymer per mL of THF containing ca. 0.3 w % toluene and filtering the polymer solutions so obtained into vials using Acrodisc® syringe filters (nylon membrane; pore size 0.2 μm). The setup for SEC consisted of a pump, a differential refractometer (Waters 2410), and three columns in series (Styragel HR2, HR4 and HR6, with pore sizes ranging from $10^2$ to $10^6$ Å). SEC analyses were performed at 35° C. using THF as solvent at a flow rate of 1 mL/min. For calibration a set of linear polystyrene (PS) standards of low polydispersity index (PDI) was used. Universal calibration was applied, employing following MHS constants: α 0.704 and K 15.8×$10^{-5}$ dL·$g^{-1}$ (PS) and α 0.69 and K 12.2×$10^{-5}$ dL·$g^{-1}$ (pMMA) (cf. Mori, S. and Barth, H. G. *Size Exclusion Chromatography*, Springer, 1999, p. 201); and α 0.714 and K 9.7×$10^{-5}$ dL·$g^{-1}$ (pEMA at 30° C.; cf. Hutchinson, R. A. et al. *Macromolecules* 1997, 30, 3490-3).

The robustness of the polymerization procedure and the subsequent analysis by SEC was verified by running a bulk linear polymerization of styrene at 112° C., employing as regulator 2-((tert-butyl(1-(diethoxyphosphoryl)-2,2-dimethylpropyl)amino)oxy)-2-methylpropanoic acid (a.k.a. BlockBuilder® MA, abbreviated BB). These results are included below as Example 37 (Comparative).

Controlled Pseudo-Ring Expansion Polymerization (P-REP) of Styrene

Table 1 (Examples 38-50) discloses the recipes and results for a new Pseudo-Ring Expansion Polymerization (P-REP) process of 1-substituted vinyl monomer styrene (2; $R^8$=Ph), controlled by an alkoxyamine of Formula (8A) or a nitrone of Formula (1C) as regulator, to produce cyclic polystyrene (cPS). Two alkoxyamines known previously (included as Comparative Examples 23 and 24 above) fail to produce well-defined cPS (exclusively) and are thus comparative (Examples 51 and 52).

The outcome of these Examples is distinctly different from that of the Comparative Example 37 that describes the known use of alkoxyamine 2-((tert-butyl(1-(diethoxyphosphoryl)-2,2-dimethylpropyl)amino)oxy)-2-methylpropanoic acid (abbreviated BB) as regulator for a Nitroxide-Mediated Polymerization (NMP) to give linear PS. Example 37 further establishes that the general polymerization and SEC analysis procedures employed herein are robust.

Example 37 (Comparative): Styrene Bulk NMP at 112° C. Using BB as Regulator

Conversion, expressed as <ln 1/(1−c)>, increased linearly with time, while number average molecular weight ($M_n$) increased linearly with conversion and polydispersity index (PDI) rapidly decreased to a limiting value of 1.10 (FIG. 1). Thus, styrene polymerization in bulk mediated by alkoxyamine regulator BB was in control. The outcome of Example 37 is in line with literature precedents (see, e.g.: Nicolas, J. et al. *Macromol.* 2004, 37, 4453-63).

Throughout polymerization $M_n$ was ca. 4-5% higher than $M_{n,\ calc\ lin}$, caused by some termination at the start of polymerization to establish the Persistent Radical Effect (PRE)—a low surplus of nitroxide that suppresses termination in favor of propagation in a Nitroxide-Mediated Polymerization (NMP) process. Again, this finding is in line with literature precedents.

Rheology measurements on samples having $M_n$ 11300 D and 27400 D revealed that in each case the loss modulus (G') in the rubbery state was proportional to frequency to the power 2, as was to be expected for linear PS chains.

Example 38: Styrene Bulk P-REP at 122° C. Using Alkoxyamine of Example 14 as Regulator Conversion, expressed as <ln 1/(1−c)>, increased linearly with time, while $M_n$ increased linearly with conversion and PDI decreased to a limiting value of 1.15 (FIG. 1). Thus, the styrene polymerization in bulk mediated by alkoxyamine regulator of Example 14 (disclosed herein) was in control.

In contrast to the outcome of Comparative Example 37, throughout this polymerization the ratio of apparent $M_n$ to $M_{n,\ calc\ lin}$ was significantly below unity. Thus, polystyrene so produced was not a linear polymer.

Rheology measurements on samples having apparent $M_n$ 6000 D and 20200 D revealed that for each the loss modulus (G') in the rubbery state was proportional to frequency to the power 1.5. This distinguishes the polystyrene so produced from that in Comparative Example 37 as being mostly, if not exclusively, cyclic (cPS) (cf. Santangelo, P. G. et al. *Macromolecules* 2001, 34, 9002-5). Example 38 then represents the first successful case of a novel controlled synthesis of this cyclic vinyl polymer, which in this patent is called Pseudo-Ring Expansion Polymerization.

Note: the hydrodynamic volume of cyclic PS is smaller by a factor 0.71 than its linear counterpart of the same chain length (cf. Roovers, J. In *Cyclic Polymers*; Semlyen, J. A (Ed.); Kluwer, 2. Ed., 2000; pp. 347-84). When the ratio of apparent $M_n$ to $M_{n,\ calc\ lin}$ is divided by PDI, a ratio of ca. 0.71 is obtained for most of the samples in Example 38. This further confirms the nature of most, if not all, polymer present as being cyclic. (This correction is warranted as the above definition of $M_{n,\ calc\ lin}$ implies a PDI of 1.00)

Example 39: Styrene Bulk P-REP at 120° C. Using Nitrone of Example 28 as Regulator Conversion, expressed as <ln 1/(1−c)>, increased linearly with time, indicating that styrene polymerization in bulk mediated by nitrone regulator of Example 28 (disclosed herein) was in control. When corrected for a lower temperature in Example 39, a similar first-order rate constant of polymerization, $k_{app}$ (h$^{-1}$), was found as in Example 38.

Example 40: Styrene Bulk P-REP at 120° C. Using Nitrone of Example 29 as Regulator Conversion, expressed as <ln 1/(1−c)>, increased linearly with time, indicating that styrene polymerization in bulk mediated by nitrone regulator of Example 29 (disclosed herein) was in control. Under otherwise identical conditions, a similar first-order rate constant of polymerization, $k_{app}$ (h$^{-1}$), was found as in Example 39.

Example 41: Styrene Solution P-REP at 126° C. Using Alkoxyamine of Example 14 as Regulator Conversion, expressed as <ln 1/(1−c)>, increased linearly with time up to a value of 1.2 (or ca. 70% conversion); thereafter, it showed acceleration. Still, $M_n$ increased linearly with conversion (up to at least 92.5% conversion) and PDI decreased to a final value of 1.09 (FIG. 1). Thus, styrene polymerization in solution mediated by the alkoxyamine regulator of Example 14 (disclosed herein) was in control.

As in Example 38, throughout polymerization the ratio of apparent $M_n$ to $M_{n,\ calc\ lin}$ was well below unity. Thus, PS so produced was cyclic and the process for its production was an example of the Pseudo-Ring Expansion Polymerization (P-REP) process disclosed herein.

Example 42: Styrene Bulk P-REP at 120° C. Using Alkoxyamine of Example 11 as Regulator Conversion, expressed as <ln 1/(1−c)>, increased linearly with time, indicating that styrene polymerization in bulk mediated by the alkoxyamine regulator of Example 11 (disclosed herein) was in control.

The apparent $M_n$ at 52.49% conversion was 16350 D (PDI 1.70), while 18505 D was calculated ($M_{n,\ calc\ lin}$). As the ratio $M_n/M_{n,\ calc}$ was well below unity, PS so produced was cyclic and the process for its production was an example of the Pseudo-Ring Expansion Polymerization (P-REP) process disclosed herein.

Example 43: Styrene Bulk P-REP at 120° C. Using Alkoxyamine of Example 17 as Regulator Conversion, expressed as <ln 1/(1−c)>, increased linearly with time, indicating that styrene polymerization in bulk mediated by the alkoxyamine regulator of Example 17 (disclosed herein) was in control. Within experimental error and under otherwise identical conditions, a similar first-order rate constant of polymerization, $k_{app}$ (h$^{-1}$), was found as in Example 42.

The apparent $M_n$ at 52.63% conversion was 15795 D (PDI 2.30), while 18514 D was calculated ($M_{n,\ calc\ lin}$). As the ratio $M_n/M_{n,\ calc}$ was well below unity, PS so produced was cyclic and the process for its production was an example of the Pseudo-Ring Expansion Polymerization (P-REP) process disclosed herein.

Example 44: Styrene Bulk P-REP at 112° C. Using Nitrone of Example 25 as Regulator Conversion, expressed as <ln 1/(1−c)>, increased linearly with time, indicating that styrene polymerization in bulk mediated by nitrone regulator of Example 25 (disclosed herein) was in control. When corrected for the lower temperature in Example 44, a similar first-order rate constant of polymerization, $k_{app}$ (h$^{-1}$), was found as in Example 43.

Example 45: Styrene Solution P-REP at 112° C. Using Nitrone of Example 26 as Regulator Conversion, expressed as <ln 1/(1−c)>, increased linearly with time, indicating that styrene polymerization in solution

Example 46: Styrene Bulk P-REP at 120° C. Using Alkoxyamine of Example 12 as Regulator Conversion, expressed as <ln 1/(1−c)>, increased linearly with time, indicating that styrene polymerization in bulk mediated by the alkoxyamine regulator of Example 12 (disclosed herein) was in control.

The apparent $M_n$ at 53.91% conversion was 17455 D (PDI 1.68), while 18955 D was calculated ($M_{n,\ calc\ lin}$). As the ratio $M_n/M_{n,\ calc}$ was below unity, PS so produced was cyclic and the process for its production was an example of the Pseudo-Ring Expansion Polymerization (P-REP) process disclosed herein.

Example 47: Styrene Bulk P-REP at 120° C. Using Alkoxyamine of Example 13 as Regulator Conversion, expressed as <ln 1/(1−c)>, increased linearly with time, indicating that styrene polymerization in bulk mediated by the alkoxyamine regulator of Example 13 (disclosed herein) was in control.

The apparent $M_n$ at 52.82% conversion was 13192 D (PDI 1.43), while 18541 D was calculated ($M_n$, $M_{n,\ calc\ lin}$). As the ratio $M_n/M_{n,\ calc}$ was well below unity, PS so produced was cyclic and the process for its production was an example of the Pseudo-Ring Expansion Polymerization (P-REP) process disclosed herein.

Example 48: Styrene Bulk P-REP at 120° C. Using Nitrone of Example 27 as Regulator Conversion, expressed as <ln 1/(1−c)>, increased linearly with time, indicating that styrene polymerization in bulk mediated by nitrone regulator of Example 27 (disclosed herein) was in control. Correcting for the higher concentration in Example 48, a similar first-order rate constant of polymerization, $k_{app}$ (h$^{-1}$), was found as in Example 47.

Example 49: Styrene Bulk P-REP at 112° C. Using Alkoxyamine of Example 21 as Regulator Conversion, expressed as <ln 1/(1−c)>, increased linearly with time, indicating that styrene polymerization in bulk mediated by the alkoxyamine regulator of Example 21 (disclosed herein) was in control.

The apparent $M_n$ at 70.59% conversion was 16849 D (PDI 1.78), while 24662 D was calculated ($M_{n,\ calc\ lin}$). As the ratio $M_n/M_{n,\ calc}$ was well below unity, PS so produced was cyclic and the process for its production was an example of the Pseudo-Ring Expansion Polymerization (P-REP) process disclosed herein.

Example 50: Styrene Solution P-REP at 122° C. Using Alkoxyamine of Example 21 as Regulator Conversion, expressed as <ln 1/(1−c)>, increased linearly with time up to a value of 1.2 (or ca. 70% conversion); thereafter, it showed acceleration. Still, $M_n$ increased linearly with conversion over the full range up to at least 97.10% conversion and PDI decreased to a final value of 1.33 (FIG. 1). Thus, styrene polymerization in solution mediated by alkoxyamine regulator of Example 21 (disclosed herein) was in control.

Throughout most of the polymerization the ratio of apparent $M_n$ to $M_{n,\ calc\ lin}$ was lower than unity. Thus, PS so produced was cyclic and the process for its production was an example of the Pseudo-Ring Expansion Polymerization (P-REP) process disclosed herein.

Example 51 (Comparative): Styrene Bulk Polymerization at 120° C. Using Alkoxyamine of Example 23 as Regulator Conversion, expressed as <ln 1/(1−c)>, increased linearly with time. However, $M_n$ was more or less constant at 17-20 kD up to ca. 35% conversion, i.e., far above $M_{n,\ calc\ lin}$ (PDI around 1.3). $M_n$ did increase beyond ca. 35% conversion, but with concomitant broadening of the distribution. Thus, PS so produced was not cyclic and the process for its production was not an example of the Pseudo-Ring Expansion Polymerization (P-REP) process disclosed herein.

Example 52 (Comparative): Styrene Bulk Polymerization at 120° C. Using Alkoxyamine of Example 24 as Regulator Conversion, expressed as <ln 1/(1−c)>, increased linearly with time. However, $M_n$ at 52.82% conversion was 31800 D (PDI 3.09), while 18402 D was calculated ($M_{n,\ calc\ lin}$). As the ratio $M_n/M_{n,\ calc}$ was far above unity, PS produced was not (exclusively) cyclic, thus the process for its production was not an example of the Pseudo-Ring Expansion Polymerization (P-REP) process disclosed herein.

Discussion of the Results of Examples 37-52 (Table 1 and FIG. 1)

The outcome of Comparative Example 37, a Nitroxide-Mediated Polymerization (NMP) using 2-((tert-butyl(1-(diethoxyphosphoryl)-2,2-dimethylpropyl)amino)oxy)-2-methylpropanoic acid (abbreviated BB) as regulator to give linear PS, is in accordance with literature precedents. The outcome thus establishes that the polymerization procedure and subsequent analysis by SEC are robust. Therefore, the unexpected results of Experiments 38-50 when using alkoxyamine regulators of Formula (8A) and nitrone regulators of Formula (1C) are no artefact.

Alkoxyamine regulator of Example 14 (disclosed herein) is structurally related to BB. The differences are replacement of the diethoxyphosphoryl in BB by the somewhat smaller methoxycarbonyl and, in particular, introduction of a cyano in the aliphatic part (Formula (8A): $Z^1$=—CN). The difference in substituent at oxygen is of no consequence, as it is known from literature that both types facilitate rapid dissociation and initiation in radical polymerization.

As in Comparative Example 37, when using alkoxyamine regulator of Example 14 in styrene bulk polymerization (Example 38), conversion (expressed as <ln 1/(1−c)>) increases linearly with time, as does $M_n$ with conversion, while PDI decreases to a slightly higher final value of 1.15. Surprisingly and unexpectedly, in Example 38 the ratio of apparent $M_n$ to $M_{n,\ calc\ lin}$ is significantly below unity throughout polymerization, this in marked contrast to the outcome of Comparative Example 37 (ratio above 1).

Thus, polystyrene produced according to Example 38 cannot be linear. Rheology measurements have established that polymer present throughout the polymerization and, thus, the final polymer so produced is mostly, if not exclusively, cyclic polystyrene (cPS) of low PDI. Its manufacture is then the first example of a well-controlled Pseudo-Ring Expansion Polymerization (P-REP) process of this vinyl monomer, for which there is no precedent.

The discrepancy between apparent $M_n$ and $M_{n,\ calc\ lin}$ is then readily explained. Due to the smaller hydrodynamic volume of cyclic polymer (cf. Roovers, J. In *Cyclic Polymers*; Semlyen, J. A (Ed.); Kluwer, 2. Ed., 2000; pp. 347-84), cyclic PS will elute later than its linear counterpart of the same degree of polymerization. As universal calibration in SEC is based on linear PS standards, $M_n$ for cPS is assigned only 70-75% of the true value.

Other alkoxyamines of Formula (8A) when used to polymerize styrene in bulk behave similarly and, thus, they illustrate their universality and versatility for producing cyclic polystyrene in a controlled Pseudo-Ring Expansion Polymerization (P-REP) process.

Three further examples of alkoxyamines of Formula (8A) with a tertiary alkyl (t-Bu) as N-substituent $R^1$, but now with —CN as $R^6$, display linearity in their plots of conversion (expressed as $<\ln 1/(1-c)>$) versus time and ratios of apparent $M_n$ to $M_{n,\ calc\ lin}$ well below unity. Thus, polymer so produced is cyclic and its production is by a controlled Pseudo-Ring Expansion Polymerization (P-REP) process. As in Example 38, Examples 42 and 46 employ alkoxyamines with —CN as $Z^1$ in Formula (8A). Example 47 teaches that the process can equally well be executed with an alkoxyamine of Formula (8A) having an ester group ($CO_2Me$) as $Z^1$.

Two further examples on bulk polymerization of styrene demonstrate that the scope of the invention also encompasses alkoxyamines of Formula (8A) with a secondary alkyl (c-Hex) as N-substituent $R^1$: Example 43 employing an alkoxyamine of Formula (8A) with —CN and Example 49 with a phenyl as $R^6$.

By contrast, with a benzyl (Comparative Example 51) or a phenyl (Comparative Example 52) as the N-substituent in the alkoxyamine no (well-defined) cyclic polymer is produced.

The cyclic nature of polymer present throughout the polymerization demands that cyclic initiating alkoxyamine species are rapidly and quantitatively formed in situ from the alkoxyamines of Formula (8A) supposedly via the corresponding nitrones of Formula (1C) at the start of the process. Upon their in situ formation nitrones of Formula (1C) initiate oligomerization of styrene at the nitrone carbon: di-radical species so-formed have one nitroxide- and one styrene radical terminus each and predominantly display intramolecular combination to yield in situ cyclic mono-alkoxyamine oligomer species of Formula (1A), wherein $R^7$ and $R^4$ are each a (primary) $CH_2$ linked into a ring by a $CHPh(CH_2CHPh)_m$ chain.

To some extent, intermolecular combination by head-to-tail coupling of 2 (3, etc.) di-radical species will occur to give monocyclic di(tri, etc.)alkoxyamine oligomers. Thus, rather than as a sign of less than optimal control, the extent to which these species are formed, explains why in some examples disclosed herein, PDI was above 1.5.

Corroboration of this notion is found when comparing results on S P-REP in bulk and solution (Examples 38 and 41; 49 and 50): a lower PDI is obtained in solution, as the in situ transformation of alkoxyamine regulator of Formula (8A) via the nitrone regulator of Formula (1C) to cyclic initiating alkoxyamine species now occurs at lower concentration, thus favoring even further intramolecular combination to give cyclic mono-alkoxyamine over intermolecular combination to yield cyclic di(tri, etc.)alkoxyamine oligomer species.

Nitrones of Formula (1C) are then supposedly formed in situ as intermediate in the transformation of alkoxyamines of Formula (8A) into cyclic alkoxyamine oligomers of Formula (1A) that then initiate and control Pseudo-Ring Expansion Polymerization (P-REP). In support of this notion, nitrones of Formula (1C) are indeed able to initiate and control styrene polymerization, as evidenced by linearity in their plots of conversion (expressed as $<\ln 1/(1-c)>$) versus time (Table 1: Examples 39, 40, 44, 45 and 48).

Further to that, when corrected for differences in concentration and/or temperature, each nitrone of Formula (1C) shows a similar first-order rate constant of polymerization, $k_{app}$ ($h^{-1}$), as its alkoxyamine counterpart of Formula (8) does in styrene P-REP (cf. following pairs of Examples: 39 and 38, 45 and 42, 44 and 43, 48 and 47, in Table 1).

That alkoxyamines of Formula (8A)—by their in situ transformation via nitrones of Formula (1C) to cyclic alkoxyamine oligomers of Formula (1A)—are able to initiate and control a Ring Expansion Polymerization (REP) process with the level of control over $M_n$ and PDI disclosed herein and thus provide access to polymer that is mostly, if not exclusively, cyclic in nature, is unprecedented. In fact, it is completely unexpected on the basis of all reported examples of prior art that describe the use of pre-formed cyclic alkoxyamines for controlling REP (cf.: Ruehl, J. et al. *J. Polym. Sc., Part A: Polym. Chem.* 2008, 46, 8049-69; Narumi, A. et al. Ibid. 2010, 48, 3402-16; Nicolaÿ, R. et al. *Macromol.* 2011, 44, 240-7).

Two intrinsic features of free-radical Nitroxide-Mediated Polymerization (NMP) for producing well-defined linear polymer are establishing the Persistent Radical Effect (PRE—a low surplus of nitroxide that suppresses termination in favor of propagation) at the start of the polymerization and exchange reactions of nitroxides between chains throughout. The low surplus of nitroxide is either added as such or generated in situ by some termination in establishing the PRE.

These same features produce a complete failure when designing a free-radical NMP-type of Ring Expansion Polymerization (REP) process for producing well-defined cyclic polymer with any cyclic alkoxyamine system. Termination by combination at the start to establish the PRE leads to a small fraction of linear di-nitroxides. Exchange reactions of nitroxides then leads to oligomerization of rings and—with the small fraction of linear di-nitroxide initially formed—to a significant weight fraction linear polymer of very high molecular weight. The outcome is an ill-defined blend of cyclic and linear polymer with $M_n$ far in excess of that calculated from conversion and high PDI: loss of architectural integrity predominates even at low conversion (cf. FIG. 5 and Table 2 in Nicolaÿ, R. et al. *Macromol.* 2011, 44, 240-7). Hence, it must be concluded that cyclic vinyl polymer cannot be produced by a controlled free-radical NMP-type of REP process.

By contrast, in examples on styrene P-REP disclosed herein control over architectural integrity is maintained throughout: $M_n$ remains consistently below that calculated from conversion for a linear chain and there is no sign of broadening even for conversions in excess of 90% (cf. Examples 41 and 50). Consequently, exchange reactions can play no part at all, thus, the mechanism of propagation in the P-REP process for producing cyclic vinyl polymer disclosed herein cannot be of the free-radical NMP-type, but must involve some kind of insertion mechanism.

A distinctive feature in cyclic alkoxyamine oligomers formed in situ from alkoxyamines of Formula (8) and nitrones of Formula (1C) disclosed herein, is the presence of the $Z^1$ substituent. Absent in all cyclic alkoxyamines of prior art, this group apparently plays a vital part in establishing control in the process disclosed herein.

This notion is corroborated by results on n-butyl acrylate (2, BA: $R^8$=C(O)OBu) P-REP in solution (toluene as solvent, 65% R+M, 0.004 R/M, 112° C.) using nitrones prepared according to Examples 34-36. Whereas nitrone of Example 34 (a regulator of Formula (1C) with $R^1$=sec-alkyl, $R^2$=$R^3$=H, $R^6$=$Z^1$=C(O)OMe) is able to control BA solution polymerization ($k_{app}$ 0.385 $h^{-1}$), the nitrones of Comparative Examples 35 (lacking the ester group) and 36 (having the ester group one carbon further along the chain) are clearly not, as they show limiting conversions of 2.0% and 1.7%, respectively. (Note: BA was used, this in order to exclude any distorting contribution to conversion from S auto-initiation)

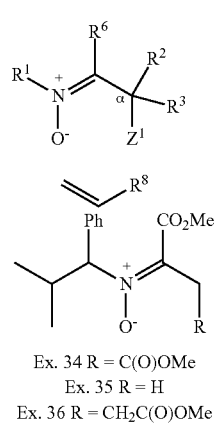

Ex. 34 R = C(O)OMe
Ex. 35 R = H
Ex. 36 R = CH₂C(O)OMe

Until now, potential advantages of cyclic vinyl polymer over its linear counterpart in various end-use applications have not been exploited, because of a prohibitive cost of production. The only method available to date is by α, ω-end coupling in a pre-formed linear polymer under conditions that favor intramolecular reaction in order to minimize the extent of linear contamination (for a review cf. Jia, Z. et al. *J. Polym. Sci., Part A: Polym. Chem.* 2012, 50, 2085-97).

While progress has been made in recent years, all methodology known to date still suffers from at least one, but frequently all of following shortcomings:
the process is a multi-step, complex and time-consuming procedure: synthesis of linear polymer, chain end transformation and ring closure by α, ω-end coupling;
in the ring-closing step prolonged reaction time is frequently and (ultra)high dilution is always required; e.g., solids contents typically are ca. 1% at best (and in many cases much lower) for polymers with degrees of polymerization of only ca. 20-30 (the higher molecular weights needed in most industrial applications requiring even further dilution);
purification is required after several of the steps involved, a.o., to remove large excess of reagents used in both the chain end transformation and in the α, ω-end coupling, as well as the huge quantities of solvent used in the latter step; this is evidently undesirable from both cost perspective, as well as from operational and environmental points of view.

By contrast, the process disclosed herein overcomes all of these present limitations. E.g., in Example 41 disclosed herein polymer that is mostly, if not exclusively, cyclic polystyrene with a degree of polymerization in excess of 300 and low PDI is made in a single step in a high-conversion and high-solids solution ring expansion polymerization process with a batch time of 4 h, requiring only the customary volatiles removal as a final purification.

Thus, cyclic vinyl polymer can now be made in a manner fully compatible with industrial practice. As the regulators of Formulas (8A) and (1C) disclosed herein are accessible from cheap and readily available raw materials, their application at industrial scale will now enable the production of cyclic vinyl polymer in a cost-effective way, so that the full potential of cyclic vinyl polymer in end-use applications can be fully exploited.

To this end, the higher PDI found for some of the REP processes in bulk must not be seen in any way as a limitation of the invention: if the aim is to prepare a cyclic vinyl polymer with no concern for PDI, then bulk vinyl REP using as regulator any of the alkoxyamines of Formula (8A) or nitrones of Formula (1C) disclosed herein (including combinations thereof), is a viable method. In industrial practice this may be more readily accomplished in a mini-bulk system by dispersion- or (mini)emulsion polymerization process.

If, on the other hand, the objective is to prepare cyclic vinyl polymer of low PDI, then a person skilled in the art will be able to achieve this by properly adjusting experimental parameters, such as concentration and temperature, as already demonstrated herein (compare Examples 38 and 41; Examples 49 and 50).

Alternatively and particularly suited when using nitrone regulators of Formula (1C), he can execute the process in two stages: in the first stage a solution of an alkoxyamine of Formula (8A) or a nitrone of Formula (1C) is briefly contacted with a small part of the monomer under such conditions that the in situ formation of cyclic monoalkoxyamine oligomer occurs (almost) exclusively. To cyclic pre-polymer so obtained is then added further monomer in a second stage, wherein he can grow the cyclic pre-polymer to the targeted molecular weight with proper control over PDI. Or, optionally, he can dispense with the use of solvent when the resultant solution of cyclic pre-polymer in monomer is used to execute REP in a mini-bulk system, such as by a dispersion- or (mini)emulsion polymerization process.

Controlled Linear Homopolymerization and Pseudo-Ring Expansion Copolymerization of Methacrylics Table 2 (Examples 55-59) shows recipes and results for a homopolymerization process of 1,1-disubstituted vinyl monomers (3) methyl methacrylate ($R^9$=C(O)OMe; $R^{10}$=Me; MMA) and ethyl methacrylate ($R^9$=C(O)OEt; $R^{10}$=Me; EMA) using alkoxyamines of Formula (8A) to form a linear homopolymer. Some alkoxyamines of Formula (8A) (cf. Examples 53 and 54) are not in control and are thus comparative.

Inclusion of a small weight fraction of styrene in a methacrylics polymerization recipe, a strategy known to overcome the lack of control displayed by most alkoxyamines of prior art in producing linear homopolymer, is also successful when employing alkoxyamines of Formula (8A), but in contrast to the prior art it produces cyclic polymer with all alkoxyamines of Formula (8A) (Examples 60-65). Thus, these examples represent further illustrations of the controlled Pseudo-Ring Expansion Polymerization (P-REP) process disclosed herein.

Example 53 (Comparative): MMA Solution Homopolymerization at 97° C. Using Alkoxyamine of Example 14

Conversion, expressed as <ln 1/(1−c)>, did not increase linearly with time, but rapidly rose to a limiting value of ca. 31% (FIG. 2). This indicated that homopolymerization of MMA in solution was initiated but not controlled by alkoxyamine of Example 14.

Example 54 (Comparative): MMA Solution Homopolymerization at 97° C. Using Alkoxyamine of Example 13

Conversion, expressed as <ln 1/(1−c)>, did not increase linearly with time, but rapidly rose to a limiting value of ca. 39%. This indicated that homopolymerization of MMA was initiated but not controlled by alkoxyamine of Example 13.

Example 55: MMA Solution Homopolymerization at 97° C. Using Alkoxyamine of Example 11 as Regulator Conversion, expressed as <ln 1/(1−c)>, increased linearly with time and $M_n$ increased linearly with conversion (FIG. 2), indicating that the homopolymerization of MMA in solution mediated by alkoxyamine regulator of Example 11 (disclosed herein) was in control. While initially around 1.3, evolution of PDI to a limiting value of 1.5 occurred beyond ca. 40% conversion. As the ratio $M_n/M_{n,\ calc}$ was above unity throughout the polymerization, the PMMA so produced was linear.

Example 56: MMA Solution Homopolymerization at 97° C. Using Alkoxyamine of Example 12 as Regulator Conversion, expressed as <ln 1/(1−c)>, increased linearly with time and $M_n$ increased linearly with conversion up to at least 97.09% conversion (FIG. 2), indicating that homopolymerization of MMA in solution mediated by alkoxyamine regulator of Example 12 (disclosed herein) was in control. While initially around 1.2, evolution of PDI to a limiting value of 1.5 occurred beyond ca. 70% conversion. As the ratio $M_n/M_{n,\ calc}$ was above unity throughout polymerization, the PMMA so produced was linear.

Example 57: MMA Solution Homopolymerization at 97° C. Using Alkoxyamine of Example 17 as Regulator Conversion, expressed as <ln 1/(1−c)>, increased linearly with time, indicating that homopolymerization of MMA in solution mediated by the alkoxyamine regulator of Example 17 (disclosed herein) was in control. Taking the difference in concentration into account, solution polymerization of MMA mediated by alkoxyamine regulator of Example 17, as disclosed in this Example, was significantly slower than that mediated by alkoxyamine of Example 11, as disclosed in Example 55, which reflects a decrease in steric hindrance in the alkoxyamine of Example 17.

Example 58: EMA Bulk Homopolymerization at 10° C. Using Alkoxyamine of Example 17 as Regulator Conversion, expressed as <ln 1/(1−c)>, increased linearly with time, indicating that homopolymerization of EMA in bulk mediated by alkoxyamine regulator of Example 17 (disclosed herein) was in control.

Example 59: MMA Solution Homopolymerization at 98-9° C. Using Alkoxyamine of Example 21 as Regulator Conversion, expressed as <ln 1/(1−c)>, increased linearly with time and $M_n$ increased linearly with conversion (FIG. 2), indicating that the homopolymerization of MMA in solution mediated by the alkoxyamine regulator of Example 21 (disclosed herein) was in control. While initially decreasing to 1.35, evolution of PDI to a limiting value of 1.5 occurred beyond 65% conversion. As the ratio $M_n/M_{n,\ calc}$ was above unity throughout the polymerization, the PMMA so produced was linear.

Example 60: MMA-S (4.4 w %) Bulk P-REP at 96° C. Using Alkoxyamine of Example 14 as Regulator Conversion, expressed as <ln 1/(1−c)>, increased linearly with time and $M_n$ increased linearly with conversion, indicating that bulk polymerization of MMA containing 4.4 w % styrene and mediated by the alkoxyamine regulator of Example 14 (disclosed herein) was in control.

Throughout polymerization the ratio of apparent $M_n$ to $M_{n,\ calc\ lin}$ was below unity. Thus, the copolymer so produced was predominantly cyclic and the method for its production was an example of the Pseudo-Ring Expansion Polymerization (P-REP) process disclosed herein.

Example 61: EMA-S (4.5 w %) Solution P-REP at 108° C. Using Alkoxyamine of Example 14 as Regulator Conversion, expressed as <ln 1/(1−c)>, increased linearly with time, while $M_n$ increased linearly with conversion (FIG. 2), indicating that solution polymerization of EMA containing 4.5 w % styrene and mediated by alkoxyamine regulator of Example 14 (disclosed herein) was in control.

Throughout polymerization the ratio of apparent $M_n$ to $M_{n,\ calc\ lin}$ was well below unity. Thus, the copolymer so produced was predominantly cyclic and the method for its production was an example of the Pseudo-Ring Expansion Polymerization (P-REP) process disclosed herein.

Example 62: MMA-S (4.4 w %) Solution P-REP at 98-9° C. Using Alkoxyamine of Example 21 as Regulator Conversion, expressed as <ln 1/(1−c)>, increased linearly with time and displayed 2 rate regimes (FIG. 2): up to ca. 65% conversion of an MMA-S copolymerization and beyond of MMA homopolymerization. $M_n$ increased linearly with conversion up to at least 90% (FIG. 2), indicating that solution polymerization mediated by alkoxyamine regulator of Example 21 (disclosed herein) was in control.

Throughout polymerization the ratio of apparent $M_n$ to $M_{n,\ calc\ lin}$ was lower than unity. Thus, polymer so produced was predominantly cyclic and the method for its production was an example of the Pseudo-Ring Expansion Polymerization (P-REP) process disclosed herein.

Compared to Examples 60 and 61, as well as to examples on styrene P-REP disclosed above, $M_n/M_{n,\ calc\ lin}$ was significantly lower, thus apparent $M_n$ was even further reduced. As the P-REP process of the invention involves some kind of insertion mechanism, some level of tacticity enrichment in cyclic PMMA (co)polymer so produced may well have occurred: this would then account for a further reduction in hydrodynamic volume and, thus, apparent $M_n$.

Example 63: MMA-S (1.1 w %) Solution P-REP at 98-9° C. Using Alkoxyamine of Example 21 as Regulator Conversion, expressed as <ln 1/(1−c)>, increased linearly with time and displayed 2 rate regimes: up to ca. 50% conversion of an MMA-S copolymerization and beyond of MMA homopolymerization. $M_n$ increased linearly with conversion up to at least 90%, indicating that this solution polymerization mediated by the alkoxyamine regulator of Example 21 (disclosed herein) was in control.

Throughout polymerization the ratio of apparent $M_n$ to $M_{n,\ calc\ lin}$ was lower than unity. Thus, polymer so produced was predominantly cyclic and the method for its production was an example of the Pseudo-Ring Expansion Polymerization (P-REP) process disclosed herein.

Compared to Examples 60 and 61, as well as to examples on styrene P-REP disclosed above, but as in Example 62, $M_n/M_{n,\ calc\ lin}$ was significantly lower, thus apparent $M_n$ was even further reduced. As the P-REP process of the invention involves some kind of insertion mechanism, some level of tacticity enrichment in cyclic PMMA (co)polymer so produced may well have occurred: this would then account for a further reduction in hydrodynamic volume and, thus, apparent $M_n$.

Example 64: MMA-S (4.0 w %) Solution P-REP at 98-9° C. Using Alkoxyamine of Example 11 as Regulator Conversion, expressed as <ln 1/(1−c)>, increased linearly with time and displayed 2 rate regimes: up to ca. 35% conversion of an MMA-S copolymerization and beyond of MMA homopolymerization. Remarkably, while $M_n$ increased linearly with conversion, it did so in 2 distinct regimes (see below). Nonetheless, this combination of results still indicated that solution polymerization of MMA containing 4.0 w % of styrene mediated by the alkoxyamine regulator of Example 11 (disclosed herein) was in control.

Remarkably, $M_n$ increased linearly with conversion in 2 distinct regimes: one up to ca. 25% conversion and one beyond 25%, in each case displaying ratios of apparent $M_n$ to $M_{n,\ calc\ lin}$ significantly greater than unity; while PDI was somewhat broader in the first regime (ca. 1.2-1.3), it was as low as ca. 1.1 throughout the second.

As in Examples 62 and 63, tacticity enrichment in the cyclic (co)polymer supposedly is at the heart of this peculiar behavior. Now, because of a longer PMMA homopolymer segment and, probably, a higher level of tacticity enrichment in that segment, inter-chain association supposedly occurred, which persisted in the solvent used for SEC (THF). In view of the low PDI the number of associated chains appears to be well defined and is tentatively put at 4: $M_n/4M_{n,\ cal\ lin}$ in Example 64 is then somewhat lower than the $M_n/M_{n,\ cal\ lin}$ of Examples 62 and 63, as per the supposedly higher level of tacticity enrichment in Example 64.

Thus, in view of this interpretation and by analogy to previous examples, the polymer so produced was still considered to be predominantly cyclic and the method for its production an example of the Pseudo-Ring Ring Expansion Polymerization (P-REP) process disclosed herein.

Discussion of the Results of Examples 53-64 (Table 2 and FIG. 2)

Most alkoxyamines of prior art are not able to control the homopolymerization of methacrylic monomer, cf. Nicholas, J. et al. (*Progr. Polym. Sc.* 2013, 38, 63-235) for a review). Exceptions are those that have an aromatic group as the N-substituent (cf.: Guillaneuf, Y. et al. *Macromolecules* 2007, 40, 3108-14; Greene, A. C. et al. Ibid. 2010, 43, 10320-5). However, these are of no practical industrial interest, as their cost of manufacture is prohibitive, polymerization rates are too low, and the polymer produced is colored by (fragments of) alkoxyamine included therein, hence, not ready-to-use or ready-to-formulate.

More recently, Detrembleur et al. (*Polym. Chem.* 2014, 5, 335-40) have reported the first case, wherein an alkoxyamine without an aromatic group as N-substituent is able to control MMA homopolymerization. However, being an in situ NMP process their method suffers from all the limitations noted before (Sciannamea, V. et al. *Chem. Rev.* 2008, 108, 1104-26). Thus, there is still a need for alkoxyamines that overcome these present limitations.

Alkoxyamines of Formula (8A) do not have an aromatic group as N-substituent $R^1$, but either a tertiary- (e.g., t-Bu) or a secondary alkyl (e.g., c-Hex). Thus, not surprisingly, alkoxyamine of Example 14 (disclosed herein) initiates, but does not control an MMA homopolymerization (Example 53 in Table 2; cf. FIG. 2). A similar result is obtained when using the alkoxyamine of Example 13 (Example 54).

Therefore, it is surprising and unexpected that other alkoxyamines of Formula (8A) do control homopolymerization of methacrylic monomer (Examples 55-59; cf. FIG. 2). Furthermore, they do so up to high conversion and with rates that far exceed the ones reported for N-aryl systems of prior art.

A distinctive feature in the successful alkoxyamines of Formula (8A) is the presence of —CN as $Z^1$ substituent: absent in alkoxyamines of prior art, it must have some mitigating influence in homopolymerization of methacrylic monomer to give linear polymer. For t-Bu as tertiary alkyl $R^1$ in the alkoxyamines of Formula (8A), —CN as $Z^1$ is able to exert this influence with —CN as $R^6$ (as in Examples 11 and 12), but not with an ester (as in Example 14; however, with the sterically slightly less demanding 1-cyanocyclohexyl as $R^1$ in (1A-3) it is). For c-Hex as $R^1$ in Formula (8A) —CN as $Z^1$ appears to be able to do so irrespective of the nature of $R^6$, as both the alkoxyamine of Example 17 (with —CN) and that of Example 18 (with phenyl) are able to control the homopolymerization of methacrylic monomers.

As is disclosed herein, alkoxyamine regulators of Formula (8A) are easily accessible from cheap and readily available raw materials. Thus, their use may overcome a present limitation in the application of alkoxyamines at industrial scale, i.e., facilitate homopolymerization of methacrylic and other 1,1-disubstituted monomers to produce a linear polymer.

By including a small weight fraction of styrene as comonomer control is established for alkoxyamines that fail to do so in methacrylics homopolymerization (cf. Charleux, B. et al. *Macromolecules* 2005, 38, 5485-92). Other comonomers have been used to this end (cf.: Nicholas, J. et al. *Progr. Polym. Sc.* 2013, 38, 63-235).

When using this approach with the alkoxyamine of Example 14, control can now indeed be established, as evidenced by Examples 60 and 61 (Table 2; cf. FIG. 2): in contrast to the outcome of Example 53, conversion, expressed as <ln 1/(1−c)>, now increases linearly with time, as does $M_n$ with conversion. Surprisingly and in contrast to all prior art, but as in the styrene P-REP Examples 38 and 41 (disclosed herein): when using alkoxyamine of Example 14 in methacrylics copolymerizations of Examples 60 and 61, ratios of apparent $M_n$ to $M_{n,\ calc\ lin}$ are well below unity. Thus, copolymers so produced are predominantly cyclic.

Further to that, alkoxyamines of Formula (8A) that do control homopolymerization of methacrylic monomer to give linear polymer (see above), also produce predominantly cyclic copolymer, when a small weight fraction of styrene is included (Examples 62-64, cf. FIG. 2). Thus, all alkoxyamines of Formula (8A), when used in a methacrylics copolymerization with styrene, produce predominantly cyclic copolymer.

For the alkoxyamines of Formula (8A) that are capable of controlling methacrylics homopolymerization, a ratio of ca. 2.5 to 1 styrene to alkoxyamine (Example 63), may suffice. In practice, a higher quantity seems advisable, this to suppress the formation of unsaturated PMMA oligomer at the onset of the process: by their ability to act as an addition-fragmentation chain transfer agent (cf. Moad, G. et al. In *The Chemistry of Radical Polymerization*; Elsevier, 2. Ed, 2006; pp 321-2), their presence could lead to some ring scission later on in the process and, thus, to contamination of the final cyclic polymer by linear product.

There are first indications that in the Pseudo-Ring Expansion Polymerization (P-REP) process disclosed herein tacticity enrichment of cyclic (co)polymer so produced may occur (cf. Examples 62-64). Thus, on top of potential advantages as a result of the cyclic nature of vinyl (co)polymer over its linear counterpart, the use of methacrylic monomer in the Pseudo-Ring Expansion Polymerization (P-REP) process disclosed herein, offers the added opportunity to capitalize on those resulting from tacticity enrichment in end-use applications.

Example 62 reveals that production of such a cyclic copolymer with a degree of polymerization of ca. 250 and mostly consisting of methacrylic monomer, may be achievable in a solution process at 55% polymer content in a batch time of 4 h with (extrapolated) conversion of 98%, requiring only the customary volatiles removal as a final purification step, thus in a manner fully compatible with industrial practice. As the regulators of Formulas (8A) and (1C) are easily accessible from cheap and readily available raw materials (as disclosed herein), their application at industrial scale will now enable production of this type of cyclic vinyl copolymer in a cost-effective manner.

TABLE 1

Controlled Pseudo-Ring Expansion Polymerization of Styrene[1]

| ex | Regulator R | g | Monomer M | g | Solvent S | g | T °C. | R/M | R + M % | [R] mol·l$^{-1}$ | $k_{app}$ h$^{-1}$ | time (h): | 0:15 | 0:30 | 0:45 |
|---|---|---|---|---|---|---|---|---|---|---|---|---|---|---|---|
| 37 | BB | 0.700 | Sty | 63.70 | — | — | 112 | 0.0030 | 100.0 | 0.0262 | 0.599 | c (%) | 19.78 | 31.22 | 40.76 |
| | | | | | | | | | | | | $M_{n,\ calc\ lin}$ | 6960 | 10988 | 14346 |
| | | | | | | | | | | | | $M_n$ | 7400 | 11300 | 14900 |
| | | | | | | | | | | | | $M_n/M_{n,\ calc}$ | 1.06 | 1.03 | 1.04 |
| | | | | | | | | | | | | PDI | 1.17 | 1.13 | 1.11 |
| 38 | ex. 14 | 0.550 | Sty | 64.50 | — | — | 122 | 0.0030 | 100.0 | 0.0262 | 0.494 | c (%) | 8.53 | 18.02 | 26.77 |
| | | | | | | | | | | | | $M_{n,\ calc\ lin}$ | 2900 | 6312 | 9380 |
| | | | | | | | | | | | | $M_n$ | | 6000 | 8300 |
| | | | | | | | | | | | | $M_n/M_{n,\ calc}$ | | 0.95 | 0.88 |
| | | | | | | | | | | | | PDI | | 1.32 | 1.27 |
| 39 | ex. 28 | 0.310 | Sty | 47.80 | — | — | 120 | 0.0030 | 100.0 | 0.0261 | 0.366 | c (%) | 10.97 | 17.63 | 24.64 |
| 40 | ex. 29 | 0.480 | Sty | 62.70 | — | — | 120 | 0.0030 | 100.0 | 0.0261 | 0.362 | c (%) | 6.66 | 13.94 | 21.46 |
| 41 | ex. 14 | 0.740 | Sty | 87.60 | tBB | 29.50 | 126 | 0.0030 | 75.0 | 0.0192 | 0.539 | c (%) | 9.26 | 19.66 | 29.13 |
| | | | | | | | | | | | | $M_{n,\ calc\ lin}$ | 3274 | 6952 | 10304 |
| | | | | | | | | | | | | $M_n$ | 3500 | 6500 | 9400 |
| | | | | | | | | | | | | $M_n/M_{n,\ calc}$ | 1.07 | 0.93 | 0.91 |
| | | | | | | | | | | | | PDI | 1.25 | 1.21 | 1.16 |
| 42 | ex. 11 | 0.470 | Sty | 62.50 | — | — | 120 | 0.0030 | 100.0 | 0.0261 | 0.310 | c (%) | 6.97 | 13.04 | 18.85 |
| 43 | ex. 17 | 0.520 | Sty | 62.50 | — | — | 120 | 0.0030 | 100.0 | 0.0261 | 0.302 | c (%) | 7.68 | 14.00 | 20.12 |
| 44 | ex. 25 | 0.400 | Sty | 62.70 | — | — | 112 | 0.0030 | 100.0 | 0.0264 | 0.149 | c (%) | 2.50 | 5.84 | 9.21 |
| 45 | ex. 26 | 0.350 | Sty | 62.80 | Tol | 34.00 | 112 | 0.0030 | 65.0 | 0.0167 | 0.092 | c (%) | 1.34 | 3.54 | 5.46 |
| 46 | ex. 12 | 0.573 | Sty | 62.50 | — | — | 120 | 0.0030 | 100.0 | 0.0262 | 0.405 | c (%) | 9.87 | 17.23 | 24.29 |
| 47 | ex. 13 | 0.592 | Sty | 62.50 | — | — | 120 | 0.0030 | 100.0 | 0.0262 | 0.340 | c (%) | 6.31 | 12.28 | 18.07 |
| 48 | ex. 27 | 0.465 | Sty | 47.20 | — | — | 120 | 0.0045 | 100.0 | 0.0396 | 0.512 | c (%) | 7.53 | 14.26 | 23.68 |
| 49 | ex. 21 | 0.620 | Sty | 63.00 | — | — | 112 | 0.0030 | 100.0 | 0.0264 | 0.385 | c (%) | 9.79 | 17.00 | 23.25 |
| 50 | ex. 21 | 0.905 | Sty | 91.00 | Ani | 30.70 | 122 | 0.0030 | 75.0 | 0.0204 | 0.774 | c (%) | 15.73 | 28.14 | 39.93 |
| | | | | | | | | | | | | $M_{n,\ calc\ lin}$ | 5437 | 9729 | 13806 |
| | | | | | | | | | | | | $M_n$ | 7300 | 11700 | 12300 |
| | | | | | | | | | | | | $M_n/M_{n,\ calc}$ | | | 0.89 |
| | | | | | | | | | | | | PDI | 1.64 | 1.48 | 1.40 |
| 51 | ex. 23 | 0.630 | Sty | 62.80 | — | — | 120 | 0.0030 | 100.0 | 0.0262 | 0.512 | c (%) | 8.43 | 17.38 | 27.49 |
| | | | | | | | | | | | | $M_{n,\ calc\ lin}$ | 2956 | 6099 | 9646 |
| | | | | | | | | | | | | $M_n$ | 17200 | 16900 | 17900 |
| | | | | | | | | | | | | $M_n/M_{n,\ calc}$ | na | | |
| | | | | | | | | | | | | PDI | 1.28 | 1.30 | 1.30 |
| 52 | ex. 24 | 0.600 | Sty | 62.50 | — | — | 120 | 0.0030 | 100.0 | 0.0262 | 0.337 | c (%) | 7.58 | 13.92 | 19.77 |

| ex | 1:00 | 1:15 | 1:30 | 1:45 | 2:00 | 2:15 | 2:30 | 2:45 | 3:00 | 3:30 | 4:00 |
|---|---|---|---|---|---|---|---|---|---|---|---|
| 37 | 48.29 | 55.44 | 61.61 | 67.81 | 74.55 | | | | | | |
| | 16996 | 19512 | 21685 | 23867 | 26238 | | | | | | |
| | 17800 | 20500 | 22100 | 25100 | 27400 | | | | | | |
| | 1.05 | 1.05 | 1.02 | 1.05 | 1.04 | | | | | | |
| | 1.10 | 1.10 | 1.10 | 1.10 | 1.10 | | | | | | |

TABLE 1-continued

Controlled Pseudo-Ring Expansion Polymerization of Styrene[1]

| ex | | | | | | | | | |
|---|---|---|---|---|---|---|---|---|---|
| 38 | 35.42 | 43.22 | 49.41 | 56.65 | 63.64 | 70.70 | | | |
| | 12410 | 15075 | 17314 | 19850 | 22298 | 24774 | | | |
| | 10900 | 12800 | 14600 | 17200 | 18400 | 20200 | | | |
| | 0.88 | 0.85 | 0.84 | 0.87 | 0.83 | 0.82 | | | |
| | 1.22 | 1.20 | 1.19 | 1.17 | 1.15 | 1.15 | | | |
| 39 | 32.42 | 31.00 | | | | | | | |
| 40 | 28.84 | 31.00 | | | | | | | |
| 41 | 37.89 | 44.57 | 51.21 | | 65.43 | | 76.47 | | 84.78 | 92.53 |
| | 13400 | 15762 | 18111 | | 23139 | | 27046 | | 29984 | 32724 |
| | 11400 | 13200 | 15300 | | 18700 | | 22400 | | 24700 | 76500 |
| | 0.85 | 0.84 | 0.84 | | 0.81 | | 0.83 | | 0.82 | 0.81 |
| | 1.16 | 1.15 | 1.14 | | 1.12 | | 1.11 | | 1.09 | 1.09 |
| 42 | 23.90 | 29.24 | 34.44 | 29.23 | 43.86 | 48.20 | 52.49 | 56.66 | 60.67 | 68.02 |
| 43 | 25.83 | 31.00 | 35.99 | 40.59 | 44.73 | 48.42 | 52.63 | 56.66 | 60.08 | |
| 44 | 12.60 | 15.96 | 18.81 | 21.77 | 25.06 | | | | | |
| 45 | 7.73 | 9.59 | 11.78 | 13.79 | 15.86 | | 19.94 | | 23.89 | 27.51 | 31.21 |
| 46 | 31.08 | 37.47 | 42.63 | 48.56 | 53.91 | 59.58 | 63.88 | | | |
| 47 | 23.98 | 29.22 | 34.95 | 39.86 | 44.32 | | 52.82 | | 60.13 | 66.49 | 75.28 |
| 48 | 33.61 | | | | | | | | | |
| 49 | 29.27 | 34.72 | 40.31 | 46.29 | 51.33 | 56.49 | 61.75 | 65.77 | 70.59 | |
| 50 | 49.84 | 58.22 | 65.84 | 72.58 | 78.47 | 83.72 | 89.29 | 93.12 | 97.10 | |
| | 17234 | 20133 | 22766 | 25097 | 27132 | 28948 | 30876 | 32198 | 33574 | |
| | 17900 | 20000 | 21700 | 23100 | 24500 | 25600 | 26900 | 28300 | 29000 | |
| | 1.04 | 0.99 | 0.95 | 0.92 | 0.90 | 0.88 | 0.87 | 0.88 | 0.86 | |
| | 1.38 | 1.37 | 1.37 | 1.37 | 1.37 | 1.36 | 1.35 | 1.34 | 1.33 | |
| 51 | 34.29 | 41.30 | 47.39 | 53.10 | 57.67 | 62.23 | 67.41 | | | |
| | 12031 | 14491 | 16626 | 18630 | 20233 | 21836 | 23650 | | | |
| | 19700 | 21500 | 21100 | 23400 | 25700 | 26800 | 27900 | | | |
| | 1.31 | 1.34 | 1.48 | 1.51 | 1.54 | 1.60 | 1.66 | | | |
| 52 | 26.02 | 31.96 | 37.45 | 42.87 | 48.22 | 52.82 | 58.44 | | | |

[1] R/M denotes the ratio of regulator R to monomer M; R + M (%) denotes their relative contents on total including solvent S; [R] denotes the molar concentration at 25° C.; c denotes conversion (%); from linear plots of ln l/(l − c) vs time (cf. FIG. 2), an apparent first-order rate constant of polymerization ($k_{app}$) is determind; $M_{n, calc\, lin}$ denotes the calculated $M_n$ of a liner polymer, assuming 100% efficiency of alkoxyamine; na = non applicable.

TABLE 2

Controlled Linear Homopolymerization and Pseudo-Ring Expansion Copolymerization of Methacrylics[1]

| | Regulator | | Monomer | | Solvent | | T | R/M | R + M | [R] | $k_{app}$ | | | | | |
|---|---|---|---|---|---|---|---|---|---|---|---|---|---|---|---|---|
| ex | R | g | M | g | S | g | ° C. | — | % | mol · l$^{-1}$ | h$^{-1}$ | time (h): | 0:15 | 0:30 | 0:45 | |
| 53 | ex. 14 | 0.541 | MMA | 60.70 | PrAc | 40.85 | 97 | 0.0030 | 60.0 | 0.0165 | — | c (%) | 19.31 | 24.10 | 26.50 | |
| 54 | ex. 13 | 0.595 | MMA | 60.75 | PrAc | 40.90 | 97 | 0.0030 | 60.0 | 0.0163 | — | c (%) | 13.88 | 21.47 | 26.91 | |
| 55 | ex. 11 | 0.632 | MMA | 60.10 | Tol | 32.72 | 97 | 0.0040 | 65.0 | 0.0229 | 0.321 | c (%) | 9.11 | 13.90 | 20.83 | |
| | | | | | | | | | | | | $M_{n, calc\, lin}$ | 2306 | 3518 | 5272 | |
| | | | | | | | | | | | | $M_n$ | 7802 | 9012 | 10380 | |
| | | | | | | | | | | | | $M_n/M_{n, calc}$ | 3.38 | 2.56 | 1.97 | |
| | | | | | | | | | | | | PDI | 1.31 | 1.32 | 1.33 | |
| 56 | ex. 12 | 0.766 | MMA | 60.11 | Tol | 49.83 | 97 | 0.0040 | 55.0 | 0.0197 | 0.905 | c (%) | 16.18 | 32.26 | 44.82 | |
| | | | | | | | | | | | | $M_{n, calc\, lin}$ | 4111 | 8198 | 11389 | |
| | | | | | | | | | | | | $M_n$ | 6480 | 10710 | 13885 | |
| | | | | | | | | | | | | $M_n/M_{n, calc}$ | 1.58 | 1.31 | 1.22 | |
| | | | | | | | | | | | | PDI | 1.22 | 1.21 | 1.24 | |
| 57 | ex. 17 | 0.520 | MMA | 60.90 | PrAc | 40.95 | 97 | 0.0030 | 60.0 | 0.0162 | 0.026 | c (%) | 1.21 | 1.70 | 2.32 | |
| 58 | ex. 17 | 0.550 | EMA | 63.80 | — | — | 108 | 0.0034 | 100.0 | 0.0274 | 0.260 | c (%) | 4.72 | 9.65 | 14.93 | |
| 59 | ex. 21 | 0.825 | MMA | 60.80 | Tol | 50.40 | 98-9 | 0.0040 | 55.0 | 0.0197 | 1.104 | c (%) | 11.92 | 26.97 | 41.76 | |
| | | | | | | | | | | | | $M_{n, calc\, lin}$ | 3035 | 6867 | 10630 | |
| | | | | | | | | | | | | $M_n$ | 8886 | 12427 | 15757 | |
| | | | | | | | | | | | | $M_n/M_{n, calc}$ | 2.93 | 1.81 | 1.48 | |
| | | | | | | | | | | | | PDI | 1.50 | 1.45 | 1.42 | |
| 60 | ex. 14 | 0.550 | MMA-4.4% S | 60.00 2.900 | — | — | 96 | 0.0030 | 100.0 | 0.0277 | 0.068 | c (%) | 7.40 | 8.84 | 10.08 | |
| | | | | | | | | | | | | $M_{n, calc\, lin}$ | | | 3444 | |
| | | | | | | | | | | | | $M_n$ | | | 3159 | |
| | | | | | | | | | | | | $M_n/M_{n, calc}$ | | | 0.92 | |
| | | | | | | | | | | | | PDI | | | 1.24 | |
| 61 | ex. 14 | 0.541 | EMA-4.5% S | 66.21 2.862 | Tol | 46.40 | 108 | 0.0030 | 60.0 | 0.0142 | 0.271 | c (%) | 9.04 | 14.09 | 18.75 | |
| | | | | | | | | | | | | $M_{n, calc\, lin}$ | 3443 | 5367 | 7145 | |
| | | | | | | | | | | | | $M_n$ | 2609 | 4015 | 5660 | |
| | | | | | | | | | | | | $M_n/M_{n, calc}$ | 0.76 | 0.75 | 0.79 | |
| | | | | | | | | | | | | PDI | 1.77 | 1.52 | 1.47 | |

TABLE 2-continued

Controlled Linear Homopolymerization and Pseudo-Ring Expansion Copolymerization of Methacrylics[1]

| 62 | ex. 21 | 0.825 | MMA-4.4% S | 58.40 2.800 | Tol | 50.70 | 98-9 | 0.0040 | 55.0 | 0.0196 | 0.562 1.276 | c (%) $M_{n,\ calc\ lin}$ $M_n$ $M_n/M_{n,\ cal}$ PDI | 10.40 2666 1936 0.73 1.88 | 19.55 5010 3207 0.64 1.57 | 28.18 7220 3688 0.51 1.67 |
| 63 | ex. 21 | 0.825 | MMA-1.1% S | 60.20 0.700 | Tol | 50.50 | 98-9 | 0.0040 | 55.0 | 0.0197 | 0.836 1.353 | c (%) $M_{n,\ calc\ lin}$ Mn $M_n/M_{n,\ calc}$ PDI | 11.94 3044 3544 1.16 1.56 | 24.94 6360 4586 0.72 1.57 | 28.18 9436 5287 0.56 1.66 |
| 64 | ex. 11 | 0.750 | MMA-4.0% S | 68.00 2.950 | Tol | 38.60 | 98-9 | 0.0040 | 65.0 | 0.0237 | 0.131 0.377 | c (%) $M_{n,\ calc\ lin}$ $M_n$ $M_n/M_{n,\ calc}$ $M_n/3M_{n,\ calc}$[2] $M_n/4M_{n,\ calc}$[2] PDI | 5.79 | 9.56 2407 6100 2.53 0.84 0.63 1.10 | 12.90 3249 5100 1.57 0.52 0.39 1.24 |

| ex | 1:00 | 1:15 | 1:30 | 2:00 | 2:30 | 3:00 | 3:30 | 4:00 | 4:30 | 5:00 |
|---|---|---|---|---|---|---|---|---|---|---|
| 53 | 28.06 | 29.00 | 29.36 | 30.05 | 30.55 | 31.26 | 31.70 | 32.37 | | |
| 54 | 30.88 | 33.78 | 36.08 | 38.54 | 39.44 | 39.84 | 39.83 | | | |
| 55 | 29.69 | | 39.65 | 48.55 | 53.69 | 59.76 | 67.55 | 72.43 | 77.13 | |
|  | 7516 | | 10036 | 12290 | 13591 | 15126 | 17098 | 18334 | 19522 | |
|  | 11308 | | 14282 | 15462 | 16030 | 16936 | 18158 | 18971 | 19953 | |
|  | 1.50 | | 1.42 | 1.26 | 1.18 | 1.12 | 1.06 | 1.03 | 1.02 | |
|  | 1.34 | | 1.36 | 1.41 | 1.45 | 1.47 | 1.49 | 1.50 | 1.50 | |
| 56 | 54.61 | | 69.40 | 81.96 | 89.53 | 93.24 | 95.15 | 97.09 | | |
|  | 13877 | | 17635 | 20828 | 22751 | 23694 | 24178 | 24672 | | |
|  | 16596 | | 21061 | 24830 | 25705 | 26464 | 27997 | 28601 | | |
|  | 1.20 | | 1.19 | 1.19 | 1.13 | 1.12 | 1.16 | 1.16 | | |
|  | 1.26 | | 1.36 | 1.43 | 1.51 | 1.52 | 1.48 | 1.48 | | |
| 57 | 2.84 | 3.34 | 4.02 | 5.28 | 6.54 | 7.87 | 9.31 | | | |
| 58 | 19.34 | 25.76 | 31.13 | 43.63 | 57.07 | | | | | |
| 59 | 53.25 | 64.60 | 73.33 | 86.17 | 92.35 | | | | | |
|  | 13556 | 16446 | 18669 | 21938 | 23511 | | | | | |
|  | 19740 | 21403 | 22016 | 22991 | 26273 | | | | | |
|  | 1.46 | 1.30 | 1.18 | 1.05 | 1.12 | | | | | |
|  | 1.35 | 1.37 | 1.43 | 1.51 | 1.44 | | | | | |
| 60 | 11.45 | 13.00 | 14.48 | 17.33 | 20.68 | 2425 | 28.73 | 31.82 | | |
|  | | 4444 | | 5921 | | 8286 | | 10876 | | |
|  | | 4294 | | 5568 | | 7627 | | 9612 | | |
|  | | 0.97 | | 0.94 | | 0.92 | | 0.88 | | |
|  | | 1.59 | | 1.53 | | 1.46 | | 1.42 | | |
| 61 | 23.51 | 28.65 | 32.82 | 41.17 | 48.85 | 56.43 | 62.03 | | | |
|  | 8959 | 10916 | 12504 | 15685 | 18615 | 21503 | 23633 | | | |
|  | 7085 | 8406 | 9693 | 12372 | 14631 | 16893 | 18963 | | | |
|  | 0.79 | 0.77 | 0.78 | 0.79 | 0.79 | 0.79 | 0.80 | | | |
|  | 1.44 | 1.45 | 1.44 | 1.44 | 1.46 | 1.48 | 1.50 | | | |
| 62 | 36.40 | 44.33 | 51.68 | 65.50 | 79.00 | 90.37 | | | | |
|  | 9326 | 11359 | 13241 | 16782 | 20241 | 23154 | | | | |
|  | 4396 | 5086 | 5728 | 6647 | 8284 | 9323 | | | | |
|  | 0.47 | 0.45 | 0.43 | 0.40 | 0.41 | 0.40 | | | | |
|  | 1.69 | 1.70 | 1.69 | 1.70 | 1.62 | 1.58 | | | | |
| 63 | 47.75 | 57.40 | 66.96 | 79.31 | 89.48 | | | | | |
|  | 12176 | 14637 | 17074 | 20224 | 22817 | | | | | |
|  | 6216 | 7105 | 7828 | 8488 | 10041 | | | | | |
|  | 0.51 | 0.49 | 0.46 | 0.42 | 0.44 | | | | | |
|  | 1.65 | 1.67 | 1.68 | 1.76 | 1.65 | | | | | |
| 64 | 14.86 | 17.79 | 20.38 | 25.06 | 30.21 | 35.11 | 45.00 | 54.68 | | 69.3 |
|  | 3741 | 4479 | 5131 | 6311 | 7608 | 8841 | 11331 | 13768 | | 17454 |
|  | 6300 | 6600 | 7500 | 14900 | 15800 | 19000 | 17400 | 19900 | | 22600 |
|  | 1.68 | 1.47 | 1.46 | 2.36 | 2.08 | 2.15 | 1.54 | 1.45 | | 1.29 |
|  | 0.56 | 0.49 | 0.49 | 0.79 | 0.69 | 0.72 | 0.51 | 0.48 | | 0.43 |
|  | 0.42 | 0.37 | 0.37 | 0.59 | 0.52 | 0.54 | 0.38 | 0.36 | | 0.32 |
|  | 1.21 | 1.28 | 1.31 | 1.09 | 1.13 | 1.08 | 1.16 | 1.14 | | 1.13 |

[1] R/M denotes the ratio of regulator R to monomer M; R + M (%) denotes their relative contents on total including solvent S; [R] denotes the molar concentration at 25° C.; c denotes conversion (%); from linear plots of ln l/(1 − c) vs. time (cf. FIG. 2), an apparent first-order rate constant of polymerization ($k_{app}$) is determind: 2 values are reported when there are 2 distinct regimes; $M_{n,\ calc\ lin}$ denotes the calculated $M_n$ of a liner polymer, assuming 100% efficiency.
[2] See text under Example 64.

What is claimed is:

1. Regulator compounds according to any one of the Formulas 1A, 1B, 1C, 1D, 1E, 1F, 1G, 1H and 1I:

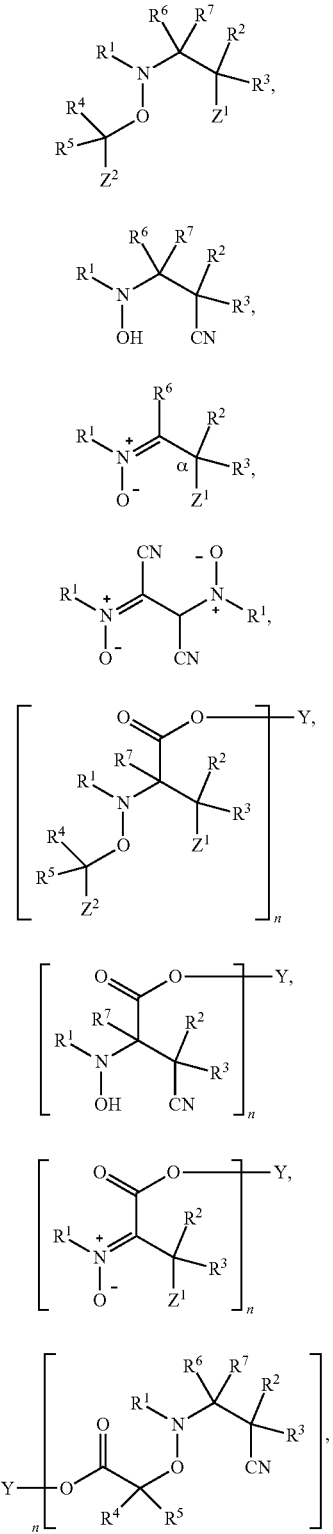

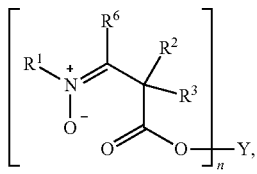

wherein
$R^1$ stands for an optionally substituted secondary or tertiary alkyl or secondary or tertiary aralkyl;
$Z^1$ stands for —CN or a carboxylic acid ester of formula $C(O)OR^{21}$;
$Z^2$ is chosen from the group of —CN, carboxylic acid, salts of carboxylic acids, carboxylic acid ester, carboxylic acid amides, (hetero)aryl, alkenyl and halogen;
$R^2$, $R^3$, $R^4$ and $R^5$ are each independently chosen from the group of H, alkyl, aralkyl, (hetero)aryl, —CN and carboxylic acid ester of formula $C(O)OR^{22}$;
$R^7$ stands for a primary alkyl or primary aralkyl, —CN or hydrogen;
Y stands for a bridging group and n is 2, 3, 4, 5 or 6;
in case $R^1$ stands for tertiary alkyl or tertiary aralkyl, $R^6$ stands for a primary alkyl or primary aralkyl, —CN or a carboxylic acid ester of formula $C(O)OR^{26}$;
in case $R^1$ stands for a secondary alkyl or secondary aralkyl, $R^6$ stands for a primary or secondary alkyl or primary or secondary aralkyl, —CN, a carboxylic acid ester of formula $C(O)OR^{26}$ or a phosphonic acid ester of formula $P(O)(OR^{27})_2$, a (hetero)aryl or an alkenyl;
$R^{21}$, $R^{22}$, $R^{26}$ and $R^{27}$ stand for alkyl or aralkyl having from 1-30 carbon atoms, optionally containing heteroatoms, wherein the regulator compounds are suitable for polymerization of vinyl monomers, and
with the proviso that for regulator compound (1C) when $R^6$ and $Z^1$ are the carboxylic acid esters, $R^1$ is substituted and includes a polar substituent that is one or more of —CN, carboxylic acid ester, phosphonate ester and hydroxy.

2. Regulator compounds according to claim 1, wherein $R^1$ selected from isopropyl, sec-butyl, tert-butyl, 3-pentyl, tert-amyl, cyclohexyl, 2,4-dimethyl-3-pentyl, 2,2,4-trimethyl-3-pentyl, 1-adamantyl, 1-phenylethyl, 2-methyl-1-phenyl-1-propyl, diphenylmethyl, 1-cyanocyclohexyl, 1-(methoxycarbonyl)-2-methyl-1-propyl, 1-(diethoxyphosphoryl)-2,2-dimethylpropyl, 1-hydroxy-2-methyl-2-propyl and 1,3-dihydroxy-2-(hydroxymethyl)-2-propyl, with the proviso that for regulator compound (1C) when $R^6$ and $Z^1$ are the carboxylic acid esters, $R^1$ is substituted and includes the polar substituent that is one or more of —CN, carboxylic acid ester, phosphonate ester and hydroxy.

3. Regulator compounds according to claim 1, wherein $R^1$ is chosen from the group consisting of tert-butyl, cyclohexyl, 2-methyl-1-phenyl-1-propyl, with the proviso that for regulator compound (1C) $Z^1$ is —CN.

4. Regulator compounds according to claim 1, wherein $Z^1$ is chosen from —CN and a carboxylic acid ester of formula $C(O)OR^{21}$ with the proviso that for regulator compound (1C) $Z^1$ stands only for —CN, wherein $R^{21}$ stands methyl, ethyl, tert-butyl, benzyl, cyclohexyl, 2-hydroxyethyl, 2-methoxyethyl, 2-acetoacetoxyethyl and 2,3-epoxypropyl.

5. Regulator compounds according to claim 1, wherein $Z^1$ stands for —CN or C(O)OMe with the proviso that for regulator compound (1C) $Z^1$ stands only for —CN.

6. Regulator compounds according to claim 1, wherein $R^2$, $R^4$ and $R^5$ are each independently chosen from H, methyl and ethyl.

7. Regulator compounds according to claim 1, wherein $R^3$ is chosen from H, methyl, ethyl, —CN, C(O)OMe or C(O)OEt.

8. Regulator compounds according to claim 1, wherein in case $R^1$ stands for a tertiary alkyl or tertiary aralkyl (preferably tert-butyl), $R^6$ stands for a primary alkyl having from 1-18 C-atoms, a primary aralkyl having from 7-18 C-atoms, —CN or a carboxylic acid ester of formula $C(O)OR^{26}$, with the proviso that for regulator compound (1C) $Z^1$ is —CN.

9. Regulator compounds according to claim 1, wherein $R^6$ is selected from the group consisting of methyl, ethyl, 1-propyl, isobutyl, 2-ethylbutyl, 2-ethylhexyl, benzyl, 2-phenylethyl, —CN, C(O)OMe and C(O)OEt.

10. Regulator compounds according to claim 1, wherein in case $R^1$ stands for a secondary alkyl or secondary aralkyl, $R^6$ stands for a primary or secondary alkyl having from 1-30 C-atoms, a primary or secondary aralkyl having from 7-18 C-atoms, —CN, a carboxylic acid ester of formula $C(O)OR^{26}$ or a phosphonic acid ester of formula $P(O)(OR^{27})_2$, a (hetero)aryl or an alkenyl, with the proviso that for regulator compound (1C) $Z^1$ is —CN.

11. Regulator compounds according to claim 10, wherein $R^6$ is chosen from the group consisting of methyl, ethyl, 1-propyl, isobutyl, 2-ethylbutyl, 2-ethylhexyl, benzyl, 2-phenylethyl, isopropyl, cyclohexyl, 1-phenylethyl, phenyl, 2-furyl, 2-pyridyl, ethenyl (vinyl), 1-methylethenyl (isopropenyl), 2-phenylethen-1-yl, 1-propen-1-yl and 2-methyl-1-propen-1-yl.

12. Regulator compounds according to claim 10, wherein $R^6$ is chosen from the group consisting of —CN, phenyl, C(O)OMe, C(O)OEt, $P(O)(OEt)_2$ and isopropyl.

13. Regulator compounds according to claim 1, wherein $R^7$ is chosen from the group consisting of methyl, ethyl, 1-propyl, isobutyl, 2-ethylbutyl, 2-ethylhexyl, benzyl and 2-phenylethyl, preferably $R^7$ is hydrogen or methyl.

14. Regulator compounds according to claim 1, wherein $Z^2$ may stand for —CN, a carboxylic acid ester of formula $C(O)OR^{22}$, a carboxylic acid or its salt, a carboxyl acid amide, a (hetero)aryl, an alkenyl or a halogen.

15. Regulator compounds according to claim 1, wherein $Z^2$ is chosen from the group consisting of phenyl, 2-furyl, 2-pyridyl, ethenyl (vinyl), 1-methylethenyl (isopropenyl), 2-phenylethen-1-yl, 1-propen-1-yl, and 2-methyl-1-propen-1-yl.

16. Regulator compounds according to claim 1, wherein $R^{22}$, $R^{26}$ and $R^{27}$ are independently chosen from the group consisting of methyl, ethyl, n-butyl, tert-butyl, benzyl, cyclohexyl, 2-hydroxyethyl, 2-acetoacetoxyethyl and 2,3-epoxypropyl; preferably, $R^{22}$ is chosen from methyl, ethyl and cyclohexyl, $R^{26}$ is chosen from methyl, benzyl and tert-butyl, and $R^{27}$ is chosen from ethyl and n-butyl.

17. Regulator compounds according to claim 1, wherein Y is selected from the group consisting of 1,2-ethanediyl, 2,2-dimethyl-1,3-propanediyl, 1,4-butanediyl, 1,6-hexanediyl, pentaerythrityl and dipentaerythrityl.

18. Regulator compounds according to claim 1, wherein the compounds consist of anyone of the following structures:

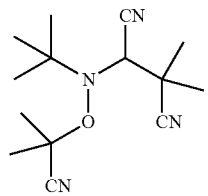 (1A-1)

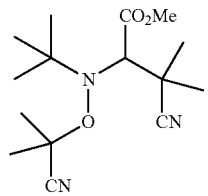 (1A-2)

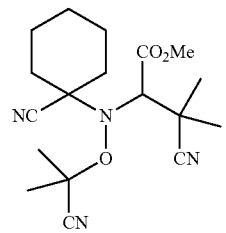 (1A-3)

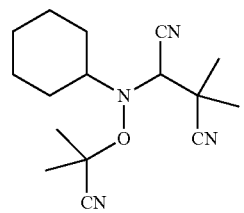 (1A-4)

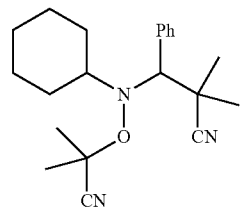 (1A-5)

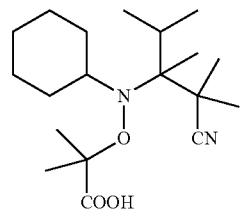 (1A-6)

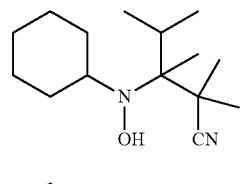 (1B-1)

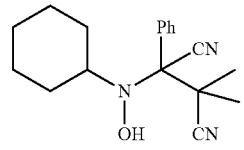 (1B-2)

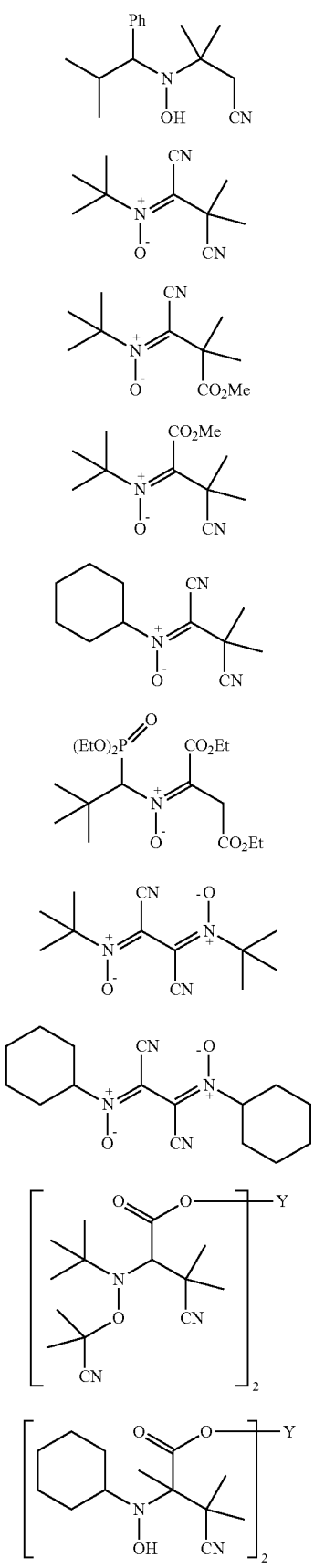
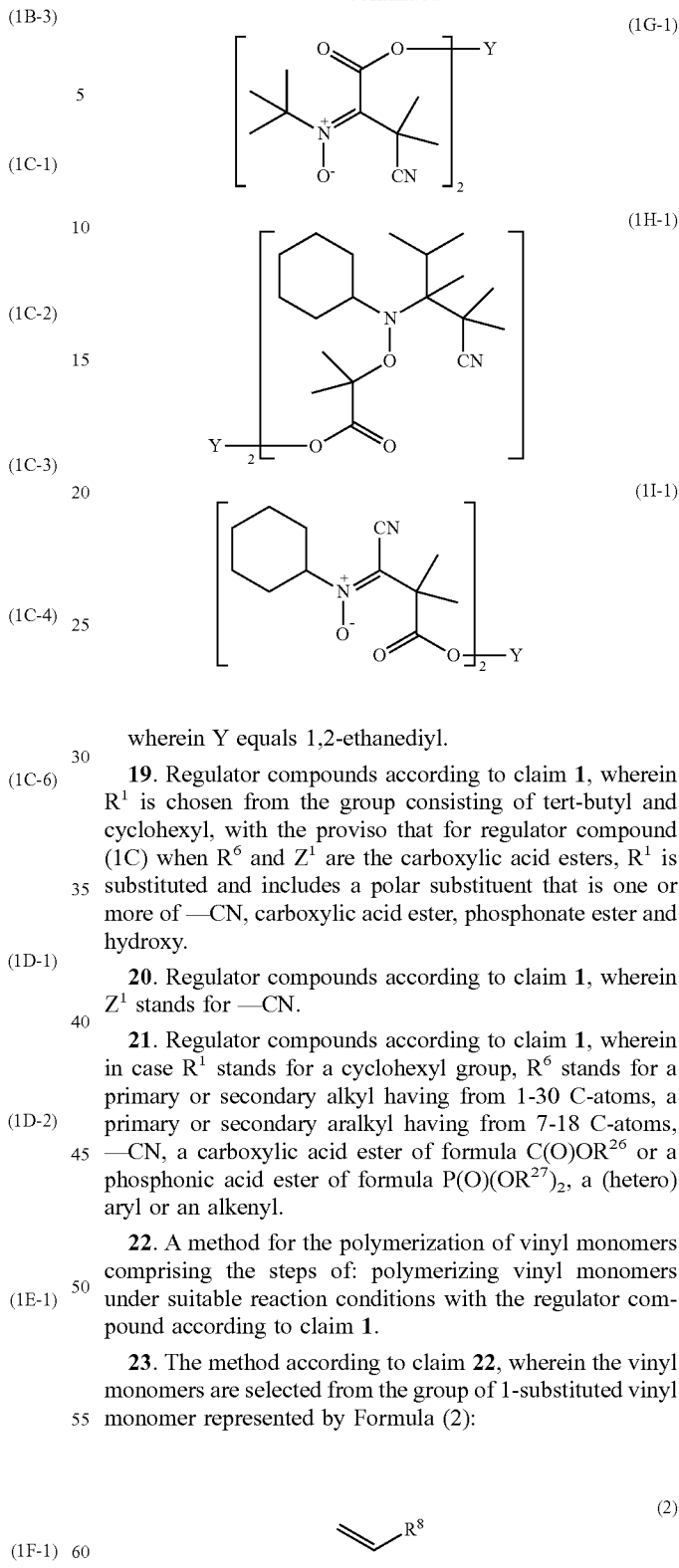

wherein Y equals 1,2-ethanediyl.

19. Regulator compounds according to claim 1, wherein $R^1$ is chosen from the group consisting of tert-butyl and cyclohexyl, with the proviso that for regulator compound (1C) when $R^6$ and $Z^1$ are the carboxylic acid esters, $R^1$ is substituted and includes a polar substituent that is one or more of —CN, carboxylic acid ester, phosphonate ester and hydroxy.

20. Regulator compounds according to claim 1, wherein $Z^1$ stands for —CN.

21. Regulator compounds according to claim 1, wherein in case $R^1$ stands for a cyclohexyl group, $R^6$ stands for a primary or secondary alkyl having from 1-30 C-atoms, a primary or secondary aralkyl having from 7-18 C-atoms, —CN, a carboxylic acid ester of formula $C(O)OR^{26}$ or a phosphonic acid ester of formula $P(O)(OR^{27})_2$, a (hetero) aryl or an alkenyl.

22. A method for the polymerization of vinyl monomers comprising the steps of: polymerizing vinyl monomers under suitable reaction conditions with the regulator compound according to claim 1.

23. The method according to claim 22, wherein the vinyl monomers are selected from the group of 1-substituted vinyl monomer represented by Formula (2):

wherein $R^8$ stands for an optionally substituted (hetero) aryl or alkenyl, halogen, —CN, carboxylic acid, a salt of carboxylic acid, carboxylic acid ester or carboxylic acid amide; or from the group of 1,1-disubstituted vinyl monomer represented by Formula (3):

(3)

wherein in case $R^9$ stands for an optionally substituted (hetero)aryl or alkenyl, —CN, carboxylic acid, a salt of carboxylic acid, carboxylic acid ester or carboxylic acid amide, $R^{10}$ stands for an alkyl, most preferably a methyl, or wherein in case $R^9$ stands for halogen, $R^{10}$ also stands for halogen or for an optionally substituted alkenyl.

24. The method according to claim 22, wherein the vinyl monomers are mixtures selected from the group of 1-substituted vinyl monomer of Formula (2) and/or from the group of 1,1-disubstituted vinyl monomer of Formula (3), optionally in combination with vinyl comonomer selected from the group of 1,2-disubstituted vinyl monomer represented by Formula (4):

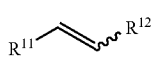
(4)

wherein in case $R^{12}$ stands for an optionally substituted (hetero)aryl, —CN or carboxylic acid, including its salts, esters and amides, $R^{11}$ stands for an optionally substituted (hetero)aryl, —CN, carboxylic acid, including its salts, esters and amides, or alkyl, and wherein $R^{11}$ and $R^{12}$ may optionally form a ring.

25. The method according to claim 22, wherein the vinyl monomers comprise at least one of styrene (S), isoprene (I), butadiene (B), acrylic acid (AA), butyl acrylate (BA), 2-ethyhexyl acrylate (EHA), methacrylic acid (MAA), methyl methacrylate (MMA) and maleic anhydride (MA).

26. Linear polymers prepared in a process according to claim 22, having Formulas (10):

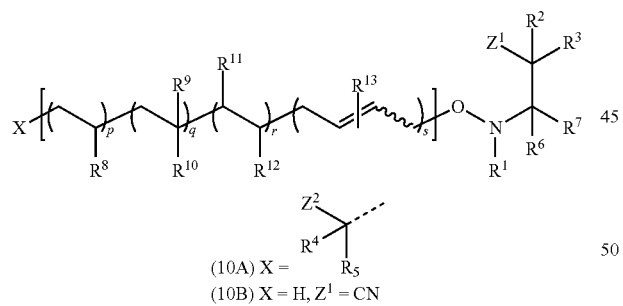

(10A) X = 
(10B) X = H, $Z^1$ = CN where linear polymers according to Formula (10A) are obtained when using regulator compounds of Formula (1A) and those according to Formula (10B) when using (1B), in each case provided that either $R^7$ is a primary alkyl or —CN (in the latter case with a tertiary alkyl as $R^1$), with all other substituents as defined above, wherein p represents the average number of one or more types of vinyl monomer units of Formula (2) incorporated in the polymer and p ranges between 0 and 100.000;

wherein q represents the average number of one or more types of vinyl monomer units of Formula (3) incorporated in the polymer and q ranges between 0 and 100.000;

wherein r represents the average number of one or more types of vinyl comonomer units of Formula (4) incorporated in the polymer, and r ranges between 0 and 100.000;

wherein s represents the average number of one or more types of diene monomer units incorporated in the polymer by cis- and/or trans- 1,4- and/or 4,1-addition, $R^{13}$ stands for hydrogen, methyl and/or halogen, and s ranges between 0 and 100.000;

wherein p+q+r+s is at least 10.

27. Cyclic polymers prepared in a process according to claim 22, having Formula (11):

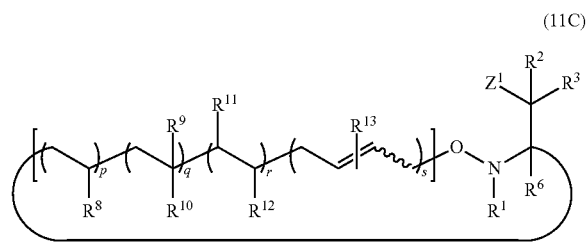
(11C)

where the monocyclic polymers according to Formula (11C) are obtained when using the regulator compounds of Formula (1C) with all substituents and subscripts as defined above provided that $R^7$ is hydrogen.

28. Polymer obtainable by the method according to claim 22, wherein by using the multi-functional regulators of Formulas (1E), (1F) and (1H) multiple linear polymer segments will be linked to give 2-arm linear (for n=2), 3-arm star (n=3), 4-arm star (n=4), etc. polymer architectures of Formulas (10E), (10F) and (10H), respectively:

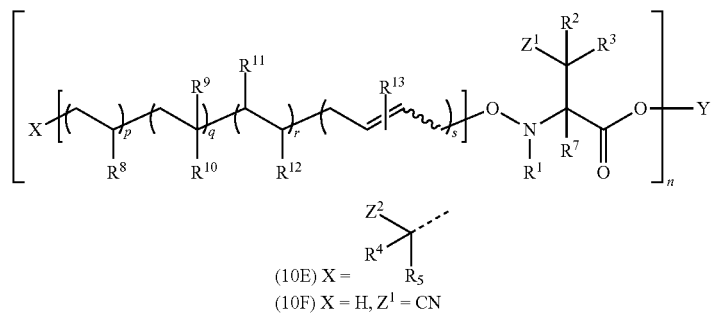

(10E) X = 
(10F) X = H, $Z^1$ = CN

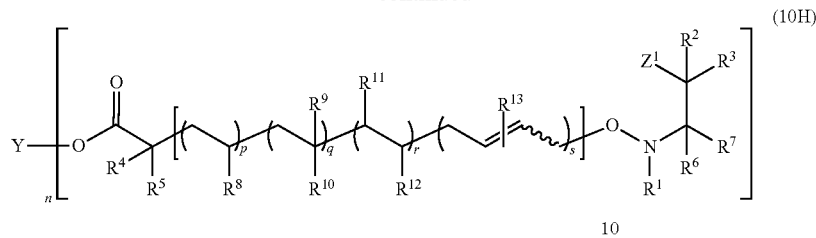

in each case provided that either $R^7$ is a primary alkyl or —CN (in the latter case with a tertiary alkyl as $R^1$), wherein Y and n, as well as all further substituents and subscripts are as defined above.

29. Polymer obtainable by the method according to claim 22, wherein when using the multi-functional regulators of Formulas (1D), (1G) and (1I) multiple cyclic polymers will be linked into one polymer architecture, as is represented by Formulas (11D), (11G) or (11I), respectively:

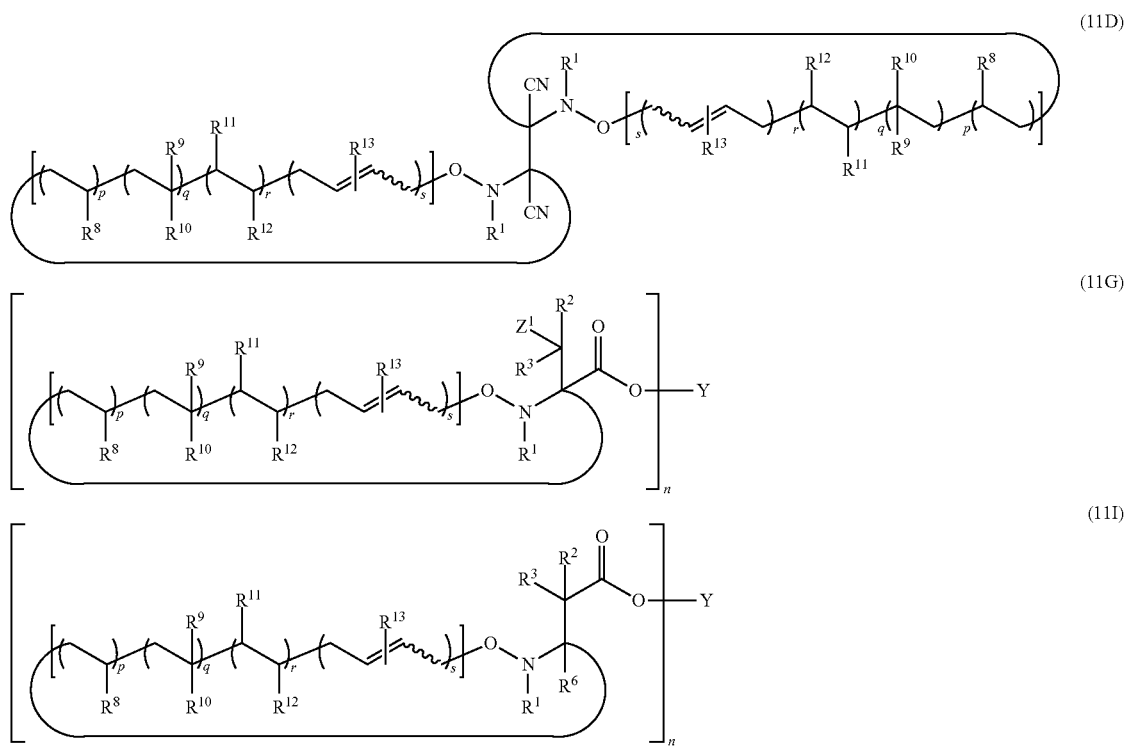

wherein all substituents, as well as Y and all subscripts are as defined above.

30. A process for the preparation of regulator compounds of Formulas (1A) and (1E) according to claim 1, wherein $R^5$ is identical to $R^2$, $R^4$ is identical to $R^3$, $Z^2$ is identical to $Z^1$ and $R^7$ is H, which can be represented by the alkoxyamines of Formulas (8A) and (8E):

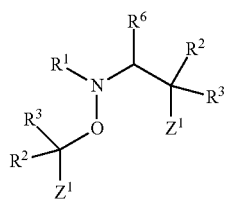

wherein $Z^1$ stands for —CN or a carboxylic acid ester of formula $C(O)OR^{21}$, wherein in case $R^2$ stands for Me or Et, $R^3$ stands for a primary alkyl, wherein in case $R^1$ stands for a tertiary alkyl or tertiary aralkyl, $R^6$ stands for —CN or a carboxylic acid ester of formula $C(O)OR^{26}$, or wherein in case $R^1$ stands for a secondary alkyl or secondary aralkyl, $R^6$ stands for —CN, a carboxylic acid ester of formula C(O)OR$^{26}$ or a phosphonic acid ester of formula P(O)(OR$^{27}$)$_2$, a (hetero) aryl or an alkenyl, with R$^{21}$, R$^{26}$, R$^{27}$, Y and n as defined above, by reaction of the corresponding aldonitrones of Formulas (6):

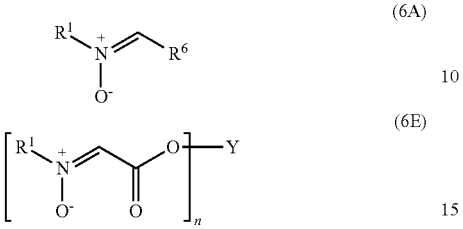

wherein R$^1$, R$^6$, Y and n are as defined above, and the corresponding azo-compound of Formula (7):

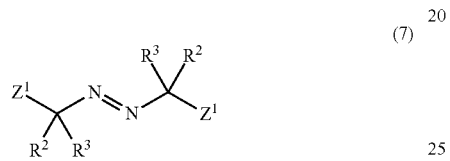

wherein R$^2$, R$^3$ and Z$^1$ are as defined above, in a 1,3-di-tert-radical addition reaction.

31. A process for the preparation of specific nitrone regulators of Formulas (1C) and (1G):

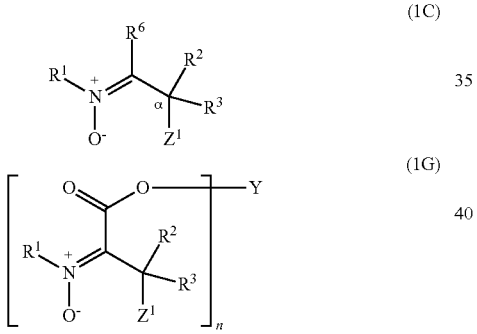

wherein Z$^1$ stands for —CN or a carboxylic acid ester of formula C(O)OR$^{21}$, wherein in case R$^2$ stands for Me or Et, R$^3$ stands for a primary alkyl, wherein in case R$^1$ stands for a tertiary alkyl or tertiary aralkyl, R$^6$ stands for —CN or a carboxylic acid ester of formula C(O)OR$^{26}$, or wherein in case R$^1$ stands for a secondary alkyl or secondary aralkyl, R$^6$ stands for —CN, a carboxylic acid ester of formula C(O)OR$^{26}$ or a phosphonic acid ester of formula P(O)(OR$^{27}$)$_2$, a (hetero) aryl or an alkenyl, with R$^{21}$, R$^{26}$, R$^{27}$, Y and n as defined above, from the corresponding alkoxyamines of Formulas (8A) and (8E) prepared according to claim 30, respectively:

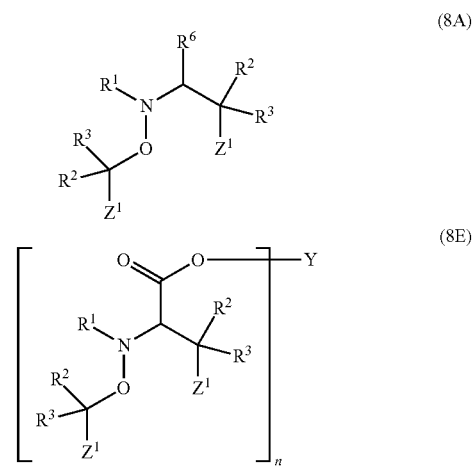

wherein R$^1$, R$^2$, R$^3$, R$^6$, Z$^1$, Y and n are as defined above, by their treatment with a metal alkoxide or amine base, with the proviso that for regulator compound (1C) when R$^6$ and Z$^1$ are the carboxylic acid esters, R$^1$ is substituted and includes the polar substituent that is one or more of —CN, carboxylic acid ester, phosphonate ester and hydroxy.

* * * * *